US006737429B2

(12) United States Patent
Dymock et al.

(10) Patent No.: US 6,737,429 B2
(45) Date of Patent: May 18, 2004

(54) PYRROLE DERIVATIVES

(75) Inventors: Brian William Dymock, St. Albans (GB); Philip Stephen Jones, Welwyn Garden City (GB); John Herbert Merrett, Baldock (GB); Martin John Parratt, Hertford (GB)

(73) Assignee: Hoffmann-La Roche Inc., Nutley, NJ (US)

( * ) Notice: Subject to any disclaimer, the term of this patent is extended or adjusted under 35 U.S.C. 154(b) by 153 days.

(21) Appl. No.: 09/880,534

(22) Filed: Jun. 13, 2001

(65) Prior Publication Data

US 2002/0032221 A1 Mar. 14, 2002

(30) Foreign Application Priority Data

Jul. 4, 2000 (GB) ............................................... 0016453

(51) Int. Cl.[7] ........................ A61K 31/44; C07D 401/00

(52) U.S. Cl. ..................................... 514/343; 546/276.4

(58) Field of Search ........................ 546/276.4; 514/343

(56) References Cited

U.S. PATENT DOCUMENTS

| 3,644,631 A | | 2/1972 | Pachter et al. |
|---|---|---|---|
| 4,282,242 A | | 8/1981 | Holland |
| 4,347,186 A | * | 8/1982 | Muchowski et al. |

FOREIGN PATENT DOCUMENTS

| EP | 959 074 | 11/1999 |
|---|---|---|
| WO | WO 95/33727 | 12/1995 |
| WO | WO 96/18628 | 6/1996 |
| WO | WO 98/02430 | 1/1998 |

OTHER PUBLICATIONS

English language abstract of WO 01/47878, the equivalent of DE 199 63 174 listed on the Search Report.

* cited by examiner

Primary Examiner—Alan L. Rotman
Assistant Examiner—Binta Robinson
(74) Attorney, Agent, or Firm—George W. Johnston; Dennis P. Tramaloni; Lyman H. Smith

(57) ABSTRACT

Disclosed are novel pyrrole derivatives, a process for their manufacture, pharmaceutical compositions containing such compounds and the use of such compounds in the treatment of HIV mediated diseases.

26 Claims, No Drawings

PYRROLE DERIVATIVES

BACKGROUND OF THE INVENTION

The invention is concerned with novel pyrrole derivatives, a process for their manufacture, pharmaceutical compositions and the use of such compounds in the treatment of viral diseases. In particular, the compounds are inhibitors of the human immunodeficiency virus reverse transcriptase enzyme which is involved in viral replication. Consequently the compounds of this invention are useful in the treatment or therapy of diseases mediated by the human immunodeficiency virus (HIV).

The disease Acquired Immunodeficiency Syndrome (AIDS) is the end result of infection by the distinct retroviruses, human immunodeficiency virus type-1 (HIV-1) or type-2 (HIV-2). Several critical points in the virus's life cycle have been identified as possible targets for therapeutic intervention. Inhibition of one of these, the transcription of viral RNA to viral DNA (reverse transcriptase, RT), has provided a number of the current therapies used in treating AIDS. Inhibition of reverse transcriptase provided the first form of treatment for HIV infection with 3'-azido-3'-deoxythymidine (AZT). Since then several inhibitors have been launched, broadly forming two classes: nucleoside analogues and non-nucleosides. As an example of the latter it has been found that certain benzoxazinones, e.g. efavirenz are useful in the inhibition of HIV RT. However, development of strains of the virus resistant to current RT inhibitors is a constant problem. Therefore, development of compounds effective against resistant strains is an important goal.

Certain pyrrole derivatives have been disclosed to have therapeutic utilities.

U.S. Pat. No. 3,644,631 describes pyrrole derivatives effective for the therapy of inflammatory syndromes.

U.S. Pat. No. 4,282,242 describes pyrrole derivatives effective for the therapy of lowering the blood glucose level in hyperglycemic mammals.

SUMMARY OF THE INVENTION

The object of the present invention is to provide novel compounds which are potent inhibitors of the human immunodeficiency virus reverse transcriptase enzyme, which is involved in viral replication, and which accordingly are useful as antiviral drugs. Specifically, this invention is directed to the compounds of formula I

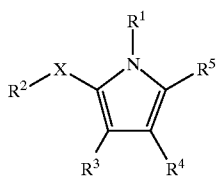

I wherein $R^1$, $R^2$, $R^3$, $R^4$, and $R^5$ are as defined below.

This invention is also directed to pharmaceutical compositions containing compounds for formula I and the use of the compositions in the treatment or therapy of HIV.

DETAILED DESCRIPTION OF THE INVENTION

This invention is directed, inter alia, to a compound of formula

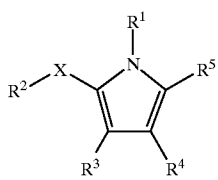

I wherein $R^1$ is alkyl, cycloalkyl, aryl or heterocyclyl;
$R^2$ is alkyl cycloalkyl, aryl or heterocyclyl;
$R^3$ is hydrogen, alkyl, cycloalkyl, aryl or heterocyclyl;
$R^4$ is hydrogen, alkyl, carboxyl, C(=O)R, CONR'R'', cyano or alkenyl;
R is hydrogen, alkyl, alkoxy, trifluoromethyl, methyl-oxy-carbonyl or ethyl-oxy-carbonyl;
R' and R'', are each independently selected from hydrogen, alkyl or aryl;
$R^5$ is alkyl, aryl or a group —Z—C(=O)R''';
Z is a single bond or —CH=CH—;
R''' is hydrogen or alkyl;
X represents S, S(O), S(O)$_2$, O, N(alkyl), or X—$R^2$ together represent CH$_2$-aryl or CH$_2$-heterocyclyl;
provided that only one of $R^3$ and $R^4$ is hydrogen, and provided further that alkyl in $R^3$ is not CF$_3$;
or hydrolyzable esters or ethers of the foregoing compound, or a pharmaceutically acceptable salt thereof.

The term "alkyl" as used herein, and if not otherwise specified by the number of carbon atoms, denotes an optionally substituted straight or branched chain hydrocarbon residue containing 1 to 7 carbon atoms, such as methyl, ethyl, n-propyl, isopropyl, n-butyl, sec-butyl, isobutyl, tert.-butyl, pentyl, hexyl, heptyl, including their different isomers.

Suitable substituents for the alkyl chain can be selected from one or more of
aryl, heterocyclyl,
carboxyl,
alkoxy, cycloalkyl oxy, aryl oxy, heterocyclyl oxy, hydroxy,
amino carbonyl oxy, alkyl amino carbonyl oxy, dialkyl amino carbonyl oxy, aryl amino carbonyl oxy, heterocyclyl amino carbonyl oxy,
alkyl carbonyl, cycloalkyl carbonyl, aryl carbonyl, heterocyclyl carbonyl,
hydroxy carbonyl, alkoxy carbonyl, cycloalkyl oxy carbonyl, aryl oxy carbonyl, heterocyclyl oxy carbonyl,
amino carbonyl, alkyl amino carbonyl, dialkyl amino carbonyl, cycloalkyl amino carbonyl, aryl amino carbonyl, heterocyclyl amino carbonyl,
amino, alkyl amino, dialkyl amino, cycloalkyl amino, aryl amino, heterocyclyl amino,
alkyl carbonyl amino, cycloalkyl carbonyl amino, aryl carbonyl amino, heterocyclyl carbonyl amino,
alkoxy carbonyl amino, cycloalkyl oxy carbonyl amino, aryloxy carbonyl amino, heterocylyl oxy carbonyl amino,
alkyl amino carbonyl amino, dialkyl amino carbonyl amino, cycloalkyl amino carbonyl amino,
aryl amino carbonyl amino, heterocyclyl amino carbonyl amino,
alkyl sulfonyl amino, cycloalkyl sulfonyl amino, aryl sulfonyl amino, heterocyclyl sulfonyl amino,
nitro,
alkyl sulfinyl, cycloalkyl sulfinyl, aryl sulfinyl, heterocyclyl sulfinyl,
alkyl sulfonyl, cycloalkyl sulfonyl, aryl sulfonyl, heterocyclyl sulfonyl,
alkyl thio, cycloalkyl thio, aryl thio, heterocyclyl thio or halogen.

In case more than one substituent is attached to the alkyl group, these substituents can be identical or different from each other.

The suitable substituents for the alkyl group aryl and heterocyclyl may be substituted with 1–3 substituents, preferably 1–2 substituents, more preferably 1 substituent selected from $C_{1-4}$-alkyl (preferably methyl), $C_{1-4}$-alkoxy (preferably methoxy), halogen (preferably chlorine) or trifluoromethyl. Examples for substituted alkyl are cyclopropylmethyl, cyclobutylmethyl, cyclopentylmethyl, cyclohexylmethyl, 2-pyridylmethyl, 2-pyridylethyl, 2-pyridylpropyl, 2-pyridylbutyl, methyl-2-pyridyl-methyl, methyl-2-pyridyl-ethyl, dimethyl-2-pyridyl-methyl, ethyl-2-pyridyl-methyl, methoxy-2-pyridyl-methyl, methoxy-2-pyridyl-ethyl, dimethoxy-2-pyridyl-methyl, fluoro-2-pyridyl-methyl, difluoro-2-pyridyl-methyl, chloro-2-pyridyl-methyl, chloro-2-pyridyl-ethyl, dichloro-2-pyridyl-methyl, dichloro-2-pyridyl-methyl, bromo-2-pyridyl-methyl, dibromo-2-pyridyl-methyl, 3-pyridyl-methyl, 3-pyridyl-ethyl, 3-pyridyl-propyl, 3-pyridyl-butyl, methyl-3-pyridyl-methyl, methyl-3-pyridyl-ethyl, dimethyl-3-pyridyl-methyl, ethyl-3-pyridyl-methyl, methoxy-3-pyridyl-methyl, methoxy-3-pyridyl-ethyl, dimethoxy-3-pyridyl-methyl, fluoro-3-pyridyl-methyl, difluoro-3-pyridyl-methyl, chloro-3-pyridyl-methyl, chloro-3-pyridyl-ethyl, dichloro-3-pyridyl-methyl, dichloro-3-pyridyl-methyl, bromo-3-pyridyl-methyl, dibromo-3-pyridyl-methyl, 4-pyridyl-methyl, 4-pyridyl-ethyl, 4-pyridyl-propyl, 4-pyridyl-butyl, methyl-4-pyridyl-methyl, methyl-4-pyridyl-ethyl, dimethyl-4-pyridyl-methyl, ethyl-4-pyridyl-methyl, 2-(trifluoromethyl)-4-pyridyl-1-methyl, 3-(trifluoromethyl)-4-pyridyl-1-methyl, 2-(trifluoromethyl)-3-pyridyl-1-methyl, 4-(trifluoromethyl)-3-pyridyl-1-methyl, 3-(trifluoromethyl)-2-pyridyl-1-methyl, 4-(trifluoromethyl)-2-pyridyl-1-methyl, methoxy-4-pyridyl-methyl, methoxy-4-pyridyl-ethyl, dimethoxy-4-pyridyl-methyl, fluoro-4-pyridyl-methyl, difluoro-4-pyridyl-methyl, chloro-4-pyridyl-methyl, chloro-4-pyridyl-ethyl, dichloro-4-pyridyl-methyl, dichloro-4-pyridyl-methyl, bromo-4-pyridyl-methyl, dibromo-4-pyridyl-methyl, phenylmethyl (benzyl), phenylethyl, phenylpropyl, phenylbutyl, 2-methylphenylmethyl, 3-methylphenylmethyl, 4-methylphenylmethyl, 2-methylphenylethyl, 3-methylphenylethyl, 4-methylphenylethyl, 2,3-dimethylphenylmethyl, 2,4-dimethylphenylmethyl, 2,5-dimethylphenylmethyl, 2,6-dimethylphenylmethyl, 3,4-dimethylphenylmethyl, 3,5-dimethylphenylmethyl, 3,6-dimethylphenylmethyl, 2-ethyphenylmethyl, 3-ethylphenylmethyl, 4-ethylphenylmethyl, 2,3-diethylphenylmethyl, 2,4-diethylphenylmethyl, 2,5-diethylphenylmethyl, 2,6-diethylphenylmethyl, 3,4-diethylphenylmethyl, 3,5-diethylphenylmethyl, 3,6-diethylphenylmethyl, 2-trifluoromethyl-phenylmethyl, 3-trifluoromethyl-phenylmethyl, 4-trifluoromethyl-phenylmethyl, 2-trifluoromethyl-phenylethyl, 3-trifluoromethyl-phenylethyl, 4-trifluoromethyl-phenylethyl, 2,3-di-trifluoromethyl-phenylmethyl, 2,4-di-trifluoromethyl-phenylmethyl, 2,5-di-trifluoromethyl- phenylmethyl, 2,6-di-trifluoromethyl- phenylmethyl, 3,4-di-trifluoromethyl-phenylmethyl, 3,5-di-trifluoromethyl-phenylmethyl, 3,6-di-trifluoromethyl-phenylmethyl, 2-methoxy-phenylmethyl, 3-methoxy-phenylmethyl, 4-methoxy-phenylmethyl, 2-methoxy3y-phenylethyl, 3-methoxy-phenylethyl, 4-methoxy-phenylethyl, dimethoxy-phenylmethyl, dimethoxy-phenylethyl, 2,4,6-trimethoxy-phenylmethyl, 2-ethoxy-phenylmethyl, 3-ethoxy-phenylmethyl, 4-ethoxy-phenylmethyl, ethoxy-phenylethyl, diethoxy-phenylmethyl, diethoxy-phenylethyl, 2,4,6-trimethoxy-phenylmethyl, 2-fluorophenylmethyl, 3-fluorophenylmethyl, 4-fluorophenylmethyl, 2,3-difluorophenylmethyl, 2,4-difluorophenylmethyl, 2,5-difluorophenylmethyl, 2,6-difluorophenylmethyl, 3,4-difluorophenylmethyl, 3,5-difluorophenylmethyl, 3,6-difluorophenylmethyl, 2-fluorophenylethyl, 3-fluorophenylethyl or 4-fluorophenylethyl, 2-chlorophenylmethyl, 3-chlorophenylmethyl, 4-chlorophenylmethyl, 2,3-dichlorophenylmethyl, 2,4-dichlorophenylmethyl, 2,5-dichlorophenylmethyl, 2,6-dichlorophenylmethyl, 3,4-dichlorophenylmethyl, 3,5-dichlorophenylmethyl, 3,6-dichlorophenylmethyl, 2-chlorophenylethyl, 3-chlorophenylethyl, 4-chlorophenylethyl, 2-bromophenylmethyl, 3-bromophenylmethyl, 4-bromophenylmethyl, 2,3-dibromophenylmethyl, 2,4-dibromophenylmethyl, 2,5-dibromophenylmethyl, 2,6-dibromophenylmethyl, 3,4-dibromophenylmethyl, 3,5-dibromophenylmethyl, 3,6-dibromophenylmethyl, 2-bromophenylethyl, 3-bromophenylethyl or 4-bromophenylethyl. 2-phenyl-phenylmethyl, 3-phenyl-phenylmethyl, 4-phenyl-phenylmethyl, 2-phenoxy-phenylmethyl, 3-phenoxy-phenylmethyl, 4-phenoxy-phenylmethyl, 2-nitro-phenylmethyl, 3-nitro-phenylmethyl, 4-nitro-phenylmethyl, 2-amino-phenylmethyl, 3-amino-phenylmethyl, 4-amino-phenylmethyl, 2-dimethylamino-phenylmethyl, 3-dimethylamino-phenylmethyl, 4-dimethylamino-phenylmethyl, 2-cyano-phenylmethyl, 3-cyano-phenylmethyl, 4-cyano-phenylmethyl, 2-methanesulfonyl-phenylmethyl, 3-methanesulfonyl-phenylmethyl, 4-methanesulfonyl-phenylmethyl, 2-acid methyl ester-phenylmethyl, 3-acid methyl ester-phenylmethyl, 4-acid methyl ester-phenylmethyl, 2-thiazolyl-methyl, 4-thiazolyl-methyl, 5-thiazolyl-methyl, benzothiophenyl-2-methyl, 4-chloro-benzothiophenyl-2-methyl, 5-chloro-benzothiophenyl-2-methyl, 6-chloro-benzothiophenyl-2-methyl, 7-chloro-benzothiophenyl-2-methyl, benzothiophenyl-3-methyl, 4-chloro-benzothiophenyl-3-methyl, 5-chloro-benzothiophenyl-3-methyl, 6-chloro-benzothiophenyl-3-methyl, 7-chloro-benzothiophenyl-3-methyl, quinolinyl-2-methyl, quinolinyl-3-methyl, quinolinyl-6-methyl, 4-chloro-quinolinyl-6-methyl, 2-(trifiuoromethyl)-quinolinyl-6-methyl, 4-chloro-2-(trifluoromethyl)-quinolinyl-6-methyl, 2-pyrimidyl, 4-pyrimidyl or 2[1,3,5-triazinyl].

Alkyl in $R^1$ is preferably an unsubstituted straight or branched chain hydrocarbon residue containing 1 to 7 carbon atoms as defined above or substituted $C_{1-7}$-alkyl with 1–3 substituents, preferably 1–2 substituents, more preferably 1 substituent selected from heterocyclyl, aryl and cycloalkyl. Alkyl in $R^1$ is more preferable methyl, ethyl, n-propyl, isopropyl, n-butyl, sec-butyl, isobutyl, tert.-butyl, 2-pyridylmethyl, 2-pyridylethyl, 2-pyridylpropyl, 2-pyridylbutyl, 3-pyridylmethyl, 3-pyridylethyl, 3-pyridylpropyl, 3-pyridylbutyl, 4-pyridylmethyl, 4-pyridylethyl, 4-pyridylpropyl, 4-pyridylbutyl, phenylmethyl (benzyl), cyclopropylmethyl, cyclobutylmethyl, cyclopentylmethyl, cyclohexylmethyl, 2-methoxy-phenylmethyl, 3-methoxy-phenylmethyl, 4-methoxy-phenylmethyl, 2,3-dimethoxy-phenylmethyl, 2,4-dimethoxy-phenylmethyl, 2,5-dimethoxy-phenylmethyl, 2,6-dimethoxy-phenylmethyl, 3,4-dimethoxy-phenylmethyl, 3,5-dimethoxy-phenylmethyl, 2,4,6-trimethoxy-phenylmethyl, 2-thiazolyl-methyl, 4-thiazolyl-methyl, 5-thiazolyl-methyl, benzothiophenyl-2-methyl, 4-chloro-benzothiophenyl-2-methyl, 5-chloro-benzothiophenyl-2-methyl, 6-chloro-benzothiophenyl-2-methyl, 7-chloro-benzothiophenyl-2-methyl, benzothiophenyl-3-methyl, 4-chloro-benzothiophenyl-3-methyl, 5-chloro-benzothiophenyl-3-methyl, 6-chlorobenzothiophenyl-3-methyl, 7-chloro-benzothiophenyl-3-methyl, quinolinyl-2-methyl, quinolinyl-3-methyl, quinolinyl-6-methyl, 4-chloro-quinolinyl-6-methyl, 2-(trifluoromethyl)-quinolinyl-6-methyl or 4-chloro-2-(trifluoromethyl)-quinolinyl-6-methyl, 2-(trifluoromethyl)-4-pyridyl-1-methyl, 3-(trifluoromethyl)-4-pyridyl-1-methyl, 2-(trifluoromethyl)-3-pyridyl-1-methyl, 4-(trifluoromethyl)-3-pyridyl-1-methyl, 3-(trifluoromethyl)-2-pyridyl-1-methyl, 4-(trifluoromethyl)-2-pyridyl-1-methyl or N-benzylamidomethyl. Further preferred alkyl substituents for $R^1$ are methyl, ethyl, isopropyl, cyclohexylmethyl, phenylmethyl or pyridylmethyl. Most preferred alkyl substituent for $R^1$ is 4-pyridylmethyl.

Alkyl in $R^2$ is preferably an unsubstituted straight or branched chain hydrocarbon residue containing 1 to 7 carbon atoms as defined above, more preferable methyl, ethyl, n-propyl, isopropyl, n-butyl, sec-butyl, isobutyl or tert.-butyl. Further preferred alkyl substituents for $R^2$ are methyl or n-propyl. Most preferred alkyl in $R^2$ is methyl.

Alkyl in $R^3$ is preferably an unsubstituted straight or branched chain hydrocarbon residue containing 1 to 7 carbon atoms as defined above or substituted $C_{1-7}$-alkyl with 1–3 substituents, preferably 1–2 substituents, more preferably 1 substituent selected from heterocyclyl. More preferable alkyl in $R^3$ is methyl, ethyl, n-propyl, isopropyl, n-butyl, sec-butyl, isobutyl, tert.-butyl, 2-pyridylmethyl, 2-pyridylethyl, 3-pyridylmethyl, 3-pyridylethyl, 4-pyridylmethyl, 4-pyridylethyl. Further preferred alkyl substituents for $R^3$ are isopropyl, n-propyl or pyridylmethyl. Most preferred alkyl in $R^3$ is isopropyl. Alkyl in $R^3$ is not $CF_3$.

Alkyl in $R^4$ is preferably an unsubstituted straight or branched chain hydrocarbon residue containing 1 to 7 carbon atoms as defined above or substituted $C_{1-7}$-alkyl (preferably $C_{1-2}$-alkyl) with 1–3 substituents, preferably 1–2 substituents, more preferably 1 substituent selected from hydroxy, amino, $C_{1-4}$-alkoxy (preferably, $C_{1-2}$-alkoxy), phenyl, methyl-oxy-carbonyl, ethyl-oxy-carbonyl, azido, 2-pyridyl-carbonyl-amino, 3-pyridyl-carbonyl-amino, 4-pyridyl-carbonyl-amino, (phenoxy)-carbonyl-amino, (methoxy)-carbonyl-amino, (di-methyl-amino)-carbonyl-amino, (phenyl-amino)-carbonyl-amino, (amino)-carbonyl-amino, (phenyl)-carbonyl-amino, (methyl)-carbonyl-amino, methyl-carbonyl-amino-methyl-carbonyl-amino, (tert.-butyl)-carbonyl-amino-methyl-carbonyl-amino, methyl-sulfonyl-amino, phenyl-sulfonyl-amino, p-toluyl-sulfonyl-amino, (N1-acetyl-O-tert.-butyl-N2-yl)-L-serinamide, (N1-acetyl-N2-yl)-L-serinamide and [N1-(tert.-butoxycarbonyl)-O-tert.-butyl-N2-yl]-L-serinamide. More preferred substituents for $C_{1-7}$-alkyl (preferably $C_{1-2}$-alkyl) are selected from hydroxy, amino, $C_{1-2}$-alkoxy, 2-pyridyl-carbonyl-amino, 3-pyridyl-carbonyl-amino, 4-pyridyl-carbonyl-amino, (phenoxy)-carbonyl-amino, (methoxy)-carbonyl-amino, (di-methyl-amino)-carbonyl-amino, (phenyl-amino)-carbonyl-amino, (amino)-carbonyl-amino, (phenyl)-carbonyl-amino, (methyl)-carbonyl-amino, methyl-carbonyl-amino-methyl-carbonyl-amino, (tert.-butyl)-carbonyl-amino-methyl-carbonyl-amino, (N1-acetyl-O-tert.-butyl-N2-yl)-L-serinamide, (N1-acetyl-N2-yl)-L-serinamide and [N1-(tert.-butoxycarbonyl)-O-tert.-butyl-N2-yl]-L-serinamide. Most preferred substituents for $C_{1-7}$-alkyl (preferably $C_{1-2}$-alkyl) are selected from hydroxy, 2-pyridyl-carbonyl-amino, 3-pyridyl-carbonyl-amino, 4-pyridyl-carbonyl-amino, (phenoxy)-carbonyl-amino, (methoxy)-carbonyl-amino, (di-methyl-amino)-carbonyl-amino, (phenyl-amino)-carbonyl-amino, (amino)-carbonyl-amino, (phenyl)-carbonyl-amino, (methyl)-carbonyl-amino, methyl-carbonyl-amino-methyl-carbonyl-amino, (tert.-butyl)-carbonyl-amino-methyl-carbonyl-amino, (N1-acetyl-O-tert.-butyl-N2-yl)-L-serinamide, (N1-acetyl-N2-yl)-L-serinamide and [N1-(tert.-butoxycarbonyl)-O-tert.-butyl-N2-yl]-L-serinamide. In case more than one substituent is attached to the alkyl group, these substituents can be identical or different from each other. Alkyl in $R^4$ is more preferable methyl, ethyl, n-propyl, isopropyl, n-butyl, sec-butyl, isobutyl, tert.-butyl, hydroxy-methyl, 1-hydroxy-ethyl, 2-hydroxy-ethyl, 1,2-ethanediol, 1,2-propanediol, amino-methyl, amino-ethyl, methoxy-methyl, methoxy-ethyl, phenyl-methanol, (methyl-oxy-carbonyl)-(hydroxy-methyl), (ethyl-oxy-carbonyl)-(hydroxy-methyl), azido-methyl, azido-ethyl, 2-pyridyl-carbonyl-amino-methyl, 3-pyridyl-carbonyl-amino-methyl, 4-pyridyl-carbonyl-amino-methyl, (amino-methyl)-carbonyl-amino-methyl, (phenoxy)-carbonyl-amino-methyl, (methoxy)-carbonyl-amino-methyl, (di-methyl-amino)-carbonyl-amino-methyl, (phenyl-amino)-carbonyl-amino-methyl, (amino)-carbonyl-amino-methyl, (phenyl)-carbonyl-amino-methyl, (methyl)-carbonyl-amino-methyl, methyl-carbonyl-amino-methyl-carbonyl-amino-methyl, (tert.-butyl)-carbonyl-amino-methyl-carbonyl-amino-methyl, (N1-acetyl-O-tert.-butyl-N2-ylmethyl)-L-serinamide, (N1-acetyl-N2-yl]methyl)-L-serinamide, [N1-(tert.-butoxycarbonyl)-O-tert.-butyl-N2-yl-methyl]-L-serinamide, methyl-sulfonyl-amino-methyl, phenyl-sulfonyl-amino-methyl or p-toluyl-sulfonyl-amino-methyl. Preferred alkyl for $R^4$ is unsubstituted $C_{1-7}$-alkyl (preferably $C_{1-4}$-alkyl) or substituted $C_{1-7}$-alkyl (preferably $C_{1-4}$-alkyl, more preferred $C_{1-2}$-alkyl) with hydroxy or amino or methoxy as substituents. More preferable alkyl in $R^4$ is methyl or ethyl substituted with a hydroxy group or a methoxy group or (methyl)-carbonyl-amino-methyl. Further preferred alkyl groups for $R^4$ are methyl or ethyl substituted with a hydroxy group or a methoxy. More preferred alkyl in $R^4$ is methyl substituted with a hydroxy group or (methyl)-carbonyl-amino-methyl. Most preferred alkyl in $R^4$ is methyl substituted with a hydroxy group.

Alkyl in $R^5$ is preferably an unsubstituted straight or branched chain hydrocarbon residue containing 1 to 7 carbon atoms (preferably, $C_{1-4}$-alkyl), as defined above or substituted $C_{1-7}$-alkyl (preferably $C_{1-4}$-alkyl, more preferred $C_{1-2}$-alkyl) with 1–3 substituents, preferably 1–2 substituents, more preferably 1 substituent selected from hydroxy, $C_{1-4}$-alkoxy (preferably methoxy or ethoxy), methyl-carbonyl-oxy or amino-carbonyl-oxy. Alkyl in $R^5$ is more preferable methyl, ethyl, n-propyl, isopropyl, n-butyl, sec-butyl, isobutyl, tert.-butyl, hydroxy-methyl, 1-hydroxy-ethyl, 2-hydroxy-ethyl, 1,2-ethanediol, 1,2-propanediol, methoxy-methyl, ethoxy-methyl, (methyl-carbonyl-oxy)-methyl, (amino-carbonyl-oxy)-methyl. More preferable alkyl in $R^5$ is methyl, ethyl, n-propyl, isopropyl or substituted $C_{1-2}$-alkyl substituted with 1–3 substituents selected from hydroxy, methyl-carbonyl-oxy and amino-carbonyl-oxy. Further preferred alkyl in $R^5$ is methyl, ethyl, (amino-carbonyl-oxy)-methyl or $C_{1-2}$-alkyl substituted with a hydroxy group. Another preferred alkyl in $R^5$ is methyl or (amino-carbonyl-oxy)-methyl, most preferred alkyl in $R^5$ is methyl.

In another preferred embodiment of the invention, alkyl in $R^5$ is unsubstituted alkyl or substituted alkyl with hydroxy as substituent, more preferably wherein alkyl in $R^5$ is methyl or ethyl optionally substituted with a hydroxy group, and most preferred wherein alkyl in $R^5$ is methyl.

Alkyl in R, R', R" and R'" is preferably an unsubstituted straight or branched chain hydrocarbon residue containing 1 to 7 carbon atoms as defined above and more preferably methyl, ethyl, n-propyl, isopropyl, n-butyl, sec-butyl, isobutyl, tert.-butyl.

Alkyl for N(alkyl) is preferably an unsubstituted straight or branched chain hydrocarbon residue containing 1 to 7 carbon atoms and most preferred methyl.

The term "cycloalkyl" as used herein, and if not specified by the number of carbon atoms, denotes an optionally substituted cycloalkyl group containing 3 to 8 carbon atoms, e.g. cyclopropyl, cydobutyl, cyclopentyl, cyclohexyl, cycloheptyl or cyclooctyl. The term "cycloalkyl" preferably denotes a cycloalkyl group containing 3 to 6 carbon atoms.

Suitable substituents for cycloalkyl can be selected from those named for alkyl, in addition however an oxo group (=O) can be added to the selection.

Cycloalkyl in $R^1$ and $R^2$ are as defined above.

Cycloalkyl in $R^3$ denotes an optionally substituted cycloalkyl group containing 3 to 8 carbon atoms, preferably 3 to 6 carbon atoms. Most preferred cycloalkyl in $R^3$ denotes a cyclopropyl group.

The term "alkoxy" as used herein, and if not otherwise specified by the number of carbon atoms, denotes a straight or branched chain alkyl-oxy group wherein the "alkyl" portion is as defined above such as methoxy, ethoxy, n-propyloxy, isopropyloxy, n-butyloxy, isobutyloxy, tert.-butyloxy, pentyloxy, hexyloxy, heptyloxy including their different isomers. More preferred alkoxy groups within the invention are methoxy, ethoxy, n-propyloxy, isopropyloxy, n-butyloxy, isobutyloxy or tert.-butyloxy.

Alkoxy in R is as defined above.

The term "alkenyl" as used herein, and if not specified by the number of carbon atoms, denotes an unsubstituted or substituted hydrocarbon chain radical having from 2 to 8 carbon atoms, preferably from 2 to 4 carbon atoms, and having at least one olefinic double bond, including their different isomers. Examples are vinyl or allyl.

Alkenyl in $R^4$ is as defined above.

The term "C(=O)R," as used herein for $R^4$, denotes a hydrogen atom, an $C_{1-7}$-alkyl group (preferably $C_{1-4}$-alkyl as defined above for the alkyl substituent R), alkoxy (preferably $C_{1-4}$-alkoxy), trifluoromethyl, methyl-oxy-carbonyl, ethyl-oxy-carbonyl, each of these substituents attached to a keto function —C(=O)—. Preferred examples are an aldehyde group (C(=O)H), methyl-carbonyl, ethyl-carbonyl, tert.-butoxy-carbonyl, trifluoromethyl-carbonyl, methyl-oxy-dicarbonyl or ethyl-oxy-carbonyl.

The term "CONR'R''' " as used herein for $R^4$, denotes, independently of each other, hydrogen, $C_{1-7}$-alkyl (preferably $C_{1-4}$-alkyl), substituted aryl (preferably phenyl), each of these substituents attached to a amino-carbonyl function. Preferred examples are amino-carbonyl ($CONH_2$), (methyl-amino)-carbonyl, (dimethyl-amino)-carbonyl, (phenyl-amino)-carbonyl or (2, 4, 6-trimethoxy-methyl)-amino-carbonyl.

The term "—Z—C(=O)R'" " as used herein for $R^5$, wherein Z is a single bond or —CH=CH— and R''' is hydrogen or alkyl (preferably $C_{1-4}$-alkyl) denotes an aldehyde group (C(=O)H), methyl-carbonyl or ethyl-carbonyl, aldehyde-ethylene (—CH=CH)C(=O)H), (methyl-carbonyl)-ethylene (—CH=CH)C(=O) $CH_3$) or (ethyl-carbonyl)-ethylene (—CH=CH)C(=O)$C_2H_5$). The ethylene group of the invention can have the (E) or (Z) configuration. Both isomeric forms of these compounds are embraced by the present invention.

The term "aryl" as used herein denotes an optionally substituted phenyl and naphthyl, both optionally benz-fused to an optionally substituted saturated, partially unsaturated or aromatic monocyclic, bicyclic or tricyclic heterocycle or carbocycle e.g. to cyclohexyl or cyclopentyl.

Suitable substituents for aryl can be selected from those named for alkyl, in addition however $C_{1-4}$-alkyl, trifluoromethyl, trifluoromethoxy, $C_{2-4}$-alkenyl, 1,2-propanediol, cyano and hydroxy-methyl can be added to the selection.

In case more than one substituent is attached to the aryl group, these substituents can be identical or different from each other.

Aryl in $R^1$ is preferably an unsubstituted or substituted phenyl with suitable substituents selected from 1 to 5 of halogen, nitro and unsubstituted straight or branched chain alkyl containing 1 to 4 carbon atoms.

Aryl in $R^2$ is preferably an unsubstituted or substituted phenyl or naphthyl (preferably phenyl) with suitable substituents selected from 1 to 5 substituents, preferably 1–4 substituents, more preferably 1–3 substituent selected from $C_{1-7}$-alkyl (preferable $C_{1-4}$-alkyl), trifluoromethyl, $C_{1-4}$-alkoxy (preferable $C_{1-2}$-alkoxy), trifluoromethoxy, $C_{2-4}$-alkenyl, 1,2-propanediol, fluorine, chlorine, bromine, iodine, nitro, cyano, phenyl, hydroxy-methyl, 4-pyridyl, 3-pyridyl and 2-pyridyl (preferably 1–3 substituent selected from $C_{1-7}$-alkyl (preferable $C_{1-4}$-alkyl), halogen and nitro; more preferably 1–3 substituent selected from halogen; most preferably 1–3 substituent selected from chlorine). In case more than one substituent is attached to the aryl group, these substituents can be identical or different from each other. Examples of substituted aryl groups are 2-methyl-phenyl, 3-methyl-phenyl, 4-methyl-phenyl, 2-ethyl-phenyl, 3-ethyl-phenyl, 4-ethyl-phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,6-dimethylphenyl, 2,4,6-trimethylphenyl, 3,4,5-trimethylphenyl, 2,3,4-trimethylphenyl, 2,4,5-trimethylphenyl, 2-methoxy-phenyl, 3-methoxy-phenyl, 4-methoxy-phenyl, 2,3-dimethoxy-phenyl, 2,4-dimethoxy-phenyl, 2,5-dimethoxy-phenyl, 2,6-dimethoxy-phenyl, 3,4-dimethoxy-phenyl, 3,5-dimethoxy-phenyl, 3,6-dimethoxy-phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 3,6-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 3,6-dichlorophenyl, 2,4,6-trichlorophenyl, 3,4,5-trichlorophenyl, 2,3,4-trichlorophenyl, 2,4,5-trichlorophenyl, 2-bromophenyl, 3-bromophenyl, 4-bromophenyl, 2,3-dibromophenyl, 2,4-dibromophenyl, 2,5-dibromophenyl, 2,6-dibromophenyl, 3,4-dibromophenyl, 3,5-dibromophenyl, 3,6-dibromophenyl, 2-trifluoromethyl-phenyl, 3-trifluoromethyl-phenyl, 4-trifluoromethyl-phenyl, 2-cyano-phenyl, 3-cyano-phenyl, 4-cyano-phenyl, 2,3-di-cyano-phenyl, 2,4-di-cyano-phenyl, 2,5-di-cyano-phenyl, 2,6-di-cyano-phenyl, 3,4-di-cyano-phenyl, 3,5-di-cyano-phenyl, 3,6-di-cyano-phenyl, 2-nitro-phenyl, 3-nitro-phenyl, 4-nitro-phenyl, 2-(trifluoromethoxy)phenyl, 3-(trifluoromethoxy)phenyl, 4-(trifluoromethoxy)phenyl, 2-(phenyl)phenyl, 3-(phenyl)phenyl, 4-(phenyl)phenyl, 2-(hydroxymethyl)phenyl, 3-(hydroxymethyl)phenyl, 4-(hydroxymethyl)phenyl, 2-(2-pyridyl)phenyl, 3-(2-pyridyl)phenyl, 4-(2-pyridyl)phenyl, 2-(3-pyridyl)phenyl, 3-(3-pyridyl)phenyl, 4-(3-pyridyl)phenyl, 2-(4-pyridyl) phenyl, 3-(4-pyridyl)phenyl, 4-(4-pyridyl)phenyl, 2-chloro-4-fluorophenyl, 2-chloro-6-methyl-phenyl, 3-chloro-5-bromo-phenyl, 3-chloro-5-propyl-phenyl, 3-chloro-5-methyl-phenyl, 3-chloro-5-ethyl-phenyl, 3-chloro-5-vinyl-phenyl, 3-chloro-5-allyl-phenyl, 3-chloro-5-phenyl-phenyl, 3-chloro-5-(hydroxymethyl)-phenyl, 3-chloro-5-cyano-phenyl, 3-chloro-5-(1,2-propanediol)-phenyl, 2-naphthyl or 3-cyano-5-methyl. Preferred example for aryl in $R^2$ is 3,5-dichlorophenyl.

Aryl in $R^3$ is preferably an unsubstituted or substituted phenyl with suitable substituents selected from 1 to 5 substituents, preferably 1–4 substituents, more preferably 1–3 substituent selected from $C_{1-4}$-alkyl (preferable $C_{1-2}$-alkyl), $C_{1-4}$-alkoxy (preferable $C_{1-2}$-alkoxy), fluorine, chlorine, bromine, iodine and phenyl (preferably 1–3 substituent selected from $C_{1-4}$-alkyl (preferable $C_{1-2}$-alkyl), $C_{1-4}$-alkoxy (preferable $C_{1-2}$-alkoxy) and halogen; more preferably 1–3 substituent selected from $C_{1-4}$-alkyl (preferable $C_{1-2}$-alkyl) and $C_{1-4}$-alkoxy (preferable $C_{1-2}$-alkoxy). Examples of substituted aryl groups are 2-methyl-phenyl, 3-methyl-phenyl, 4-methyl-phenyl, 2-methoxy-phenyl, 3-methoxy-phenyl, 4-methoxy-phenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl or 3,6-dichlorophenyl. Most preferred aryl in $R^3$ is phenyl.

Aryl in $R^5$, R' and R" is as defined above, preferably phenyl.

The term "heterocyclyl" as used herein denotes an optionally substituted saturated, partially unsaturated or aromatic monocyclic or bicyclic heterocycle which contains 1 to 4 hetero atoms selected from nitrogen, oxygen and sulfur which can also be fused to an optionally substituted saturated, partially unsaturated or aromatic monocyclic carbocycle or heterocycle.

Examples of suitable heterocycles are oxazolyl, isoxazolyl, furyl, tetrahydrofuryl, 1,3-dioxolanyl, dihydropyranyl, thienyl, pyrazinyl, isothiazolyl, isoquinolinyl, indolyl, indazolyl, quinolinyl, dihydrooxazolyl, pyrimidinyl, benzofuranyl, tetrazolyl, pyrrolidinyl, pyrrolidinonyl, (N-oxide)-pyridinyl, pyrrolyl, triazolyl e.g. 1,2,4-triazolyl, pyrazolyl, benzotriazolyl, piperidinyl, morpholinyl, thiazolyl, pyridyl, dihydrothiazolyl, imidazolidinyl, pyrazolinyl, benzothienyl, piperazinyl, imidazolyl, thiadiazolyl e.g. 1,2,3-thiadiazolyl, and benzothiazolyl. Most preferred example is pyridyl.

Heterocyclyl in $R^1$, $R^2$ and $R^3$ is preferably an unsubstituted or substituted pyridyl with suitable substituents selected from 1 to 5 of halogen, nitro and unsubstituted straight or branched chain alkyl containing 1 to 4 carbon atoms.

Suitable substituents for heterocyclyl can be selected from those named for alkyl, in addition however an oxo group (=O) as substituent can be added to the selection.

The term "C(=O)R" as used herein denotes an carbonyl group to which is attached a substituent selected from hydrogen, alkyl, alkoxy, trifluoromethyl, methyl-oxy-carbonyl and ethyl-oxy-carbonyl (preferably hydrogen or alkyl). Examples for suitable substituents for the carbonyl group are hydrogen, tert.-butoxy, trifluoromethyl, methyl, ethyl-oxy-carbonyl. In an other embodiment of the invention preferred acyl groups are those wherein R is hydrogen or an unsubstituted straight or branched chain hydrocarbon residue containing 1 to 7 carbon atoms.

The term "CONR'R" " as used herein denotes amides wherein R' and R" are each independently selected from hydrogen, alkyl or aryl (preferably hydrogen or $C_{1-7}$-alkyl (preferable $C_{1-4}$-alkyl)). Examples for suitable substituents for the amide group (R' and/or R") are hydrogen, $C_{1-4}$-alkyl (preferably methyl), phenyl, 2,4,6-trimethoxy-benzyl.

The term "X" represents S, S(O), S(O)$_2$, O, N(alkyl) or X—$R^2$ together represent $CH_2$-aryl (preferably $CH_2$-phenyl) or $CH_2$-heterocyclyl (preferably $CH_2$-(4)-pyridyl, $CH_2$-(3)-pyridyl, $CH_2$-(2)-pyridyl), more preferable S, S(O), S(O)$_2$, O, N(alkyl). Most preferably, "X" is S.

The term halogen stands for fluorine, chlorine, bromine and iodine, most preferably chlorine.

Any functional (i.e. reactive) group present in a side-chain may be protected, with the protecting group being a group which is known to one skilled in the art, for example, as described in "Protective Groups in Organic Synthesis", 2$^{nd}$ Ed., T. W. Greene and P. G. M. Wuts, John Wiley & Sons, New York, N.Y., 1991. For example, an amino group can be protected by tert.-butoxycarbonyl (BOC) or benzyloxycarbonyl (Z).

The compounds of this invention may contain one or more asymmetric carbon atoms and may therefore occur as racemates and racemic mixtures, single enantiomers, diastereomeric mixtures and individual diastereomers. Furthermore, where a compound of the invention contains an olefinic double bond, this can have the (E) or (Z) configuration. Also, each chiral center may be of the R or S configuration. All such isomeric forms of these compounds are embraced by the present invention.

Compounds of formula I which are acidic can form pharmaceutically acceptable salts with bases such as alkali metal hydroxides, e.g. sodium hydroxide and potassium hydroxide; alkaline earth metal hydroxides, e.g. calcium hydroxide, barium hydroxide and magnesium hydroxide, and the like; with organic bases e.g. N-ethyl piperidine, dibenzylamine, and the like. Those compounds of formula (I) which are basic can form pharmaceutically acceptable salts with inorganic acids, e.g. with hydrohalic acids such as hydrochloric acid and hydrobromic acid, sulphuric acid, nitric acid and phosphoric acid, and the like, and with organic acids, e.g. with acetic acid, tartaric acid, succinic acid, fumaric acid, maleic acid, malic acid, salicylic acid, citric acid, methanesulphonic acid and p-toluene sulphonic acid, and the like. The formation and isolation of such salts can be carried out according to methods known in the art.

A preferred embodiment of the invention are compounds of formula I wherein $R^1$ is alkyl,
preferably wherein
  $R^1$ is $C_{1-7}$ alkyl or $C_{1-7}$ alkyl substituted with 1–3 substituents selected from cycloalkyl, aryl and heterocyclyl,
more preferably wherein
  $R^1$ is methyl, ethyl, isopropyl, cyclohexylmethyl, phenylmethyl, pyridylmethyl,
most preferably wherein
  $R^1$ is 4-pyridylmethyl;
$R^2$ is alkyl or aryl,
preferably wherein
  $R^2$ is $C_{1-7}$ alkyl, phenyl or phenyl substituted with 1–5 substituents selected from $C_{1-7}$ alkyl, halogen and nitro,
more preferably wherein
  $R^2$ is methyl, n-propyl or phenyl substituted with 1–5 chlorine atoms,
most preferably wherein
  $R^2$ is methyl or 3,5-dichlorophenyl;
$R^3$ is alkyl, cycloalkyl or aryl,
preferably wherein
  $R^3$ is $C_{1-7}$ alkyl, $C_{1-7}$ alkyl substituted with 1–3 heterocyclyl, phenyl or phenyl substituted with 1–5 substituents selected from $C_{1-4}$-alkyl, $C_{1-4}$-alkoxy and halogen;

more preferably wherein
R³ is isopropyl, n-propyl or pyridylmethyl,
most preferably wherein
R³ is isopropyl;
R⁴ is hydrogen, alkyl, carboxyl, C(=O)R, CONR'R'', cyano or alkenyl, wherein
R is hydrogen, alkyl, alkoxy, trifluoromethyl, methyl-oxy-carbonyl or ethyl-oxy-carbonyl,
wherein
R' and R'', are independently of each other, hydrogen, alkyl or aryl, preferably wherein
R⁴ is hydrogen, $C_{1-7}$ alkyl or $C_{1-7}$ alkyl substituted with 1–3 substituents selected from hydroxy, amino, $C_{1-4}$-alkoxy, phenyl, methyl-oxy-carbonyl, ethyl-oxy-carbonyl, azido, 2-pyridyl-carbonyl-amino, 3-pyridyl-carbonyl-amino, 4-pyridyl-carbonyl-amino, (phenoxy)-carbonyl-amino, (methoxy)-carbonyl-amino, (di-methyl-amino)-carbonyl-amino, (phenyl-amino)-carbonyl-amino, (amino)-carbonyl-amino, (phenyl)-carbonyl-amino, (methyl)-carbonyl-amino, methyl-carbonyl-amino-methyl-carbonyl-amino, (tert.-butyl)-carbonyl-amino-methyl-carbonyl-amino, methyl-sulfonyl-amino, phenyl-sulfonyl-amino, p-toluyl-sulfonyl-amino, (N1-acetyl-O-tert.-butyl-N2-yl)-L-serinamide, (N1-acetyl-N2-yl)-L-serinamide and [N1-(tert.-butoxycarbonyl)-O-tert.-butyl-N2-yl]-L-serinamide,
more preferably wherein
R⁴ is hydrogen or $C_{1-2}$ alkyl substituted with 1–3 substituents selected from hydroxy, amino, $C_{1-2}$-alkoxy, 2-pyridyl-carbonyl-amino, 3-pyridyl-carbonyl-amino, 4-pyridyl-carbonyl-amino, (phenoxy)-carbonyl-amino, (methoxy)-carbonyl-amino, (di-methyl-amino)-carbonyl-amino, (phenyl-amino)-carbonyl-amino, (amino)-carbonyl-amino, (phenyl)-carbonyl-amino, (methyl)-carbonyl-amino, methyl-carbonyl-amino-methyl-carbonyl-amino, (tert.-butyl)-carbonyl-amino-methyl-carbonyl-amino, (N1-acetyl-O-tert.-butyl-N2-yl)-L-serinamide, (N1-acetyl-N2-yl)-L-serinamide and [N1-(tert.-butoxycarbonyl)-O-tert.-butyl-N2-yl]-L-serinamide,
most preferably wherein
R⁴ is $C_{1-2}$ alkyl substituted with 1–2 substituents selected from hydroxy, 2-pyridyl-carbonyl-amino, 3-pyridyl-carbonyl-amino, 4-pyridyl-carbonyl-amino, (phenoxy)-carbonyl-amino, (methoxy)-carbonyl-amino, (di-methyl-amino)-carbonyl-amino, (phenyl-amino)-carbonyl-amino, (amino)-carbonyl-amino, (phenyl)-carbonyl-amino, (methyl)-carbonyl-amino, methyl-carbonyl-amino-methyl-carbonyl-amino, (tert.-butyl)-carbonyl-amino-methyl-carbonyl-amino, (N1-acetyl-O-tert.-butyl-N2-yl)-L-serinamide, (N1-acetyl-N2-yl)-L-serinamide and [N1-(tert.-butoxycarbonyl)-O-tert.-butyl-N2-yl]-L-serinamide;
R⁵ is alkyl, aryl or a group —Z—C(=O)R''', wherein
Z is a single bond or —CH=CH—, and
R''' is hydrogen or alkyl, preferably wherein
R⁵ is $C_{1-7}$ alkyl, phenyl, $C_{1-7}$ alkyl substituted with 1–3 substituents selected from hydroxy, $C_{1-4}$-alkoxy, methyl-carbonyl-oxy and amino-carbonyl-oxy,
more preferably wherein
R⁵ is methyl, ethyl, n-propyl, isopropyl, n-butyl, sec-butyl, isobutyl, tert.-butyl or $C_{1-2}$-alkyl substituted with 1–3 substituents selected from hydroxy, $C_{1-2}$-alkoxy, methyl-carbonyl-oxy and amino-carbonyl-oxy, most preferably wherein
R⁵ is methyl, ethyl, n-propyl, isopropyl or $C_{1-2}$-alkyl substituted with 1–3 substituents selected from hydroxy, methyl-carbonyl-oxy and amino-carbonyl-oxy;
X represents S, O, N(alkyl) or X—R² together represent $CH_2$-aryl or $CH_2$-heterocyclyl; and with the proviso that alkyl in R³ is not $CF_3$,
preferably wherein
X represents S.
Other preferred embodiments of the invention are compounds of formula I

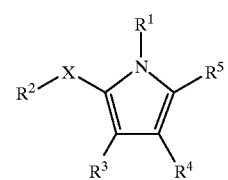

wherein
R¹ is alkyl, cycloalkyl, aryl or heterocyclyl,
preferably wherein
R¹ is alkyl,
more preferably wherein
R¹ is alkyl substituted with heterocyclyl or aryl, unsubstituted $C_{1-7}$ alkyl or alkyl substituted with cycloalkyl,
most preferably wherein
R¹ is pyridylmethyl, phenylmethyl, methyl, ethyl, isopropyl, cyclohexylmethyl;
R² is alkyl, cycloalkyl, aryl or heterocyclyl,
preferably wherein
R² is alkyl or aryl,
more preferably wherein
R² is unsubstituted alkyl, unsubstituted phenyl or substituted phenyl with 1 to 5 halogen or nitro or unsubstituted $C_{1-7}$ alkyl as substituents,
most preferably wherein
R² is methyl, n-propyl or chlorinated phenyl;
R³ is hydrogen, alkyl, cycloalkyl, aryl or heterocyclyl,
preferably wherein
R³ is alkyl or aryl,
more preferably wherein
R³ is unsubstituted alkyl or substituted alkyl with heterocyclyl as substituent, unsubstituted phenyl or substituted phenyl with 1 to 5 halogen or methoxy or unsubstituted alkyl as substituents,
most preferably wherein
R³ is isopropyl, n-propyl or pyridylmethyl;
R⁴ is hydrogen, alkyl, carboxyl, C(=O)R or $CONR_2$ wherein
R is hydrogen or alkyl, preferably wherein
R⁴ is hydrogen, alkyl, carboxyl, C(=O)R or $CONR_2$,
more preferably wherein
R⁴ is hydrogen, unsubstituted alkyl or substituted alkyl with hydroxy or amino or methoxy as substituents, carboxyl, C(=O)R, $CONR_2$,
most preferably wherein
R⁴ is methyl or ethyl with hydroxy or methoxy as substituents, carboxyl, C(=O)R, $CONR_2$;
R⁵ is hydrogen or alkyl,
preferably wherein
R⁵ is hydrogen, unsubstituted alkyl or substituted alkyl with hydroxy as substituent, more preferably wherein R⁵ is methyl or ethyl optionally substituted with a hydroxy group;

X represents S, S(O), S(O)₂, O, N(alkyl) or X—R² together represent CH₂-aryl or CH₂-heterocyclyl; and with the proviso that only one of R³, R⁴ and R⁵ is hydrogen and alkyl in R³ is not CF₃, preferably wherein X represents S, S(O), S(O)₂, O, N(alkyl), more preferably wherein X represents S; and hydrolyzable esters or ethers thereof or a pharmaceutically acceptable salt thereof.

Other preferred embodiments of the invention are compounds of formula I wherein

R¹ is 4-pyridyl methyl;

R² is methyl or 3,5-dichlorophenyl;

R³ is isopropyl;

R⁴ is methyl substituted with a hydroxy group or C(=O) R;

R⁵ is methyl; and

X represents S.

Additional preferred embodiments of compounds of formula I, as well as hydrolyzable esters or ethers thereof or a pharmaceutically acceptable salt thereof, are listed in table 1 below.

TABLE 1

| STRUCTURE | SYSTEMATIC NAME |
|---|---|
| 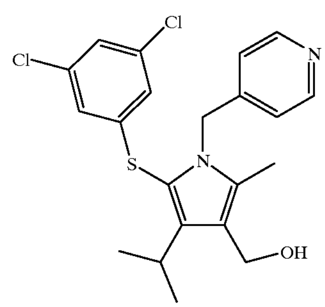 | 5-(3,5-Dichlorophenylthio)-4-isopropyl-2-methyl-1-[(4-pyridyl)methyl]-1H-pyrrole-3-methanol |
| 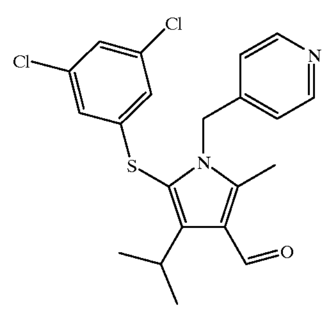 | 5-(3,5-Dichlorophenylthio)-4-isopropyl-2-methyl-1-[(4-pyridyl)methyl]-1H-pyrrole-3-carboxaldehyde |
| 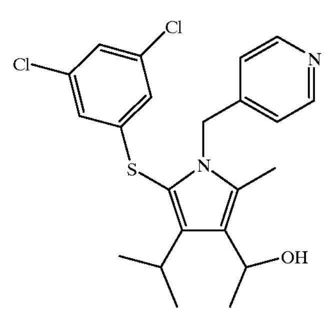 | 5-(3,5-Dichlorophenylthio)-4-isopropyl-alpha(RS)-methyl-1-[(4-pyridyl)methyl]-1H-pyrrole-3-ethanol |

TABLE 1-continued

| STRUCTURE | SYSTEMATIC NAME |
|---|---|
| 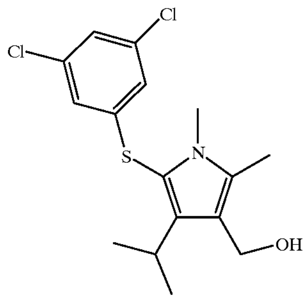 | 5-(3,5-Dichlorophenylthio)-4-isopropyl-1,2-dimethyl-1H-pyrrole-3-methanol |
| 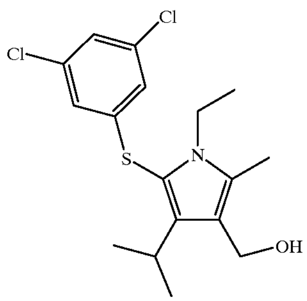 | 5-(3,5-Dichlorophenylthio)-1-ethyl-4-isopropyl-2-methyl-1H-pyrrole-3-methanol |
| 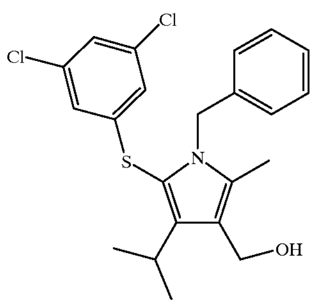 | 1-Benzyl-5-(3,5-dichlorophenylthio)-4-isopropyl-2-methyl-1H-pyrrole-3-methanol |
| 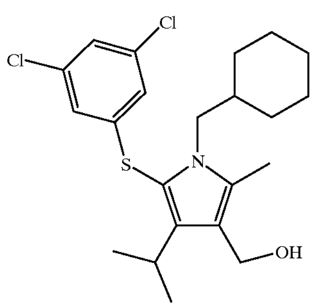 | 1-(Cyclohexylmethyl)-5-(3,5-dichlorophenylthio)-4-isopropyl-2-methyl-1H-pyrrole-3-methanol |
| 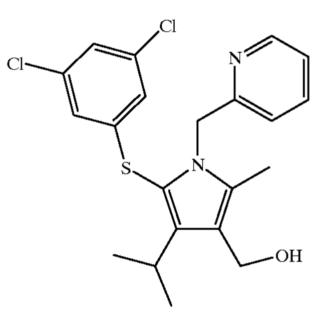 | 5-(3,5-Dichlorophenylthio)-4-isopropyl-2-methyl-1-[(2-pyridyl)methyl]-1H-pyrrole-3-methanol |

TABLE 1-continued

| STRUCTURE | SYSTEMATIC NAME |
|---|---|
| 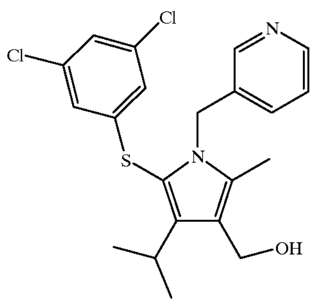 | 5-(3,5-Dichlorophenylthio)-4-isopropyl-2-methyl-1-[(3-pyridyl)methyl]-1H-pyrrole-3-methanol |
| 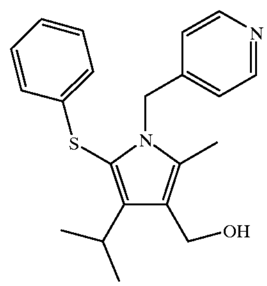 | 4-Iospropyl-2-methyl-5-phenylthio-1-[(4-pyridyl)methyl]-1H-pyrrole-3-methanol |
| 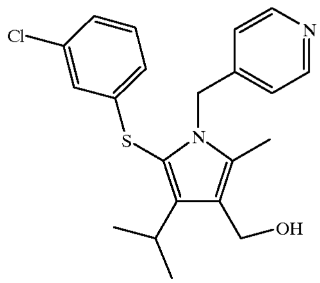 | 5-(3-Chlorophenylthio)-4-isopropyl-2-methyl-1-[(4-pyridyl)methyl]-1H-pyrrole-3-methanol |
| 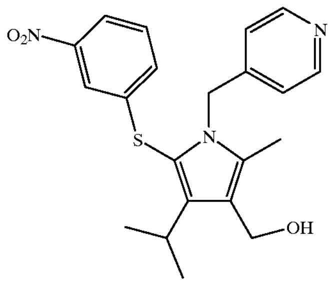 | 4-Isopropyl-2-methyl-5-(3-nitrophenylthio)-1-[(4-pyridyl)methyl]-1H-pyrrole-3-methanol |
| 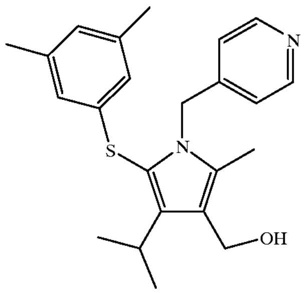 | 5-(3,5-Dimethylphenylthio)-4-isopropyl-2-methyl-1-[(4-pyridyl)methyl]-1H-pyrrole-3-methanol |

TABLE 1-continued

| STRUCTURE | SYSTEMATIC NAME |
|---|---|
|  | 4-Iosropyl-5-isopropylthio-2-methyl-1-[(4-pyridyl)methyl]-1H-pyrrole-3-methanol |
| 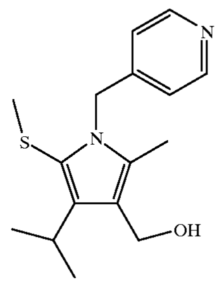 | 4-Isopropyl-2-methyl-5-methylthio-1-[(4-pyridyl)mehtyl]-1H-pyrrole-3-methanol |
| 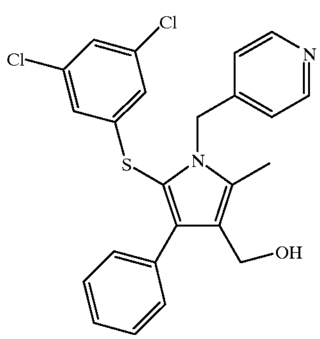 | 5-(3,5-Dichlorophenylthio)-2-methyl-4-phenyl-1-[(4-pyridyl)methyl]-1H-pyrrole-3-methanol |
| 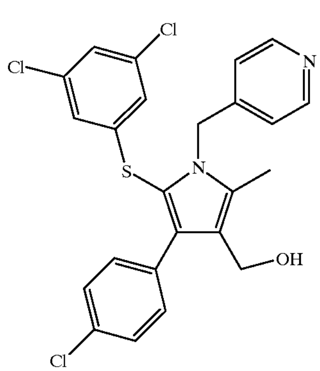 | 4-(4-Chlorophenyl)-5-(3,5-dichlorophenylthio)-2-methyl-1-[(4-pyridyl)methyl]-1H-pyrrole-3-methanol |

TABLE 1-continued

| STRUCTURE | SYSTEMATIC NAME |
|---|---|
| 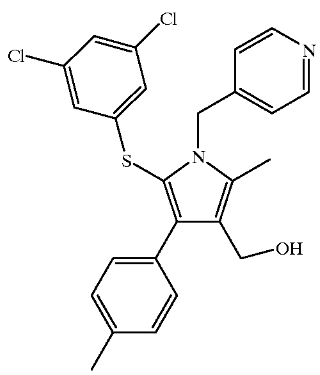 | 5-(3,5-Dichlorophenylthio)-2-methyl-4-(4-methylphenyl)-1-[(4-pyridyl)methyl]-1H-pyrrole-3-methanol |
| 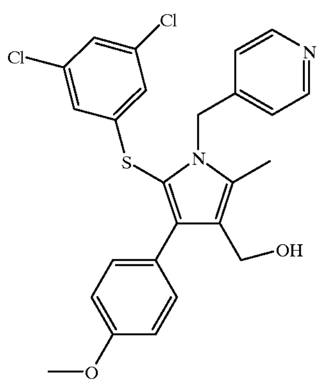 | 5-(3,5-Dichlorophenylthio)-4-(4-methoxyphenyl)-2-methyl-1-[(4-pyridyl)methyl]-1H-pyrrole-3-methanol |
| 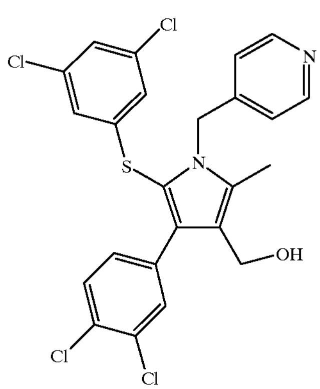 | 4-(3,4-Dichlorophenyl)-5-(3,5-dichlorophenylthio)-2-methyl-1-[(4-pyridyl)methyl]-1H-pyrrole-3-methanol |
| 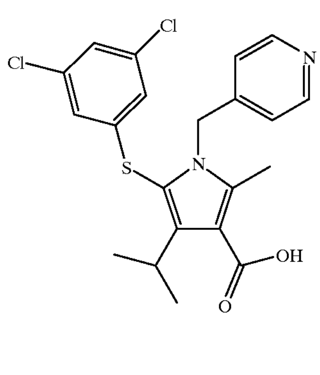 | 5-(3,5-Dichlorophenylthio)-4-isopropyl-2-methyl-1-[(4-pyridyl)methyl]-1H-pyrrole-3-carboxylic acid |

TABLE 1-continued

| STRUCTURE | SYSTEMATIC NAME |
|---|---|
| 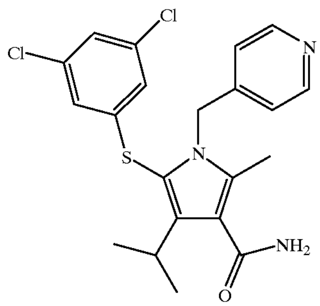 | 5-(3,5-Dichlorophenylthio)-4-isopropyl-2-methyl-1-[(4-pyridyl)methyl]-1H-pyrrole-3-carboxamide |
| 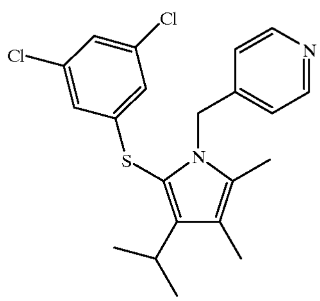 | 4-[[2-(3,5-Dichlorophenylthio)-3-isopropyl-4,5-dimethyl-1H-pyrrol-1-yl]methyl]pyridine |
| 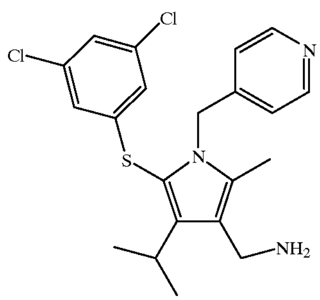 | 5-(3,5-Dichlorophenylthio)-4-isopropyl-2-methyl-1-[(4-pyridyl)methyl]-1H-pyrrole-3-methylamine |
| 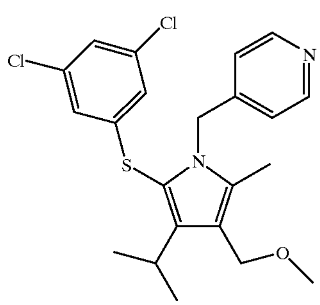 | 4-[[2-(3,5-Dichlorophenylthio)-3-isopropyl-4-(methoxymethyl)-5-methyl-1H-pyrrol-1-yl]methyl]pyridine |
| 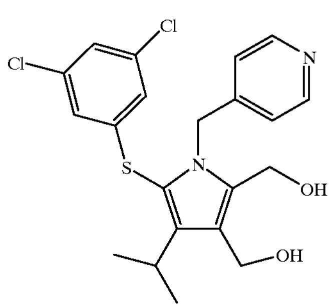 | 5-(3,5-Dichlorophenylthio)-3-(hydroxymethyl)-4-isopropyl-1-[(4-pyridyl)methyl]-1H-pyrrole-2-methanol |

TABLE 1-continued

| STRUCTURE | SYSTEMATIC NAME |
|---|---|
| 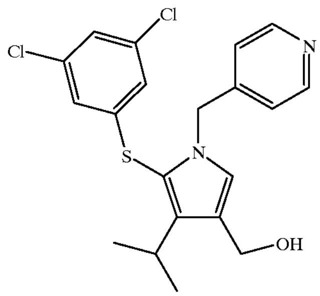 | 5-(3,5-Dichlorophenylthio)-4-isopropyl-1-[(4-pyridyl)methyl]-1H-pyrrole-3-methanol |
| 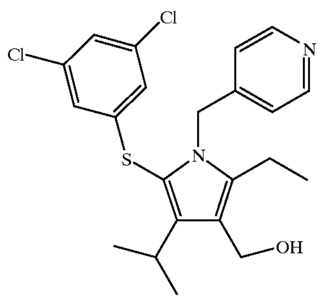 | 5-(3,5-Dichlorophenylthio)-2-ethyl-4-isopropyl-1-[(4-pyridyl)methyl]-1H-pyrrole-3-methanol |
| 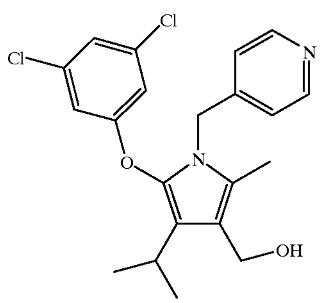 | 5-(3,5-Dichlorophenoxy)-4-isopropyl-2-methyl-1-[(4-pyridyl)methyl]-1H-pyrrole-3-methanol |
| 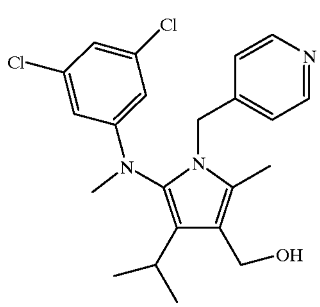 | 5-[(3,5-Dichlorophenyl)methylamino]-4-isopropyl-2-methyl-1-[(4-pyridyl)methyl]-1H-pyrrole-3-methanol |
| 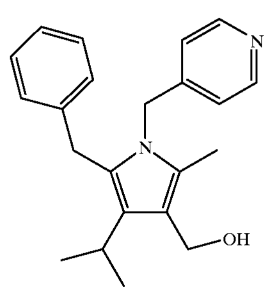 | 5-Benzyl-4-isopropyl-2-methyl-1-[(4-pyridyl)methyl]-1H-pyrrole-3-methanol |

TABLE 1-continued

| STRUCTURE | SYSTEMATIC NAME |
|---|---|
| 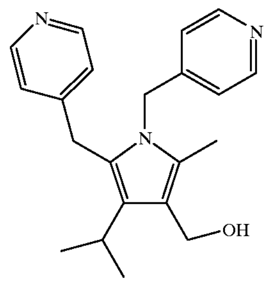 | 4-Isopropyl-2-methyl-1,5-bis[(4-pyridyl)methyl]-1H-pyrrole-3-methanol |
| 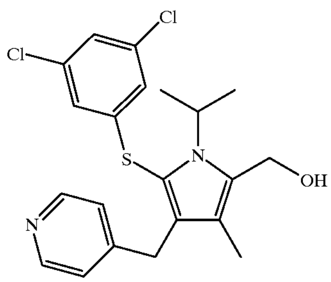 | 5-(3,5-Dichlorophenylthio)-1-isopropyl-3-methyl-4-[(4-pyridyl)methyl]-1H-pyrrole-2-methanol |
| 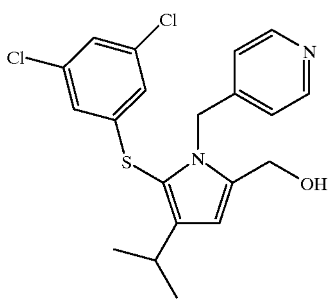 | 5-(3,5-Dichlorophenylthio)-4-isopropyl-1-[(4-pyridyl)methyl]-1H-pyrrole-2-methanol |
| 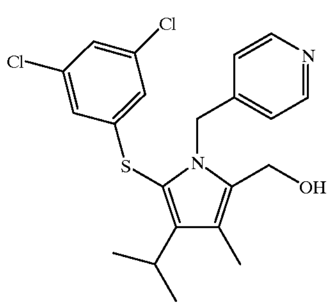 | 5-(3,5-Dichlorophenylthio)-4-isopropyl-3-methyl-1-[(4-pyridyl)methyl]-1H-pyrrole-2-methanol |
| 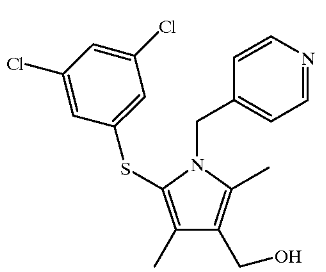 | 5-(3,5-Dichlorophenylthio)-2,4-dimethyl-1-[(4-pyridyl)methyl]-1H-pyrrole-3-methanol |

TABLE 1-continued

| STRUCTURE | SYSTEMATIC NAME |
| --- | --- |
| 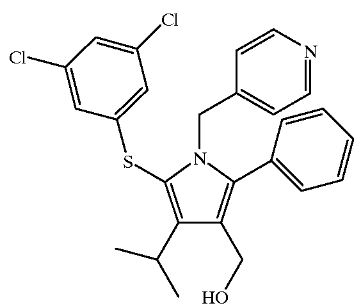 | 5-(3,5-Dichlorophenylthio)-4-isopropyl-2-phenyl-1-[(4-pyridyl)methyl]-1H-pyrrole-3-methanol |
| 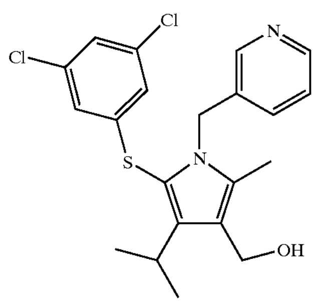 | 5-(3,5-Dichlorophenylthio)-4-isopropyl-2-methyl-1-[(3-pyridyl)methyl]-1H-pyrrole-3-methanol |
| 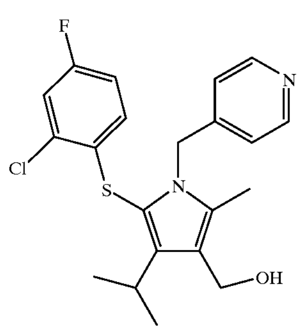 | 5-(2-chloro-4-fluorophenylthio)-4-isopropyl-2-methyl-1-[(4-pyridyl)methyl]-1H-pyrrole-3-methanol |
| 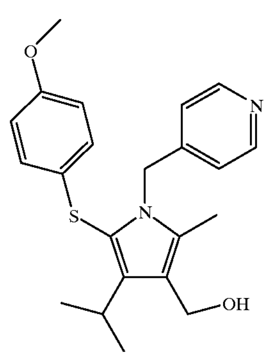 | 4-Iospropyl-5-(4-methoxyphenylthio)-2-methyl-1-[(4-pyridyl)methyl]-1H-pyrrole-3-methanol |

TABLE 1-continued

| STRUCTURE | SYSTEMATIC NAME |
| --- | --- |
| 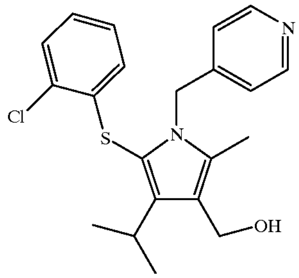 | 5-(2-Chlorophenylthio)-4-isopropyl-2-methyl-1-[(4-pyridyl)methyl]-1H-pyrrole-3-methanol |
| 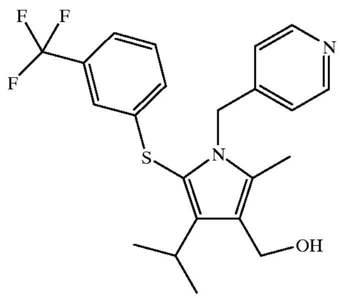 | 5-[3-(Trifluoromethyl)phenylthio]-4-isopropyl-2-methyl-1-[(4-pyridyl)methyl]-1H-pyrrole-3-methanol |
| 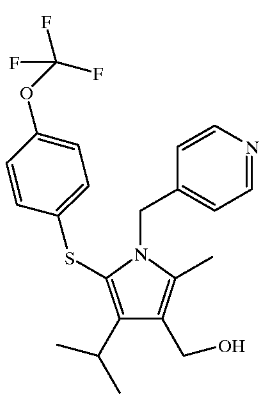 | 5-[4-(Trifluoromethoxy)phenylthio]-4-isopropyl-2-methyl-1-[(4-pyridyl)methyl]-1H-pyrrole-3-methanol |
| 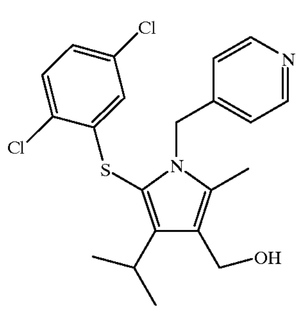 | 5-(2,5-Dichlorophenylthio)-4-isopropyl-2-methyl-1-[(4-pyridyl)methyl]-1H-pyrrole-3-methanol |

TABLE 1-continued

| STRUCTURE | SYSTEMATIC NAME |
|---|---|
| 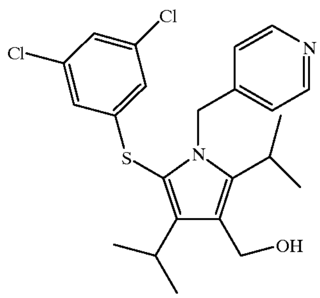 | 5-(3,5-Dichlorophenylthio)-2,4-diisopropyl-1-[(4-pyridyl)methyl]-1H-pyrrole-3-methanol |
| 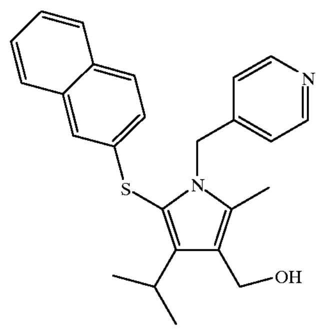 | 4-Isopropyl-2-methyl-5-(2-naphthylthio)-1[(4-pyridinyl)methyl]-1H-pyrrole-3-methanol |
| 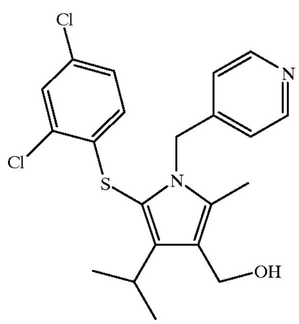 | 5-(2,4-Dichlorophenylthio)-4-isopropyl-2-methyl-1-[(4-pyridyl)methyl]-1H-pyrrole-3-methanol |
| 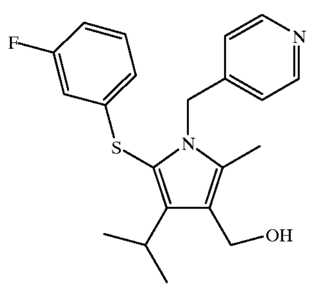 | 5-(3-Fluorophenylthio)-4-isopropyl-2-methyl-1-[(4-pyridyl)methyl]-1H-pyrrole-3-methanol |
| 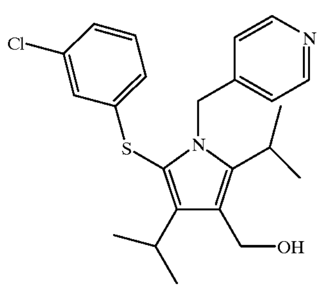 | 5-(3-Chlorophenylthio)-2,4-diisopropyl-1-[(4-pyridyl)methyl]-1H-pyrrole-3-methanol |

TABLE 1-continued

| STRUCTURE | SYSTEMATIC NAME |
|---|---|
| 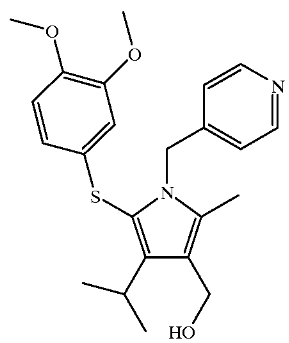 | 4-Isopropyl-5-(3,4-dimethoxyphenylthio)-2-methyl-1-[(4-pyridyl)methyl]-1H-pyrrole-3-methanol |
| 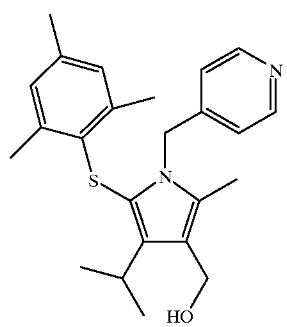 | 4-Isopropyl-2-methyl-5-(2,4,6-trimethylphenylthio)-1-[(4-pyridyl)methyl]-1H-pyrrole-3-methanol |
| 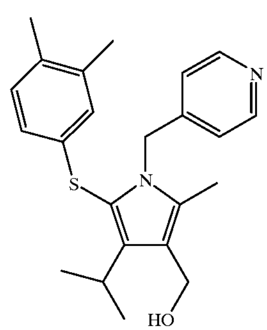 | 4-Isopropyl-2-methyl-5-(3,4-dimethylphenylthio)-1-[(4-pyridyl)methyl]-1H-pyrrole-3-methanol |
| 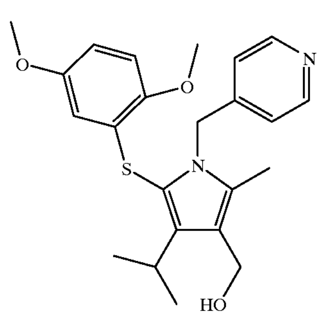 | 4-Isopropyl-5-(2,5-dimethoxyphenylthio)-2-methyl-1-[(4-pyridyl)methyl]-1H-pyrrole-3-methanol |

TABLE 1-continued

| STRUCTURE | SYSTEMATIC NAME |
|---|---|
| 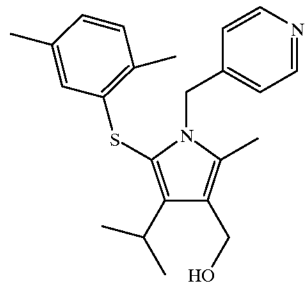 | 4-Isopropyl-2-methyl-5-(2,5-dimethylphenylthio)-1-[(4-pyridyl)methyl]-1H-pyrrole-3-methanol |
| 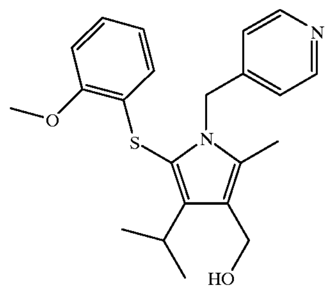 | 4-Isopropyl-5-(2-methoxyphenylthio)-2-methyl-1-[(4-pyridyl)methyl]-1H-pyrrole-3-methanol |
| 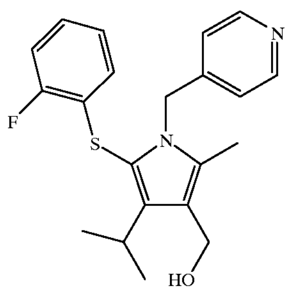 | 5-(2-Fluorophenylthio)-4-isopropyl-2-methyl-1-[(4-pyridyl)methyl]-1H-pyrrole-3-methanol |
| 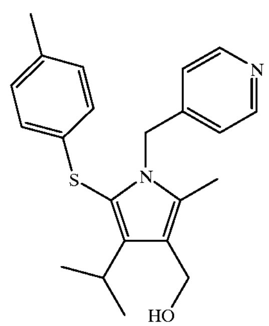 | 4-Isopropyl-2-methyl-5-(4-methylphenylthio)-1-[(4-pyridyl)methyl]-1H-pyrrole-3-methanol |
| 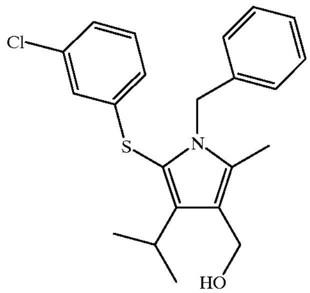 | 1-Benzyl-5-(3-chlorophenylthio)-4-isopropyl-2-methyl-1H-pyrrole-3-methanol |

TABLE 1-continued

| STRUCTURE | SYSTEMATIC NAME |
|---|---|
| 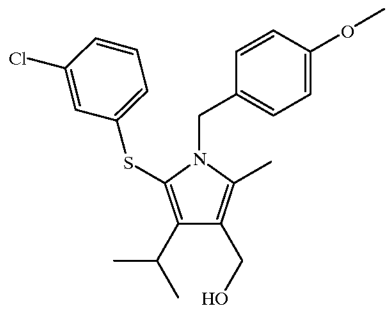 | 5-(3-Chlorophenylthio)-4-isopropyl-1-(4-methoxybenzyl)-2-methyl-1H-pyrrole-3-methanol |
| 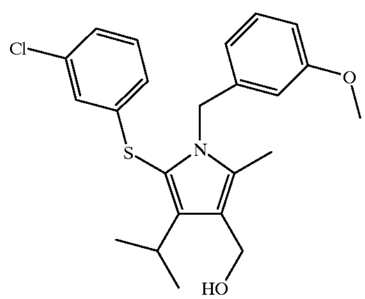 | 5-(3-Chlorophenylthio)-4-isopropyl-1-(3-methoxybenzyl)-2-methyl-1H-pyrrole-3-methanol |
| 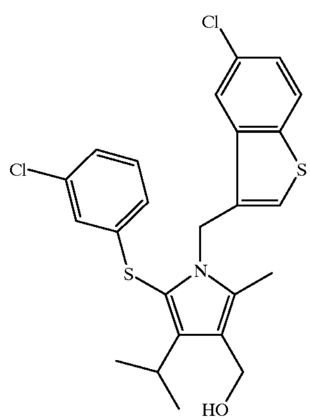 | 1-[(5-Chloro-1-benzothiophen-3-yl)methyl]-5-(3-chlorohenylthio)-4-isopropyl-2-methyl-1H-pyrrole-3-methanol |
| 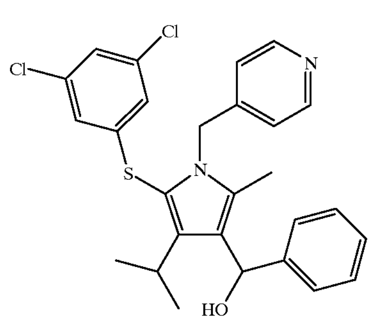 | alpha(RS)-[5-(3,5-Dichlorophenylthio)-4-isopropyl-2-methyl-1-[(4-pyridyl)methyl]-1H-pyrrole-3-yl]benzyl alcohol |

TABLE 1-continued

| STRUCTURE | SYSTEMATIC NAME |
| --- | --- |
| 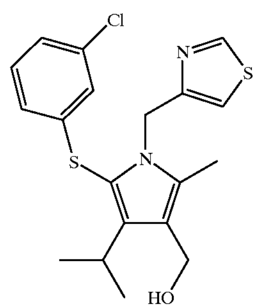 | 5-(3-Chlorophenylthio)-4-isopropyl-2-methyl-1-[(4-thiazolyl)methyl]-1H-pyrrole-3-methanol |
| 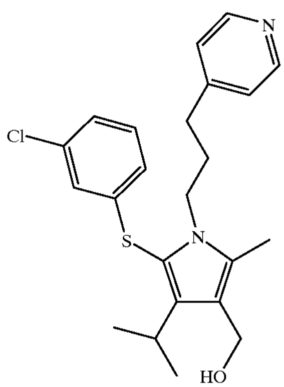 | 5-(3-Chlorophenylthio)-4-isopropyl-2-methyl-1-[(3-(4-pyridyl)propyl]-1H-pyrrole-3-methanol |
| 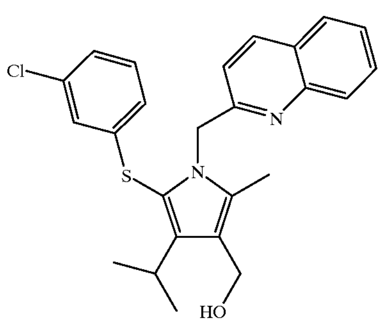 | 5-(3-Chlorophenylthio)-4-isopropyl-2-methyl-1-[(2-quinolyl)methyl]-1H-pyrrole-3-methanol |
| 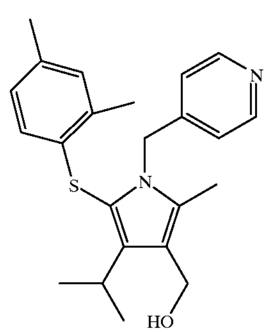 | 4-Isopropyl-2-methyl-5-(2,4-dimethylphenylthio)-1-[(4-pyridyl)methyl]-1H-pyrrole-3-methanol |

TABLE 1-continued

| STRUCTURE | SYSTEMATIC NAME |
| --- | --- |
| 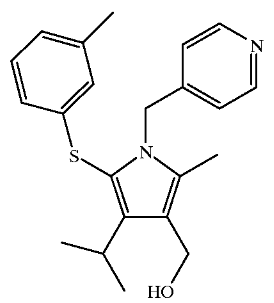 | 4-Isopropyl-2-methyl-5-(3-methylphenylthio)-1-[(4-pyridyl)methyl]-1H-pyrrole-3-methanol |
| 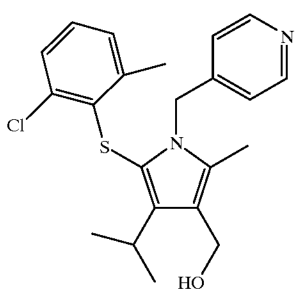 | 5-(2-Chloro-6-methylphenylthio)-4-isopropyl-2-methyl-1-[(4-pyridyl)methyl]-1H-pyrrole-3-methanol |
| 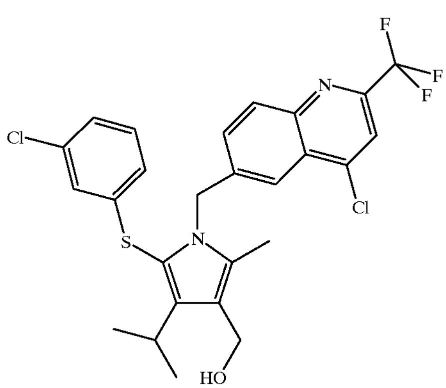 | 5-(3-Chlorophenylthio)-1-[[4-chloro-2-(trifluoromethyl)-6-quinolyl]methyl]-4-isopropyl-2-methyl-1H-pyrrole-3-methanol |
| 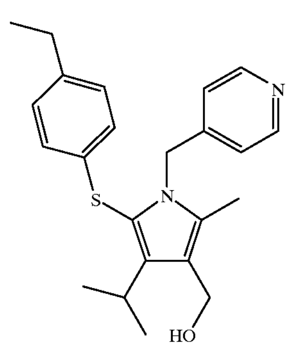 | 5-(4-Ethylphenylthio)-4-isopropyl-2-methyl-1-[(4-pyridyl)methyl]-1H-pyrrole-3-methanol |

TABLE 1-continued

| STRUCTURE | SYSTEMATIC NAME |
|---|---|
| 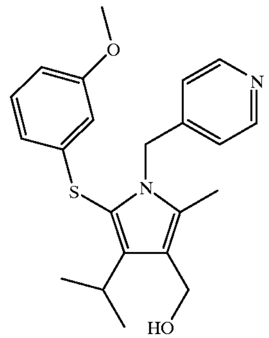 | 4-Iospropyl-5-(3-methoxyphenylthio)-2-methyl-1-[(4-pyridyl)methyl]-1H-pyrrole-3-methanol |
| 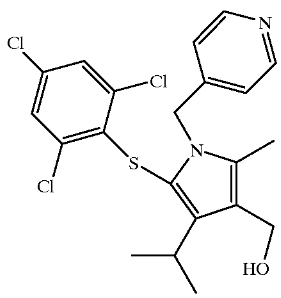 | 5-(2,4,6-Trichlorophenylthio)-4-isopropyl-2-methyl-1-[(4-pyridyl)methyl]-1H-pyrrole-3-methanol |
| 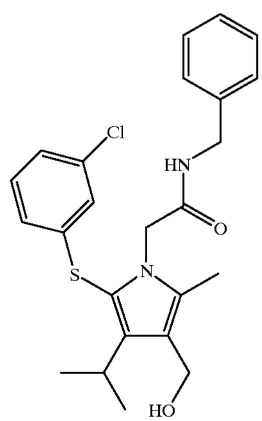 | N-Benzyl-2-(3-chlorophenylthio)-4-(hydroxymethyl)-3-isopropyl-5-methyl-1-pyrroleacetamide |
| 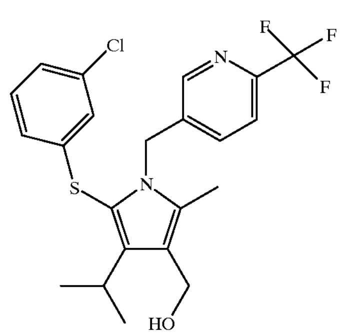 | 5-(3-Chlorophenylthio)-1-[[6-(trifluoromethyl)-3-pyridyl]methyl]-4-isopropyl-2-methyl-1H-pyrrole-3-methanol |

TABLE 1-continued

| STRUCTURE | SYSTEMATIC NAME |
|---|---|
| 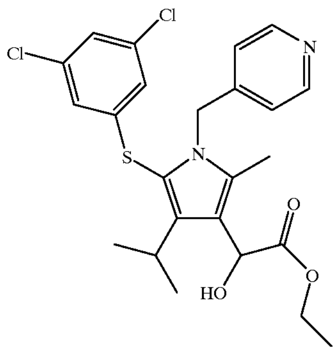 | [5-(3,5-Dichloro-phenylsulfanyl)-4-isopropyl-2-methyl-1-pyridin-4-ylmethyl-1H-pyrrol-3-yl]-hydroxy-acetic acid ethyl ester |
| 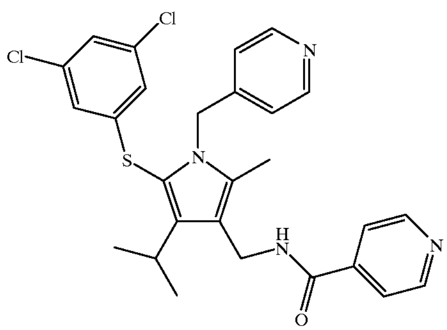 | N-[[5-(3,5-Dichlorophenylthio)-4-isopropyl-2-methyl-1-[(4-pyridyl)methyl]-1H-pyrrol-3-yl]methyl]-4-pyridineacetamide |
| 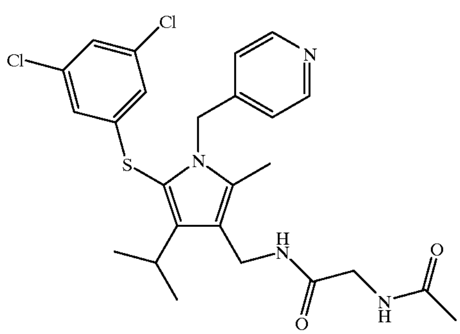 | 2-Acetamido-N-[[5-(3,5-dichlorophenylthio)-4-isopropyl-2-methyl-1-[(4-pyridyl)methyl]-1H-pyrrol-3-yl]methyl]acetamide |
| 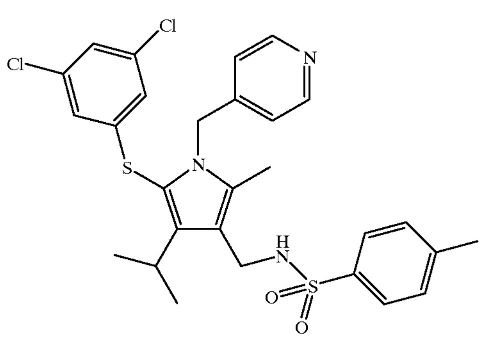 | N-[[5-(3,5-Dichlorophenylthio)-4-isopropyl-2-methyl-1-[(4-pyridyl)methyl]-1H-pyrrol-3-yl]methyl]-p-toluenesulfonamide |

TABLE 1-continued

| STRUCTURE | SYSTEMATIC NAME |
|---|---|
| 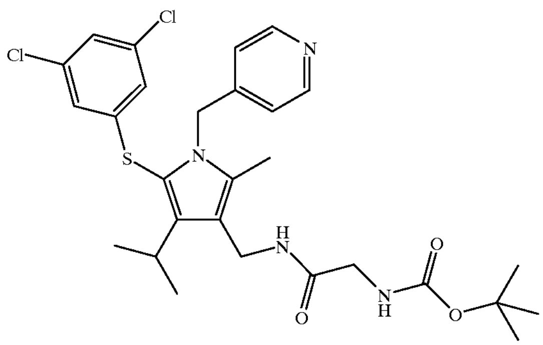 | tert.-butyl[[[[5-(3,5-dichlorophenylthio)-4-isopropyl-2-methyl-1-[(4-pyridyl)methyl]-1H-pyrrol-3-yl]methyl]carbamoyl]methyl]carbamate |
| 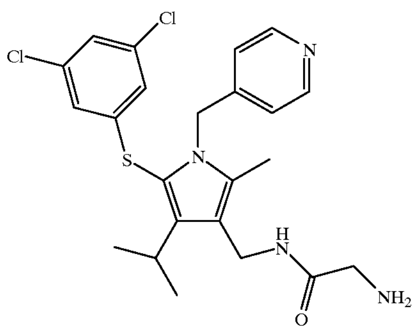 | N2-[[5-(3,5-Dichlorophenylthio)-4-isopropyl-2-methyl-1-[(4-pyridyl)methyl]-1H-pyrrol-3-yl]methyl]glycinamide |
| 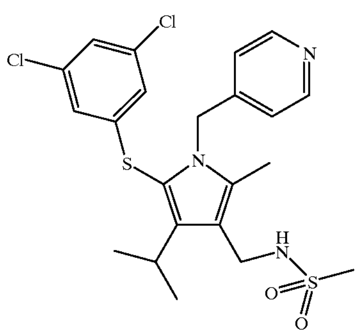 | N-[[5-(3,5-Dichlorophenylthio)-4-isopropl-2-methyl-1-[(4-pyridyl)methyl-1H-pyrrol-3-yl]methyl]methanesulfonamide |
| 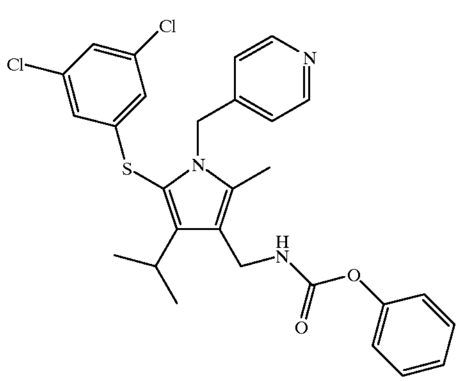 | Phenyl[[5-(3,5-dichlorohenylthio)-4-isopropyl-2-methyl-1-[(4-pyridyl)methyl]-1H-pyrrol-3-yl]methyl]carbamate |

TABLE 1-continued

| STRUCTURE | SYSTEMATIC NAME |
|---|---|
| 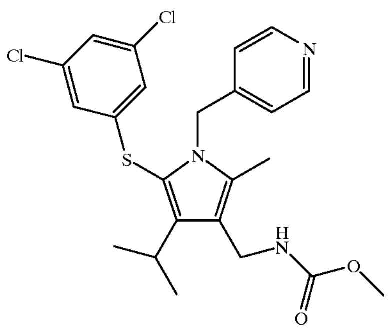 | Methyl[[5-(3,5-dichlorophenylthio)-4-isopropyl-2-methyl-1-[(4-pyridyl)methyl]-1H-pyrrol-3-yl]methyl]carbamate |
| 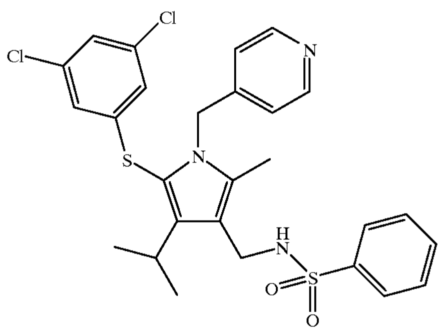 | N-[[5-(3,5-Dichlorophenylthio)-4-isopropyl-2-methyl-1-[(4-pyridyl)methyl]-1H-pyrrol-3-yl]methyl]benzenesulfonamide |
| Chiral | N1-acetyl-O-tert.-butyl-N2-[[5-(3,5-dichlorohenylthio)-4-isopropyl-2-methyl-1-[(4-pyridyl)methyl]-1H-pyrrol-3-ylmethyl]-L-serinamide |
| Chiral | N1-acetyl-N2-[[5-(3,5-dichlorophenylthio)-4-isopropyl-2-methyl-1-[(4-pyridyl)methyl]-1H-pyrrol-3-yl]methyl]-L-serinamide |

TABLE 1-continued

| STRUCTURE | SYSTEMATIC NAME |
|---|---|
| 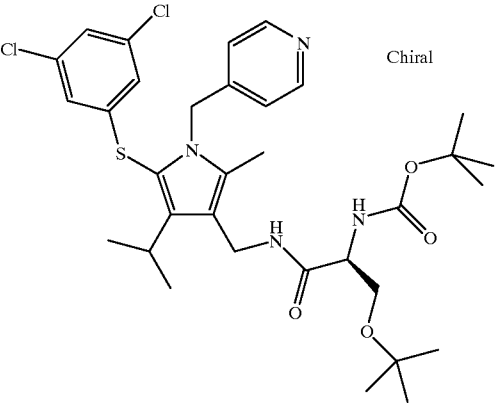 Chiral | N1-(tert.-butoxycarbonyl)-O-tert.-butyl-N2-[[5-(3,5-dichlorophenylthio)-4-isopropyl-2-methyl-1-[(4-pyridyl)methyl]-1H-pyrrol-3-yl]methyl]-L-serinamide |
| 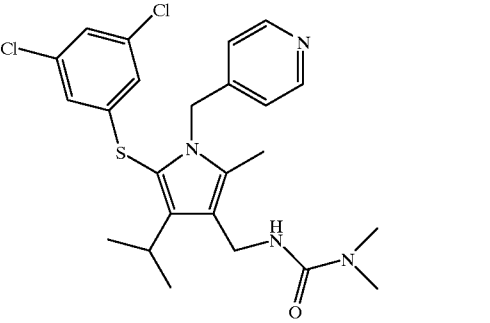 | 1-[[5-(3,5-Dichlorophenylthio)-4-isopropyl-2-methyl-1-[(4-pyridyl)methyl]-1H-pyrrol-3-yl]methyl]-3,3-dimethylurea |
| 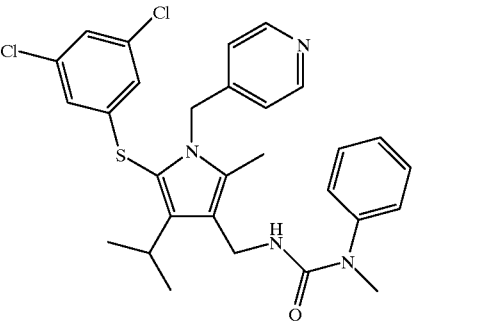 | 1-[[5-(3,5-Dichlorophenylthio)-4-isopropyl-2-methyl-1-[(4-pyriyl)methyl]-1H-pyrrol-3-yl]methyl]-3-methyl-3-phenylurea |
| 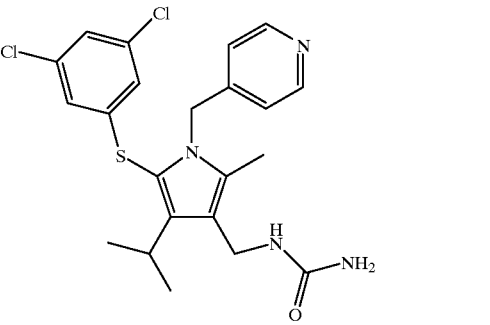 | 1-[[5-(3,5-Dichlorophenylthio)-4-isopropyl-2-methyl-1-[(4-pyridyl)methyl]-1H-pyrrol-3-yl]methyl]urea |

TABLE 1-continued

| STRUCTURE | SYSTEMATIC NAME |
|---|---|
| 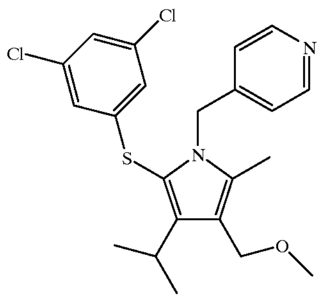 | 4-[[2-(3,5-Dichlorophenylthio)-3-isopropyl-4-(methoxymethyl)-5-methyl-1-pyrrolyl]methyl]pyridine |
| 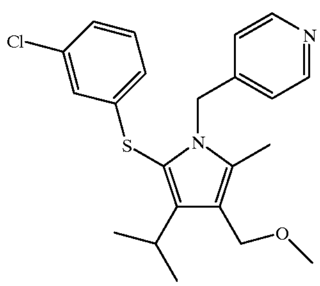 | 4-[[2-(3-Chlorophenylthio)-3-isopropyl-4-(methoxymethyl)-5-methyl-1-pyrrolyl]methyl]pyridine |
| 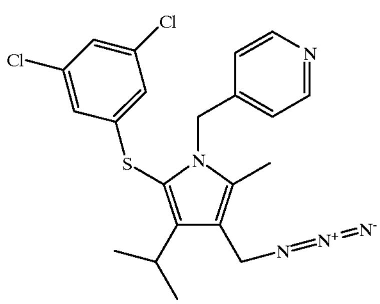 | 4-[[3-(Azidomethyl)-5-(3,5-dichlorophenylthio)-5-isopropyl-2-methyl-1-pyrrolyl]methyl]pyridine |
| 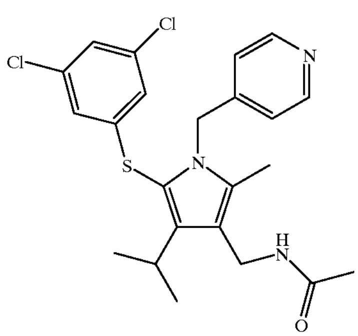 | N-[[5-(3,5-Dichlorophenylthio)-4-isopropyl-2-methyl-1-[(4-pyridyl)methyl]-1H-pyrrol-3-yl]methyl]acetamide |
| 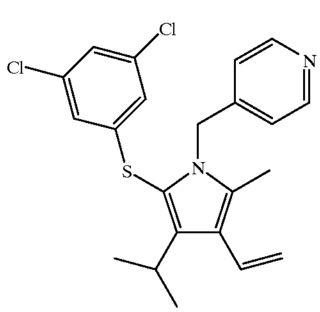 | 4-[[2-(3,5-Dichlorophenylthio)-3-isopropyl-5-methyl-4-vinyl-1-pyrrolyl]methyl]pyridine |

TABLE 1-continued

| STRUCTURE | SYSTEMATIC NAME |
|---|---|
| 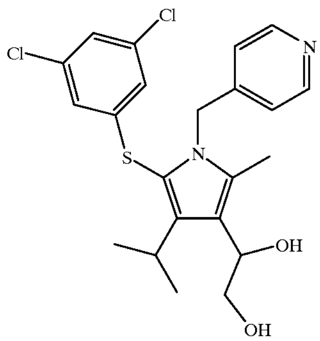 | 1(RS)-[5-(3,5-Dichlorophenylthio)-4-isopropyl-2-methyl-1-[(4-pyridyl)methyl]-1H-pyrrol-3-yl]-1,2-ethanediol |
| 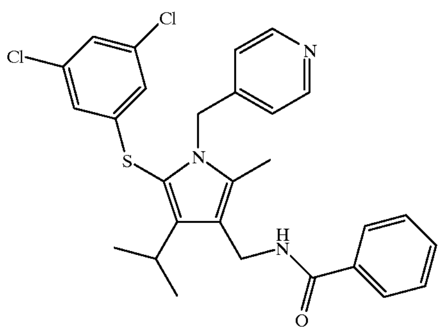 | N-[[5-(3,5-Dichlorophenylthio)-4-isopropyl-2-methyl-1-[(4-pyridyl)methyl]-1H-pyrrol-3-yl]methyl]benzamide |
| 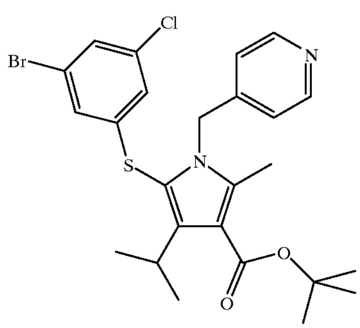 | tert.-butyl 5-(3-bromo-5-chlorophenylthio)-4-isopropyl-2-methyl-1-[(4-pyridyl)methyl]-1H-pyrrole-3-carboxylate |
| 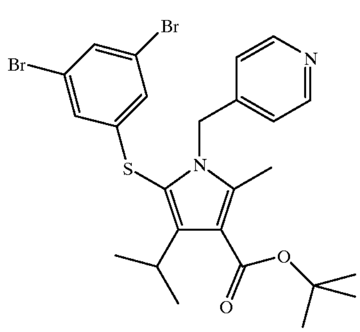 | tert.-butyl 5-(3,5-dibromophenylthio)-4-isopropyl-2-methyl-1-[(4-pyridyl)methyl]-1H-pyrrole-3-carboxylate |

TABLE 1-continued

| STRUCTURE | SYSTEMATIC NAME |
| --- | --- |
| 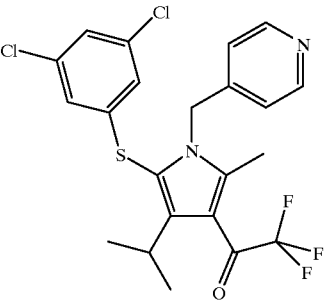 | 1-[5-(3,5-Dichlorophenylthio)-4-isopropyl-2-methyl-1-[(4-pyridyl)methyl]-1H-pyrrol-3-yl]-2,2,2-trifluoroethanone |
| 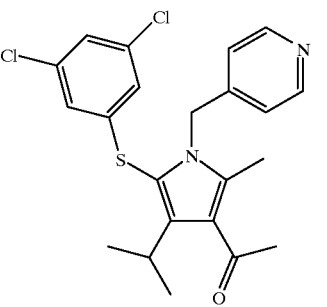 | 1-[5-(3,5-Dichlorophenylthio)-4-isopropyl-2-methyl-1-[(4-pyridyl)methyl]-1H-pyrrol-3-yl]ethanone |
| 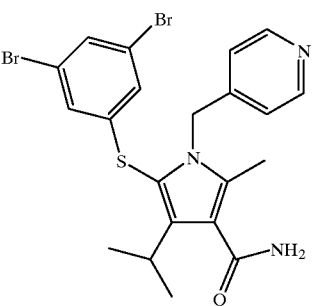 | 5-(3,5-Dibromophenylthio)-4-isopropyl-2-methyl-1-[(4-pyridyl)methyl]-1H-pyrrole-3-carboxamide |
| 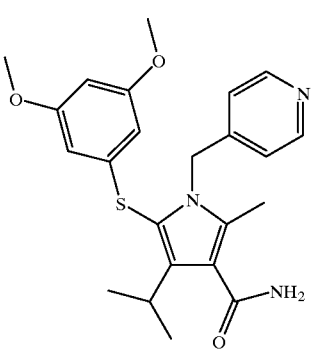 | 4-Isopropyl-5-(3,5-dimethoxyphenylthio)-2-methyl-1-[(4-pyridyl)methyl]-1H-pyrrole-3-carboxamide |

TABLE 1-continued

| STRUCTURE | SYSTEMATIC NAME |
| --- | --- |
| 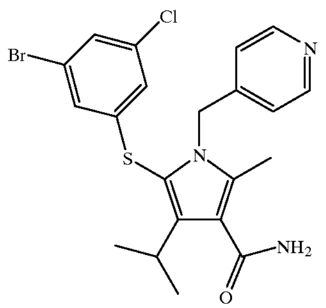 | 5-(3-Bromo-5-chlorophenylthio)-4-isopropyl-2-methyl-1-[(4-pyridyl)methyl]-1H-pyrrole-3-carboxamide |
| 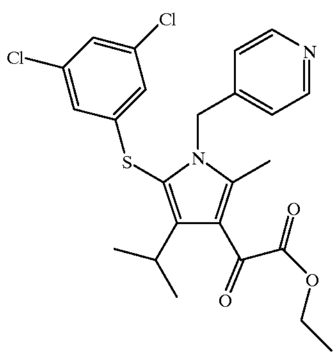 | Ethyl 5-(3,5-dichlorophenylthio)-4-isopropyl-2-methyl-1-[(4-pyridyl)methyl]-1H-pyrrole-3-glyoxalate |
| 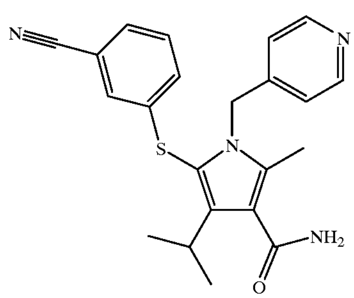 | 5-(3-Cyanophenylthio)-4-isopropyl-2-methyl-1-[(4-pyridyl)methyl]-1H-pyrrole-3-carboxamide |
| 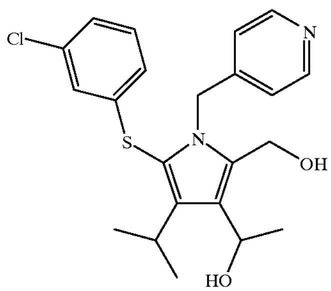 | 5-(3-Chlorophenylthio)-2-(hydroxymethyl)-4-isopropyl-alpha(RS)-methyl-1-[(4-pyridyl)methyl]-1H-pyrrole-3-ethanol |

TABLE 1-continued

| STRUCTURE | SYSTEMATIC NAME |
|---|---|
| 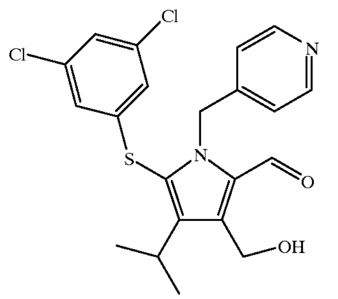 | 5-(3,5-Dichlorophenylthio)-3-(hydroxymethyl)-4-isopropyl-1-[(4-pyridyl)methyl]-1H-pyrrole-2-carboxaldehyde |
| 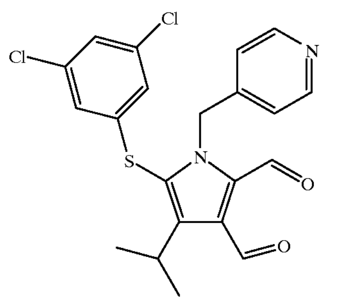 | 5-(3,5-Dichlorophenylthio)-4-isopropyl-1-[(4-pyridyl)methyl]-1H-pyrrole-2,3-dicarboxaldehyde |
| 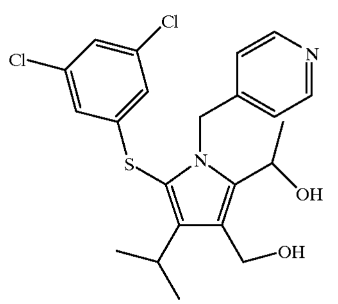 | 5-(3,5-Dichlorophenylthio)-3-(hydroxymethyl)-4-isopropyl-alpha(RS)-methyl-1-[(4-pyridyl)methyl]-1H-pyrrole-2-ethanol |
| 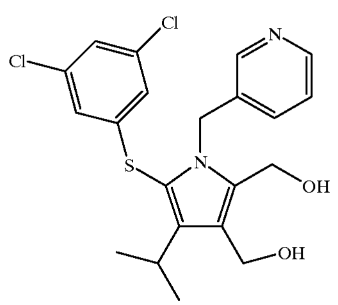 | 5-(3,5-Dichlorophenylthio)-4-isopropyl-1-[(3-pyridyl]methyl]-1H-pyrrole-2,3-dimethanol |
| 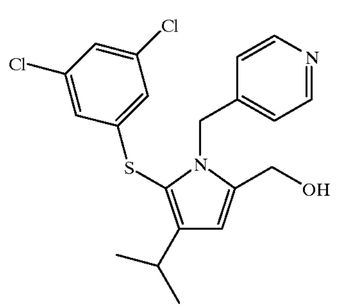 | 5-(3,5-Dichlorophenylthio)-4-isopropyl-1-[(4-pyridyl)methyl]-1H-pyrrole-2-methanol |

TABLE 1-continued

| STRUCTURE | SYSTEMATIC NAME |
|---|---|
| 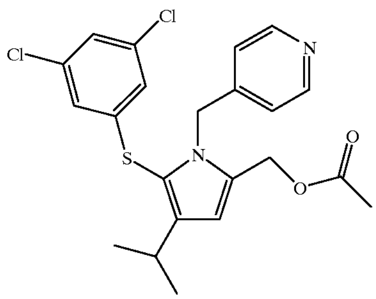 | [5-(3,5-Dichlorophenylthio)-4-isopropyl-1-[(4-pyridyl)methyl]-1H-pyrrol-2-yl]methyl acetate |
| 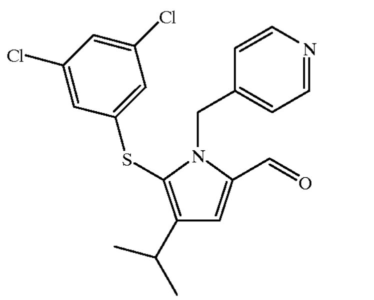 | 5-(3,5-Dichlorophenylthio)-4-isopropyl-1-[(4-pyridyl)methyl]-1H-pyrrole-2-carbaldehyde |
| 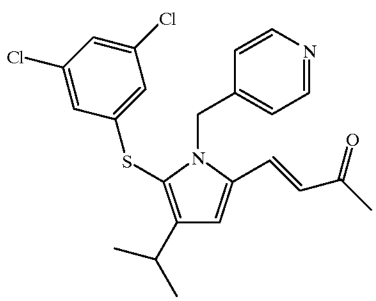 | 4-[5-(3,5-Dichloro-phenylsulfanyl)-4-isoproyl-1-pyridin-4-ylmethyl-1H-pyrrol-2-yl]-but-3-en-2-one |
| 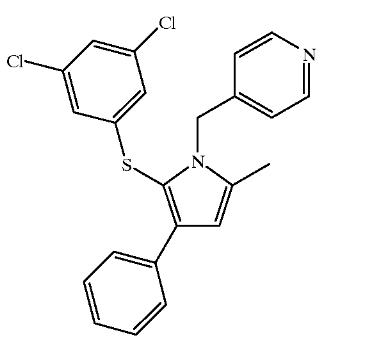 | 4-[[2-(3,5-Dichlorophenylthio)-5-methyl-3-phenyl-1-pyrrolyl]methyl]pyridine |
| 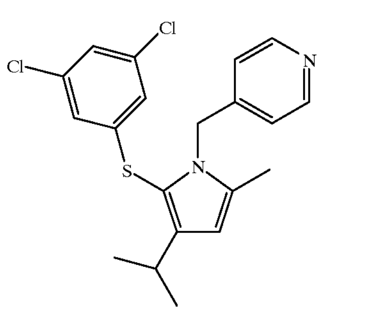 | 4-[[2-(3,5-Dichlorophenylthio)-3-isopropyl-5-methyl-1-pyrrolyl]methyl]pyridine |

TABLE 1-continued

| STRUCTURE | SYSTEMATIC NAME |
|---|---|
| 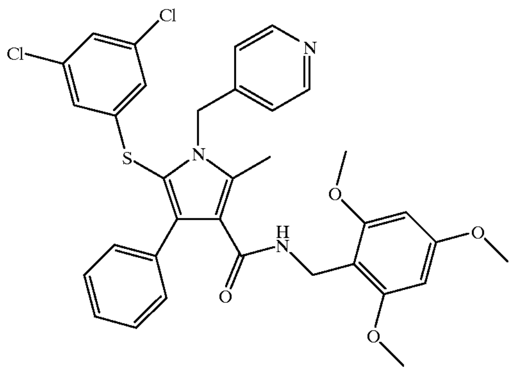 | 5-(3,5-Dichlorophenylthio)-N-(2,4,6-trimethoxybenzyl)-2-methyl-4-phenyl-1-[(4-pyridyl)methyl]-1H-pyrrole-3-carboxamide |
| 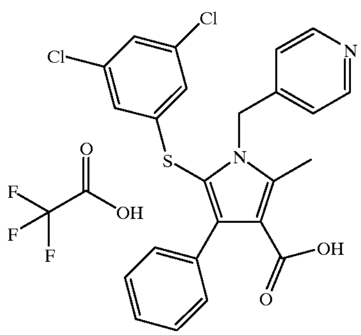 | 5-(3,5-Dichlorophenylthio)-2-methyl-4-phenyl-1-[(4-pyridyl)methyl]-1H-pyrrole-3-carboxylic acid trifluoroacetate (1:1) |
| 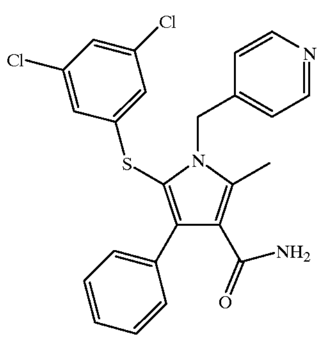 | 5-(3,5-Dichlorophenylthio)-4-phenyl-2-methyl-1-[(4-pyridyl)methyl]-1H-pyrrole-3-carboxamide |
| 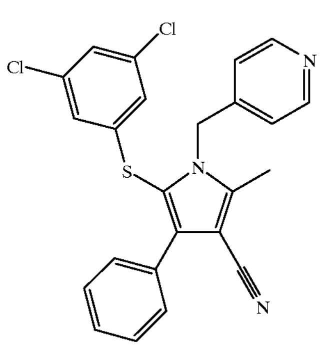 | 5-(3,5-Dichlorophenylthio)-2-methyl-4-phenyl-1-[(4-pyridyl)methyl]-1H-pyrrole-3-carbonitrile |

TABLE 1-continued

| STRUCTURE | SYSTEMATIC NAME |
|---|---|
| 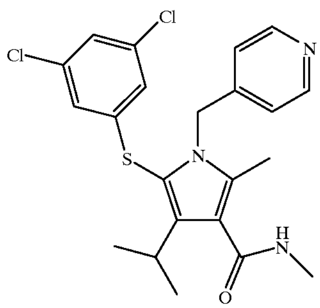 | 5-(3,5-Dichlorophenylthio)-4-isopropyl-N,2-dimethyl-1-[(4-pyridyl)methyl]-1H-pyrrole-3-carboxamide |
| 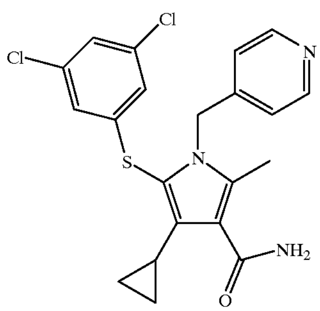 | 5-(3,5-Dichlorophenylthio)-4-cyclopropyl-2-methyl-1-[(4-pyridyl)methyl]-1H-pyrrole-3-carboxamide |
| 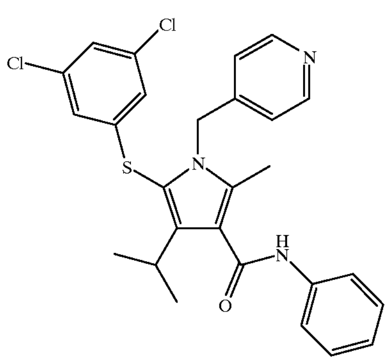 | 5-(3,5-Dichlorophenylthio)-4-isopropyl-2-methyl-1-[(4-pyridyl)methyl]-1H-pyrrole-3-carboxanilide |
| 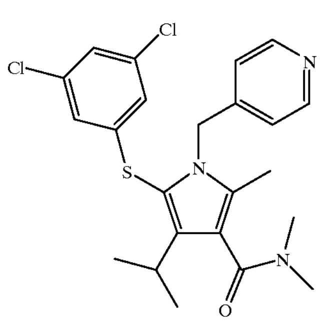 | 5-(3,5-Dichlorophenylthio)-4-isopropyl-N,N,2-trimethyl-1-[(4-pyridyl)methyl]-1H-pyrrole-3-carboxamide |

TABLE 1-continued

| STRUCTURE | SYSTEMATIC NAME |
|---|---|
| 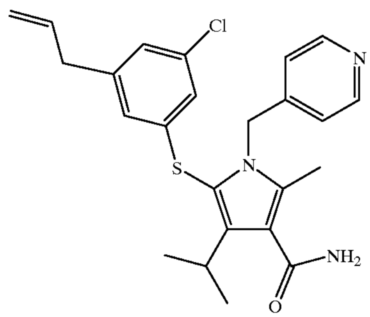 | 5-(3-Allyl-5-chlorophenylthio)-4-isopropyl-2-methyl-1-[(4-pyridyl)methyl]-1H-pyrrole-3-carboxamide |
| 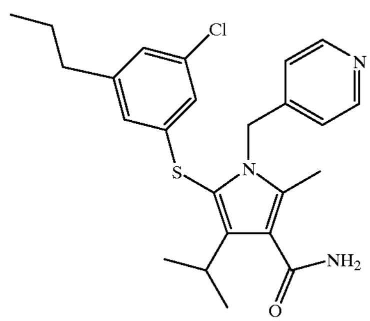 | 5-(3-Chloro-5-propylphenylthio)-4-isopropyl-2-methyl-1-[(4-pyridyl)methyl]-1H-pyrrole-3-carboxamide |
| 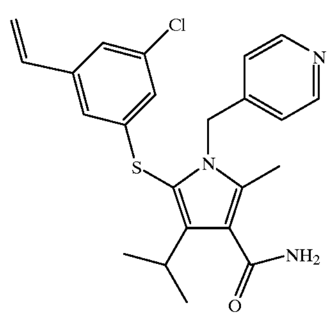 | 5-(3-Chloro-5-vinylphenylthio)-4-isopropyl-2-methyl-1-[(4-pyridyl)methyl]-1H-pyrrole-3-carboxamide |
| 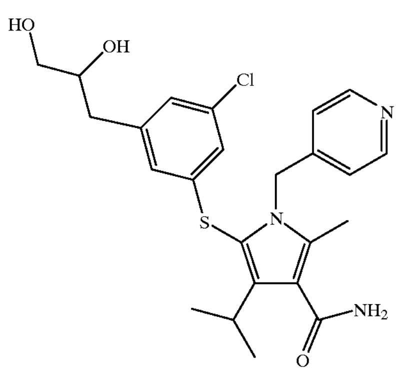 | 5-[3-Chloro-5-(2(RS),3-dihydroxypropyl)phenylthio]-4-isopropyl-2-methyl-1-[(4-pyridyl)methyl]-1H-pyrrole-3-carboxamide |

TABLE 1-continued

| STRUCTURE | SYSTEMATIC NAME |
|---|---|
| 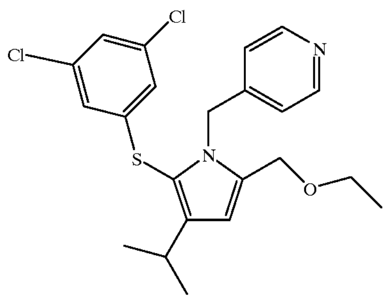 | 4-[[2-(3,5-Dichlorophenylthio)-5-(ethoxymethyl)-3-isopropyl-1-pyrrolyl]methyl]pyridine |
| 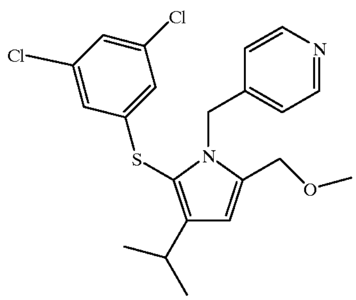 | 4-[[2-(3,5-Dichlorophenylthio)-3-isopropyl-5-(methoxymethyl)-1-pyrrolyl]methyl]pyridine |
| 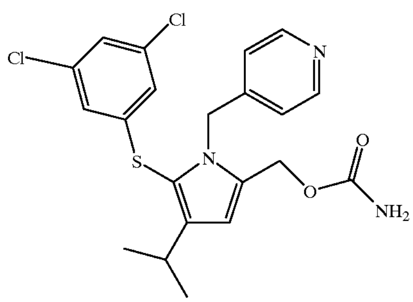 | [5-(3,5-Dichlorophenylthio)-4-isopropyl-1-[(4-pyridyl)methyl]-1H-pyrrol-2-yl]methyl carbamate |
| 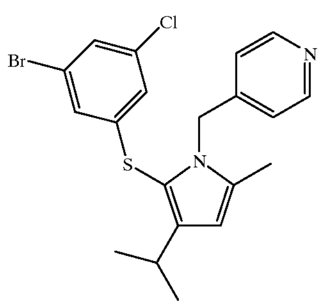 | 4-[[2-(3-Bromo-5-chlorophenylthio)-3-isopropyl-5-methyl-1-pyrrolyl]methyl]pyridine |
| 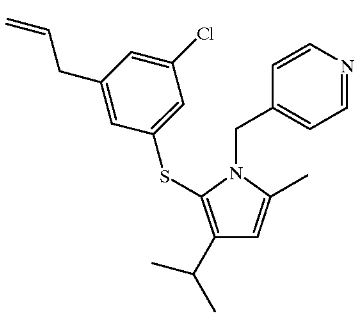 | 4-[[2-(3-Allyl-5-chlorophenylthio)-3-isopropyl-5-methyl-[(4-pyrrolyl]methyl]pyridine |

TABLE 1-continued

| STRUCTURE | SYSTEMATIC NAME |
|---|---|
| 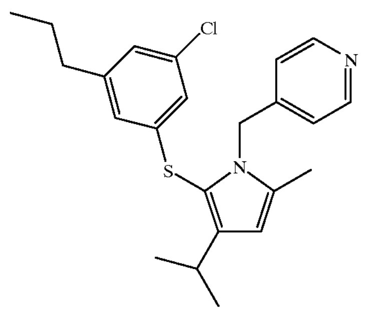 | 4-[[2-(3-Chloro-5-propylphenylthio)-3-isopropyl-5-methyl-1-pyrrolyl]methyl]pyridine |
| 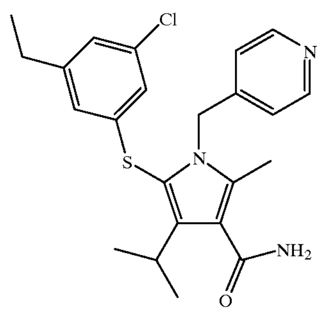 | 5-(3-Chloro-5-ethylphenylthio)-4-isopropyl-2-methyl-1-[(4-pyridyl)methyl]-1H-pyrrole-3-carboxamide |
| 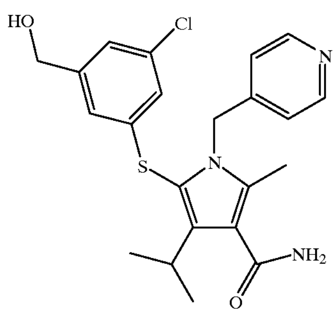 | 5-[3-Chloro-5-(hydroxymethyl)phenylthio]-4-isopropyl-2-methyl-1-[(4-pyridyl)methyl]-1H-pyrrole-3-carboxamide |
| 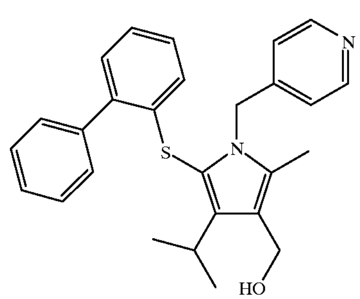 | 5-(2-Biphenylylthio)-4-isopropyl-2-methyl-1-[(4-pyridyl)methyl]-1H-pyrrol-3-methanol |
| 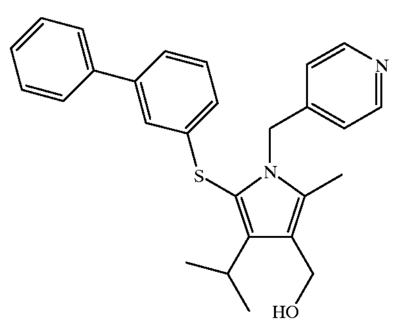 | 5-(3-Biphenylylthio)-4-isopropyl-2-methyl-1-[(4-pyridyl)methyl]-1H-pyrrole-3-methanol |

TABLE 1-continued

| STRUCTURE | SYSTEMATIC NAME |
|---|---|
| 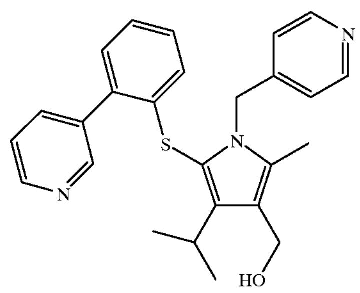 | 4-Isopropyl-2-methyl-1-[(4-pyridyl)methyl]-5-[2-(3-pyridyl)phenylthio]-1H-pyrrole-3-methanol |
| 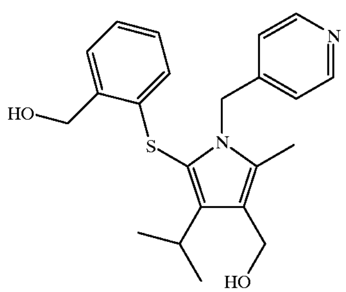 | 4-[2-(Hydroxymethyl)phenylthio]-4-isopropyl-2-methyl-1-[(4-pyridyl)methyl]-1H-pyrrole-3-methanol |
| 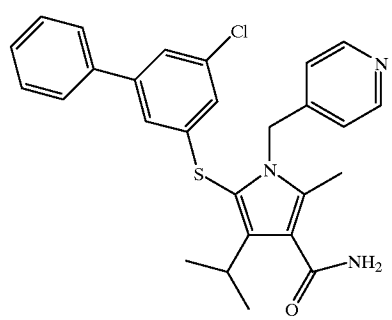 | 5-(5-Chloro-3-biphenylylthio)-4-isopropyl-2-methyl-1-[(4-pyridyl)methyl]-1H-pyrrole-3-carboxamide |
| 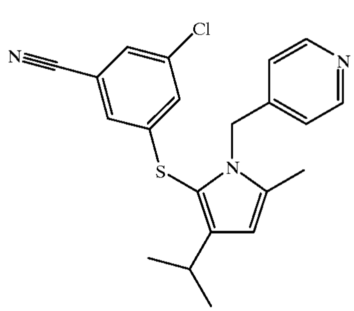 | 3-Chloro-5-[3-isopropyl-5-methyl-1-[(4-pyridinyl)methyl]-1H-pyrrol-2-ylthio]benzonitrile |

TABLE 1-continued

| STRUCTURE | SYSTEMATIC NAME |
|---|---|
| ![structure] | 5-[3-Iospropyl-5-methyl-1-[(4-pyridyl)methyl]-1H-pyrrol-2-ylthio]-1,3-dibenzonitrile |

The compounds of formula I and hydrolyzable esters or ethers thereof or a pharmaceutically acceptable salt thereof are inhibitors of the human immunodeficiency virus reverse transcriptase enzyme both in vitro and in vivo, and are useful in the control or prevention of diseases mediated by the human immunodeficiency virus (HIV).

These compounds are especially useful for treating viral diseases, immune mediated conditions or diseases, bacterial diseases, parasitic diseases, inflammatory diseases, hyperproliferative vascular diseases, tumors, and cancer.

In particular, compounds of the present invention and pharmaceutical compositions containing the same are useful as chemotherapeutic agents, inhibitors of viral replication and modulators of the immune system, and can be used (either alone or in combination with other antiviral agents such as interferon or derivatives thereof, such as conjugates with polyethylene glycol) for the treatment of diseases mediated by the human immunodeficiency virus (HIV) and other viral diseases such as retroviral infections.

Compounds of the invention can be used alone, or in combination with other therapeutically active agents, for example, an immunosuppressant, a chemotherapeutic agent, an anti-viral agent, an antibiotic, an anti-parasitic agent, an anti-inflammatory agent, an anti-fungal agent and/or an anti-vascular hyperproliferation agent.

The compounds of the present invention can be prepared as shown in the following scheme.

Reaction scheme 1:

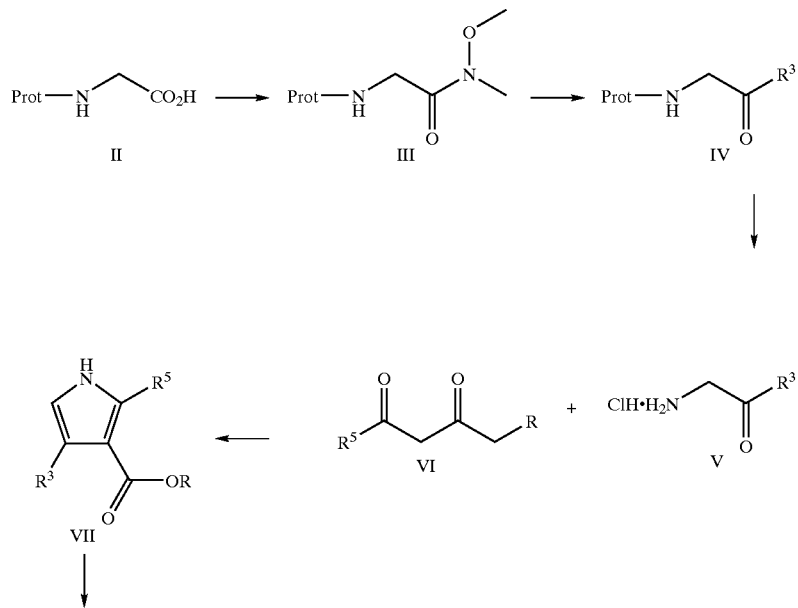

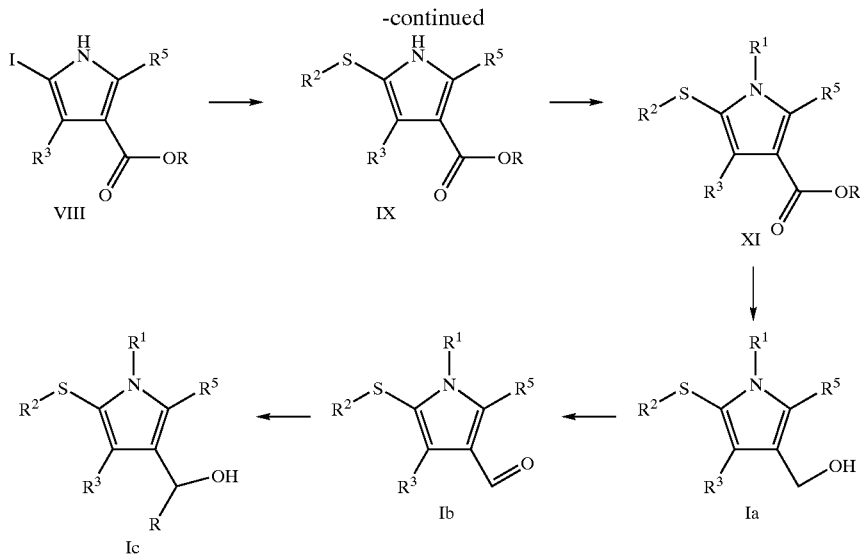

wherein $R^1$, $R^2$, $R^{3'}$ $R^5$ and R are as defined above for compounds of formula I and "Prot" is an amino protecting group.

In accordance with the present invention, compounds of formula VIII are prepared by reacting the compound of formula VII

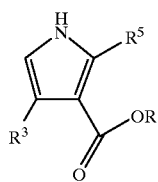

wherein R, $R^3$ and $R^5$ are as described above in formula I with a iodination agent to obtain the iodo pyrrole derivative of formula VIII

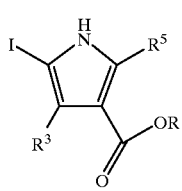

wherein R, $R^3$ and $R^5$ are as described in formula I.

Iodination agents useful for this reaction are known in the art and are for example N-iodosuccinimide, iodic acid in the presence of iodine, iodine in the presence of potassium iodide or sodium iodide, potassium iodide or sodium iodide in the presence of hydrogen peroxide.

The reactions can be carried out in a conventional manner known to the skilled in the art.

In reaction scheme I, N-protected glycine (commercially available from Fluka) of formula II is reacted with N,O-dimethylhydroxylamine hydrochloride in the presence of N-ethylmorpholine and N-ethyl-N'-(3-dimethylaminopropyl)carbodiimide hydrochloride under nitrogen atmosphere. The term "amino protecting group" (Prot) as used herein refers to groups such as those employed in peptide chemistry such as a tert.-butoxy-carbonyl group (t-BOC) or a benzyloxycarbonyl group (Z). Preferred amino protecting group (Prot) for this reaction is a tert.-butoxycarbonyl group. The reaction is conveniently carried out at a reaction temperature from 0° C. to room temperature in an inert solvent, for example halogenated hydrocarbons such as anhydrous dichloromethane or polar aprotic solvents such as N,N-dimethylformamide (DMF) or tetrahydrofuran (THF), preferably dichloromethane, to yield the N-protected glycine N-methyl-N-methoxyamide of formula III.

The N-protected glycine N-methyl-N-methoxyamide of formula III is converted to the compound of formula IV by reaction with a Grignard reagent of the formula $R^3MgX$ (commercially available or synthesized according to methods known from textbooks on organic chemistry e.g. from J. March (1992), "Advanced Organic Chemistry: Reactions, Mechanisms, and Structure", $4^{th}$ ed. John Wiley & Sons) wherein $R^3$ is as defined above but not hydrogen (for $R^3$ being hydrogen, the reaction sequence starts with compound of the formula V; see below) and X represents a halogen for example chlorine. The reaction is conveniently carried out in an inert solvent, for example ethers such as anhydrous tetrahydrofuran, diethyl ether, dioxane or a mixture of the mentioned solvents at a reaction temperature from 0° C. to room temperature. After the reaction, the Grignard product is worked-up in a manner known in the art for example with a solution of diluted hydrochloric acid, to yield the N-protected (α-amino ketone of formula IV.

In the next step of the reaction, the N-protected α-amino ketone of formula IV is reacted with trifluoroacetic acid or with hydrogen chloride thereby obtaining the deprotected α-amino ketone of formula V. In forming the compound of formula V, any conventional method for deprotecting protected amino groups can be utilized in carrying out this reaction. The deprotection reaction of the compounds of formula IV is preferably carried out with trifluoroacetic acid optionally dissolved in dichloromethane or hydrogen chloride dissolved in ethyl acetate, dioxane or methanol at a reaction temperature from 0° C. to room temperature. Most preferred, the deprotection reaction is carried out with hydrogen chloride dissolved in ethyl acetate.

The α-amino ketone of formula V is coupled with a β-keto ester of the formula VI wherein $R^5$ and R are as defined above (commercially available or synthesized according to methods known from textbooks on heterocyclic chemistry or organic chemistry e.g. from J. March (1992), "Advanced Organic Chemistry: Reactions, Mechanisms, and Structure", $4^{th}$ ed. John Wiley & Sons) to form a pyrrole derivative of the formula VII. The synthesis of the pyrrole derivatives according to the Knorr synthesis of the formula VII is carried out in a manner known in the art. The reaction of the compounds of formula V and VI to yield compounds of the formula VII is preferably carried out with a mixture of potassium hydroxide and $K_2HPO_4$ in water at a reaction temperature from 20 to 40° C. Most preferred, the reaction is carried out with a mixture of ethyl acetoacetate, sodium acetate and acetic acid at a reaction temperature from 70 to 100° C.

In the next step of the reaction, an iodo pyrrole derivative of formula VIII is formed by the reaction of pyrrole derivative of the formula VII with an iodination agent. The iodination agent used for this reaction is known in the art and are for example N-iodosuccinimide, iodic acid in the presence of iodine, iodine in the presence of potassium iodide or sodium iodide, potassium iodide or sodium iodide in the presence of hydrogen peroxide. The reaction is for example carried out in an inert solvent, such as ethers, hydrocarbons or halogenated hydrocarbons preferably anhydrous dichloromethane at a reaction temperature from 0 to 40° C., preferably at room temperature in the presence of a iodination agent for example N-iodosuccinimide to yield the iodo pyrrole derivative of formula VIII. After the reaction, the product is worked-up in a manner known in the art, for example the mixture is washed with an aqueous solution of sodium thiosulphate and an aqueous solution of sodium hydrogen carbonate, dried over anhydrous sodium sulphate and finally the organic solvent was evaporated. The reaction is known in the literature for example from textbooks on organic chemistry e.g. J. March (1992), "Advanced Organic Chemistry: Reactions, Mechanisms, and Structure", $4^{th}$ ed. John Wiley & Sons or as described in Y. Murata, Bull. Chem. Soc. Jpn. 1996 (11), 3339. The use of abovementioned iodination agents is described for example in Synthesis 1995 (12), 1480, Tetrahedron 1992 (48) 44, 9661 or Liebigs Ann. Chem. 1989 (9), 863.

The iodo pyrrole derivatives of formula VIII are converted to the corresponding pyrrole thio compounds of formula IX by reaction with a disulphide compound of the formula $R^2SSR^2$ or by the reaction with a compound of the formula $R^2SX$ wherein $R^2$ is as defined above and X is a halogen, preferably chlorine (the compounds of the formula $R^2SSR^2$ and $R^2SX$ are commercially available or can be synthesized according to methods known from the art for example as described in U.S. Pat. No. 4,282,242). The reaction is conveniently carried out by treating the compound of formula VIII under nitrogen atmosphere with a strong base for example sodium hydride or preferably lithium hydride, in an inert solvent for example anhydrous dimethyl sulphoxide at a reaction temperature from 0° C. to room temperature and then reacting the mixture with the compounds of the formula $R^2SX$ or preferably with the disulphide compound of the formula $R^2SSR^2$. The reaction is preferably carried out at a reaction temperature from 40 to 60° C., yielding the compound of formula IX. After the reaction, the product is worked-up in a manner known in the art for example extracted with diethyl ether, dried over anhydrous magnesium sulphate and finally the organic solvent is evaporated.

In the next step of the reaction, the compound of formula IX is reacted with a compound of the formula $R^1X$ wherein $R^1$ is as defined above with the exception hydrogen (the compound for $R^1$ being hydrogen has already been described; see compound IX) and X represents a halogen for example bromo (commercially available or synthesized according to methods known from textbooks on organic chemistry e.g. from J. March (1992), "Advanced Organic Chemistry: Reactions, Mechanisms, and Structure", $4^{th}$ ed. John Wiley & Sons) to obtain the N-substituted compound of the formula XI. In forming the compound of formula XI, any conventional method of substitution can be utilized in carrying out this reaction. The reaction of the compounds of formulas IX is preferably carried out under nitrogen in an inert solvent for example polar aprotic solvents such as tetrahydrofuran (THF) or N,N-dimethylformamide (DMF), preferably anhydrous THF at a temperature from 0° C. to room temperature in the presence of tetra-n-butylammonium bromide and in the presence of a base such as sodium hydroxide, potassium carbonate, sodium hydride or an amine of the formula $R_3N$ wherein R is methyl, ethyl or propyl. The most preferred base is sodium hydroxide. Finally the mixture is reacted with the compound of the formula $R^1X$ to obtain the compound of formula XI.

The conversion of a compound of the formula XI to a compound of the formula Ia wherein R, $R^1$, $R^2$, $R^3$ and $R^5$ are as defined above and $R^4$ is $CH_2OH$ and X represents S, is carried in that the compound of formula XI is reduced to the compound of formula Ia by reacting it with a reducing agent such as lithium aluminum hydride. The reaction is conveniently carried out by treating the compound of formula XI under nitrogen atmosphere with a reducing agent, for example $LiAlH_4$, $LiBH_4$, $BH_3*S(CH_3)_2$, iso-$Bu_2AlH$ or Vitride®, in an inert solvent such as ethers for example anhydrous diethyl ether, THF of dioxane at a reaction temperature from 0° C. to room temperature. Preferably, the reaction is carried out with $LiAlH_4$ and ethers. Then a solution of ammonium chloride is added to yield to a compound of the formula Ia. After the reaction, the product is worked-up in a manner known in the art for example extracted with ethyl acetate, dried over anhydrous magnesium sulphate and finally the organic solvent is evaporated.

Oxidation of a compound of the formula Ia to a compound of the formula Ib wherein R, $R^1$, $R^2$, $R^3$ and $R^5$ are as defined above, $R^4$ is C(=O)H and X represents S, is carried in that the compound of formula Ia is oxidized with an oxidizing reagent such iodobenzene diacetate in the presence of 2,2, 6,6-tetramethylpiperidine N-oxide, $(COCl)_2$ in the presence of dimethyl sulfoxide (DMSO), pyridinium chlorochromate in dichloromethane or $MnO_2$ in ethers such as diethyl ether or in a halogenated hydrocarbons such as anhydrous dichloromethane or trichloromethane or in an aprotic polar solvent such as acetone and a compound of the formula Ib is obtained. The reaction is conveniently carried out by treating the compound of formula Ia under nitrogen atmosphere with an oxidizing agent, preferably iodobenzene diacetate and 2,2,6,6-tetramethylpiperidine N-oxide, in an inert solvent for example anhydrous dichloromethane at a reaction temperature from 0° C. to room temperature to yield to a compound of the formula Ib. After the reaction, the product is worked-up in a manner known in the art for example washed with solutions of sodium thiosulphate and sodium hydrogen carbonate dried over anhydrous sodium sulphate and finally the organic solvent is evaporated.

Conversion of a compound of the formula Ib to a compound of the formula Ic wherein R, $R^1$, $R^2$, $R^3$ and $R^5$ are as defined above and $R^4$ is CH(R)OH and X represents S, is carried in that the compound of formula Ib is reacted with a Grignard reagent of the formula RMgX or a reagent of the formula RLi (both compounds are commercially available or can be synthesized according to methods known from textbooks on organic chemistry e.g. from J. March (1992), "Advanced Organic Chemistry: Reactions, Mechanisms, and Structure", 4$^{th}$ ed. John Wiley & Sons) wherein R is as defined above but not hydrogen (for R being hydrogen, the synthesis has already been described; see compound of the formula Ia) and X represents a halogen for example bromo to yield to a compound of the formula Ic. The reaction is conveniently carried out by treating the compound of formula Ib under nitrogen atmosphere, in an inert solvent for example ethers such as anhydrous tetrahydrofuran (THF), diethyl ether or dioxane, preferably THF with a Grignard reagent of the formula RMgX, preferably methyl magnesium bromide at a reaction temperature from 0° C. to room temperature and then a solution of ammonium chloride is added to yield to a compound of the formula Ib. After the reaction, the product is worked-up in a manner known in the art for example extracted with ethyl acetate dried over anhydrous magnesium sulphate and finally the organic solvent is evaporated.

Compounds of the formula Ia wherein R, R$^1$, R$^2$, R$^3$ and R$^5$ are as defined above, R$^4$ is hydrogen and X represents S, are synthesized according to known methods from the art. For example the ester compounds of the formula XI are hydrolysed to the corresponding carboxylic acid according to methods known in the literature for example from textbooks on organic chemistry e.g. J. March (1992), "Advanced Organic Chemistry: Reactions, Mechanisms, and Structure", 4$^{th}$ ed. John Wiley & Sons. In a second step carboxylic acid function of the pyrrole derivative is then decarboxylated according to methods known in the art and for example described in S. F. Macdonald, J. Chem. Soc. 1952, 4176 or G. Kleinspehn, J. Am. Chem. Soc. 1954, 76, 5641.

Compounds of the formula Ia wherein R, R$^1$, R$^2$, R$^3$ and R$^5$ are as defined above, R$^4$ is alkyl and X represents S, are synthesized according to known methods from the art. For example the compounds can be synthesised through elimination reaction of a compound of the formula Ic in a two step reaction, first in the presence of CH$_3$SO$_2$Cl and Et$_3$N and secondly with a base such as potassium hydroxide or sodium hydroxide to form the corresponding alkenyl compound which is subsequently hydrogenated in the presence of hydrogen and palladium on activated coal (Pd/C) to the corresponding alkyl substituted pyrrole derivative. The reaction are all known in the literature for example from textbooks on organic chemistry e.g. J. March (1992), "Advanced Organic Chemistry: Reactions, Mechanisms, and Structure", 4$^{th}$ ed. John Wiley & Sons.

Compound of the formula I wherein R, R$^1$, R$^2$, R$^3$ and R$^5$ are as defined above and R$^4$ is C(=O)R wherein R is alkyl are synthesized according to known methods from the art. For example, the hydroxy compounds of the formula Ic are oxidised according to methods known from the art for example from textbooks on organic chemistry e.g. from J. March (1992), "Advanced Organic Chemistry: Reactions, Mechanisms, and Structure", 4$^{th}$ ed. John Wiley & Sons) to obtain the corresponding oxo derivatives.

Compounds of the formula I wherein R, R$^1$, R$^2$, R$^3$ and R$^5$ are as defined above and R$^4$ is CONR$_2$ are synthesized according to known methods from the art. For example, the ester compounds of the formula XI is hydrolysed as described above, then reacted with thionyl chloride to obtain the activated acid chloride and finally reacted with a compound of the formula HNR$_2$ wherein R is hydrogen or alkyl to obtain the corresponding amide derivative. The reaction are all known in the literature for example from textbooks on organic chemistry e.g. J. March (1992), "Advanced Organic Chemistry: Reactions, Mechanisms, and Structure", 4$^{th}$ ed. John Wiley & Sons.

Compounds of the formula I wherein R, R$^1$, R$^2$, R$^3$ R$^4$ and R$^5$ are as defined above and X is S(O) or S(O)$_2$ are synthesized according to known methods from the art. For example, the compounds of the formula I, Ia, Ib or Ic are oxidized, to obtain the corresponding oxidised thio compounds derivatives. The reaction is known in the literature for example from textbooks on organic chemistry e.g. J. March (1992), "Advanced Organic Chemistry: Reactions, Mechanisms, and Structure", 4$^{th}$ ed. John Wiley & Sons.

Compounds of the formula I wherein R, R$^1$, R$^2$, R$^3$ R$^4$ and R$^5$ are as defined above and X is O or N(alkyl) are synthesized according to known methods from the art. For example, the compounds of the formula VII are reacted with N-bromosuccinimide (NBS) to obtain the corresponding 2-substituted bromopyrrole which is further reacted with a neutral oxygen nucleophile, such as 3-methoxyphenol in the presence of Et$_3$N to obtain the corresponding oxy pyrrole derivative. To obtain the corresponding N-substituted pyrrole derivatives, the above-mentioned 2-substituted bromopyrrole is reacted with a secondary amine in a polar aprotic solvent such as N,N-dimethylformamide (DMF). The reactions are all known in the literature for example from textbooks on organic chemistry e.g. J. March (1992), "Advanced Organic Chemistry: Reactions, Mechanisms, and Structure", 4$^{th}$ ed. John Wiley & Sons or G. Cirrincione et al., Synthesis, 1997, 1169.

Compounds of the formula I wherein R, R$^1$, R$^2$, R$^3$ R$^4$ and R$^5$ are as defined above and X—R$^2$ together represent CH$_2$-aryl or CH$_2$-heterocyclyl are synthesized according to known methods from the art. For example, compounds of the formula Va

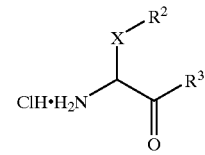

Va wherein R$^3$ is as defined above and X—R$^2$ together represent CH$_2$-aryl or CH$_2$-heterocyclyl are coupled with a β-keto ester of the formula VI wherein R$^5$ and R are as defined above (commercially available or synthesized according to methods known from textbooks on heterocyclic chemistry or organic chemistry e.g. from J. March (1992), "Advanced Organic Chemistry: Reactions, Mechanisms, and Structure", 4$^{th}$ ed. John Wiley & Sons) to form a pyrrole derivative of the formula VIIa

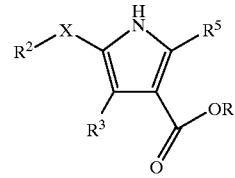

VIIa wherein R, R$^3$, R$^5$ and X—R$^2$ are as defined above. The synthesis of the pyrrole derivatives according to the Knorr synthesis of the formula VIIa is carried out in a manner known in the art. Subsequently the compound of the formula VIIa is further reacted according the above-described reactions starting with compound IX→XI→Ia→Ib→Ic.

The compounds of formula VIII are new intermediates and therefore are also an object of the present invention.

Reaction scheme 2:

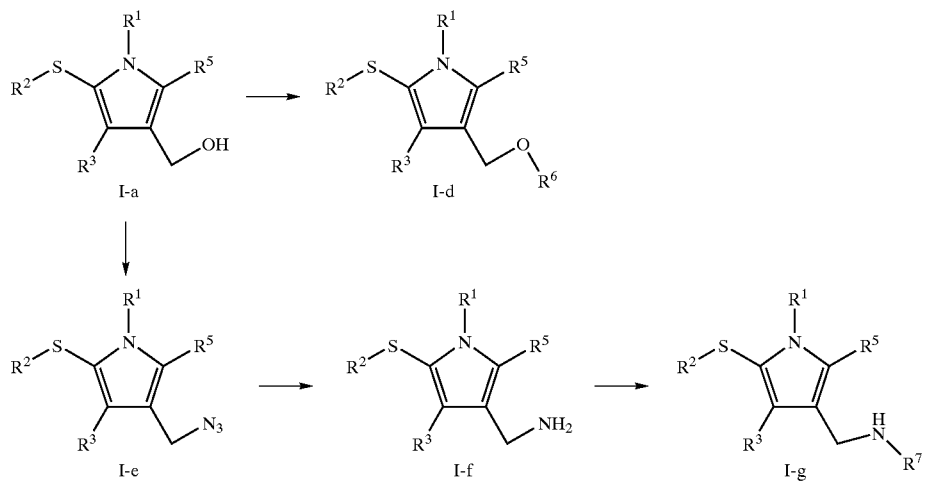

wherein $R^1$, $R^2$, $R^3$ and $R^5$ are as defined for compounds of formula I, $R^6$ is $C_{1-4}$-alkyl and $R^7$ taken together with the amino-methyl group is 2-pyridyl-carbonyl-amino-methyl, 3-pyridyl-carbonyl-amino-methyl, 4-pyridyl-carbonyl-amino-methyl, (amino-methyl)-carbonyl-amino-methyl, (phenoxy)-carbonyl-amino-methyl, (methoxy)-carbonyl-amino-methyl, (di-methyl-amino)-carbonyl-amino-methyl, (phenyl-amino)-carbonyl-amino-methyl, (amino)-carbonyl-amino-methyl, (phenyl)-carbonyl-amino-methyl, (methyl)-carbonyl-amino-methyl, methyl-carbonyl-amino-methyl-carbonyl-amino-methyl, (tert.-butyl)-carbonyl-amino-methyl-carbonyl-amino-methyl, (N1-Acetyl-O-tert.-butyl-N2-ylmethyl)-L-serinamide, (N1-Acetyl-N2-yl]methyl)-L-serinamide, [N1-(tert.-butoxycarbonyl)-O-tert.-butyl-N2-yl-methyl]-L-serinamide, methyl-sulfonyl-amino-methyl, phenyl-sulfonyl-amino-methyl or p-toluyl-sulfonyl-amino-methyl.

The primary alcohol I-a may be alkylated, acylated or reacted with isocyanates to give carbamates according to methods known from textbooks on organic chemistry e.g. from J. March (1992), "Advanced Organic Chemistry: Reactions, Mechanisms, and Structure", $4^{th}$ ed. John Wiley & Sons. These are standard reactions of which there are many combinations of reagents, for example, alkylation may be achieved using alkyl iodides, bromides, chlorides, triflates or any other suitable leaving group. Acylation may be achieved via acid chlorides or other activated carbonyl compounds such as activated carboxylic acids. Carbamates are accessible by reacting I-a with isocyanates in a standard procedure.

I-a may be further derivatised to the azide I-e using sodium azide or diphenylphosphoryl azide in standard procedures according to methods known from textbooks on organic chemistry e.g. from J. March (1992), "Advanced Organic Chemistry: Reactions, Mechanisms, and Structure", $4^{th}$ ed. John Wiley & Sons. I-e may be reduced to the primary amine I-f using hydrogenation with standard catalysts such as 10% palladium on carbon in suitable solvents, such as ethyl acetate, methanol or ethanol, or with a trialkyl or aryl phosphine.

The primary amine I-f may be alkylated, acylated, sulfonylated or reacted with isocyanates (to give ureas) to give I-g according to methods known from textbooks on organic chemistry e.g. from J. March (1992), "Advanced Organic Chemistry: Reactions, Mechanisms, and Structure", $4^{th}$ ed. John Wiley & Sons. These are standard reactions of which there are many combinations of reagents, for example, alkylation may be achieved using alkyl iodides, bromides, chlorides, triflates or any other suitable leaving group. Acylation may be achieved via acid chlorides or other activated carbonyl compounds such as activated carboxylic acids. Sulfonylation may be via sulfonyl chlorides using a base such as triethylamine, N-methyl morpholine or N-ethyl morpholine. All these reactions may be conducted in suitable solvents known to those skilled in the art, for example, dichloromethane, chloroform, dioxane, dimethyformamide, tetrahydrofuran, etc.

Ureas are accessible by reacting I-f with isocyanates in a standard procedure.

Derivatives of ester XI (reaction scheme 1), where the ester is replaced by other carbonyl groups (see reaction scheme 3), may be prepared according to reaction scheme 1 where the only change is intermediate VI for intermediate XII:

Reaction scheme 3 (additional reagents of type VI):

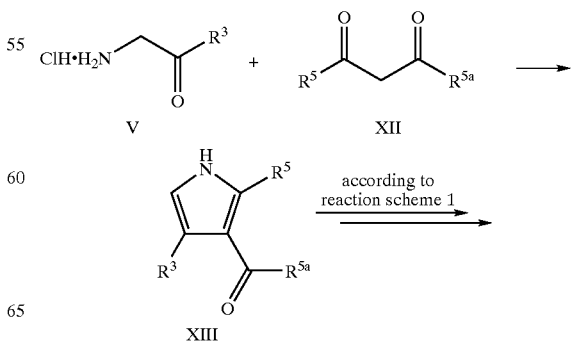

-continued

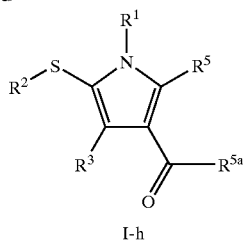

I-h wherein $R^1$, $R^2$ and $R^3$, are as defined for compounds of formula I, where $R^5$ is alkyl and $R^{5a}$, is hydrogen, amino, alkyl, alkoxy, trifluoromethyl, methyl-oxy-carbonyl or ethyl-oxy-carbonyl.

The chemistry to form the pyrrole and the subsequent reactions are as for those reactions already described in reaction scheme 1.

When $R^{5a}$=methyl, yet further derivatives of the pyrrole may be prepared according to reaction scheme 4:

Reaction scheme 4:

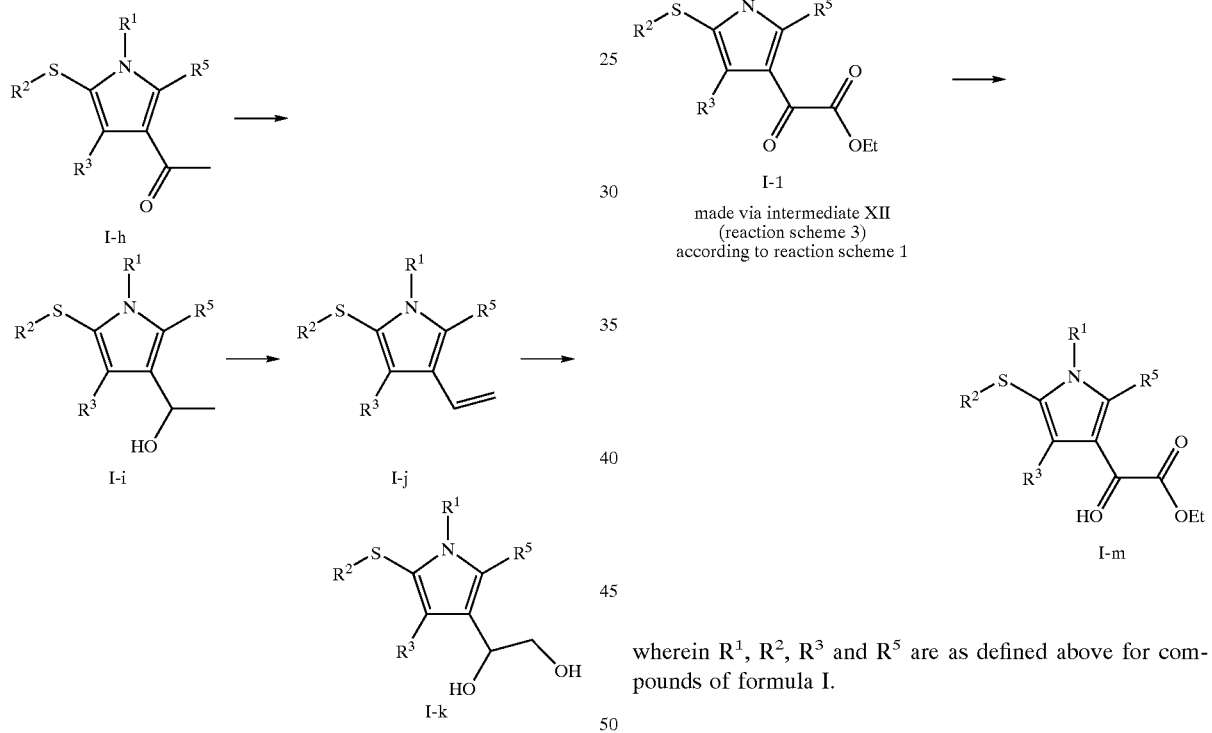

wherein $R^1$, $R^2$, $R^{3'}$ and $R^5$ are as defined for compounds of formula I.

I-h, prepared according to reaction scheme 3, may be reduced to the ethanol derivative I-i as already described. Elimination of water to form the vinyl compound I-j is achieved thermally by heating in a high boiling solvent such as DMSO, DMF, N-methyl pyrrolidinone, etc. Conversion of I-j into diol I-k may be achieved with osmium tetroxide, a standard reaction according to methods known from textbooks on organic chemistry e.g. from J. March (1992), "Advanced Organic Chemistry: Reactions, Mechanisms, and Structure", $4^{th}$ ed. John Wiley & Sons.

Ketone reduction of I-l (when $R^{5a}$=COCOOEt) to form I-m is achieved using the same chemistry as for preparation of I-i:

Reaction scheme 5:

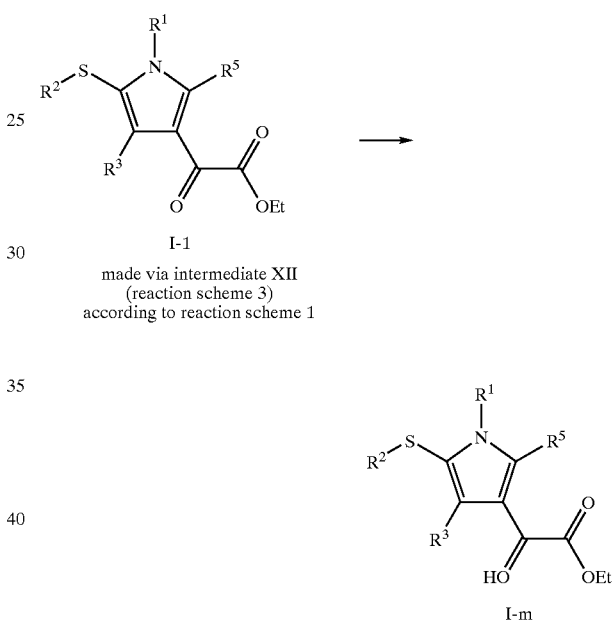

wherein $R^1$, $R^2$, $R^3$ and $R^5$ are as defined above for compounds of formula I.

The pyrrole may also be constructed using a cycloaddition reaction according to the method of Yavari, Synthetic Communications, 1996, 4495–4500 (reaction scheme 6).

Reaction scheme 6:

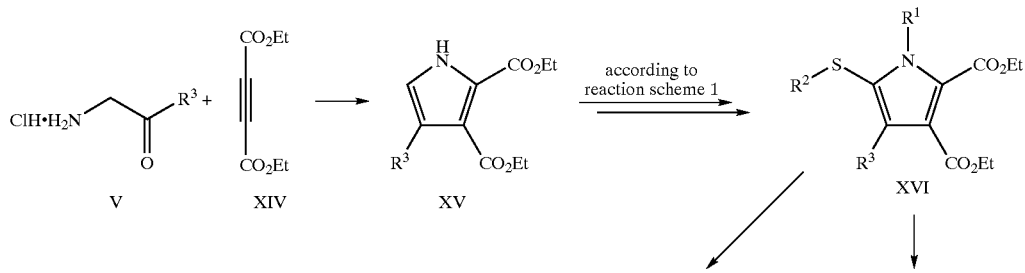

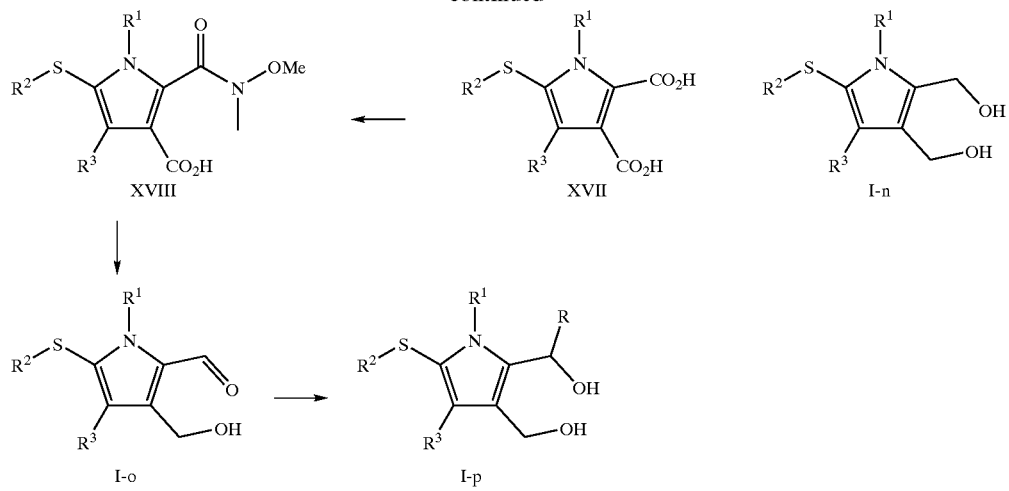

wherein $R^1$, $R^2$ and $R^3$ are as defined above for compounds of formula I.

In reaction scheme 6, the amino ketone V is reacted with diethylacetylene dicarboxylate of formula XIV in sodium acetate in refluxing ethanol to give an intermediate which is cyclised with acid giving XV. Other acetylenic esters may be used such as methyl, benzyl or aryl in a range of alcoholic solvents such as propanol or butanol.

be derivatised with N,O-dimethyl hydroxylamine according to intermediate III (see Reaction Scheme 1) to give the amide XVIII. Reduction of this amide and the ester in XVIII with lithium aluminum hydride (as above for the synthesis of I-n) gives aldehyde I-o. Grignard addition to the aldehyde in I-o gives compounds I-p, using the same method as for the synthesis of I-c (reaction scheme 1).

Reaction scheme 7:

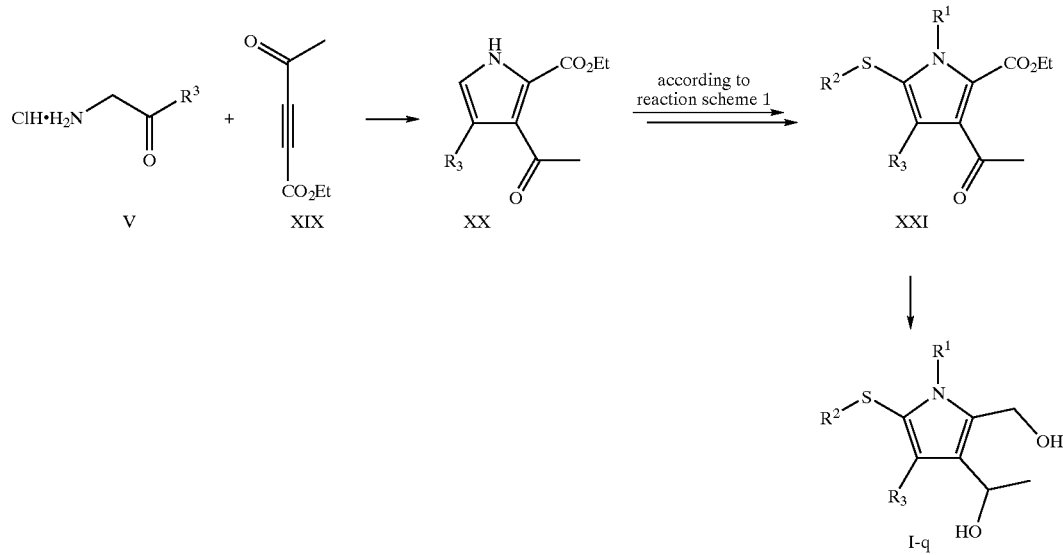

Intermediate XV may be converted to XVI according to methods already described in reaction scheme 1.

Reduction of both esters in XVI to give I-n may be accomplished according to the preparation of 1a from X1 (see Reaction Scheme 1), preferably with lithium aluminum hydride in ether.

Using basic hydrolysis, the 2-position ester may be selectively cleaved to give carboxylic acid XVII. Any strong mineral base is suitable for this purpose, preferably hydroxide ions (sodium or potassium hydroxide), in an alcoholic solvent such as ethanol, propanol, butanol. XVII may then wherein $R^1$, $R^2$ and $R^{3'}$ are as defined for compounds of formula I.

Preparation of intermediate XX may be constructed using a cycloaddition reaction according to the method of Yavari, Synthetic Communications, 1996, 4495–4500 (Scheme 2a), as for intermediate XV.

Reduction of the ester and ketone in XXI to give I-q may be accomplished with lithium aluminum hydride in ether, as for I-p and I-a.

Reaction scheme 8:

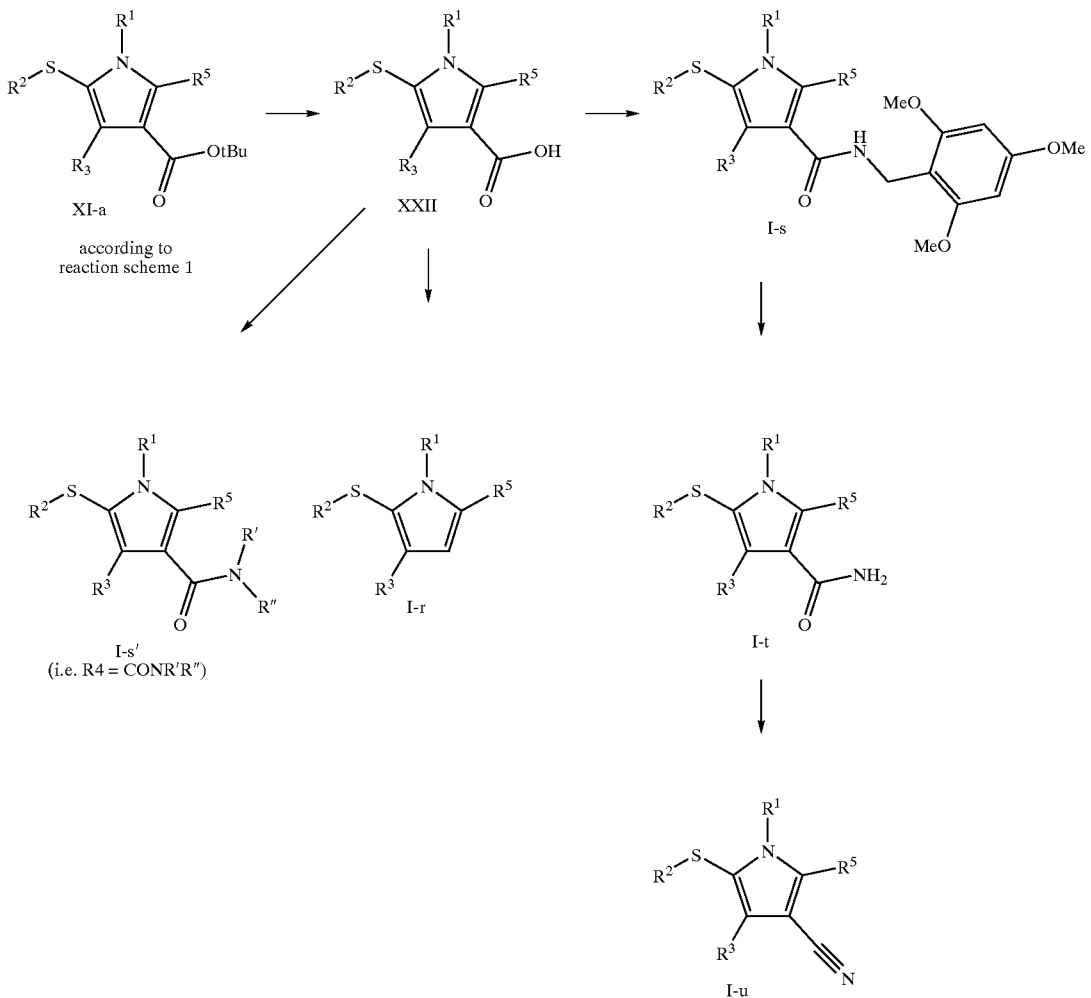

wherein $R^1$, $R^2$, $R^{3'}$ and $R^5$ are as defined for compounds of formula I.

Tert.-butyl ester XI-a (prepared according to reaction scheme 1) may be hydrolysed using methods known in the art, such as trifluoroacetic acid in dichloromethane, to give the carboxylic acid XXII, a versatile intermediate which may be either thermally decarboxylated to I-r or derivatised further to amide I-s. Similar amide bond formations of XXII may be carried out with a variety of amines to give amides I-s' where, R' and R" are defined above. Treatment of I-s with trifluoroacetic acid in dichloromethane reveals the primary amide I-t. Dehydration of I-t to give I-u may be achieved with Lawessons reagent according to Cava, Michael P.; Levinson, Matthew I Tetrahedron (1985), 41(22), 5061–87, which gives the nitrile.

Reaction scheme 9:

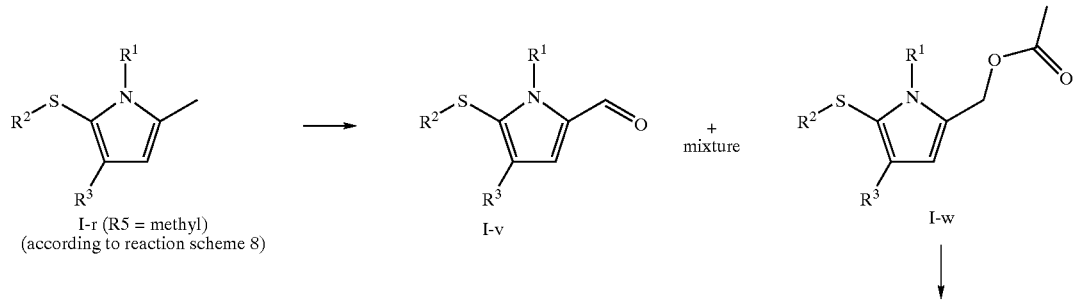

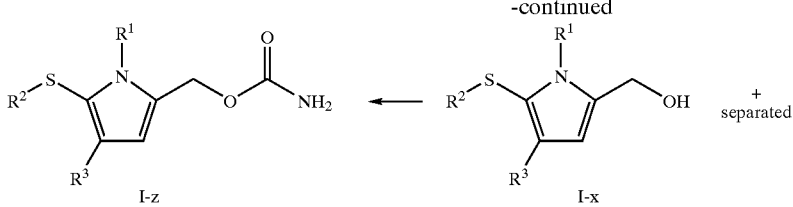

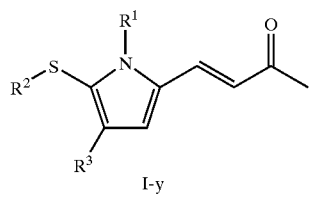

wherein $R^1$, $R^2$ and $R^{3'}$ are as defined for compounds of formula I.

In reaction scheme 9, compound I-r ($R^5$=methyl, synthesized according to reaction scheme 8), may be oxidised with lead tetraacetate to give a mixture of the aldehyde I-v and acetate I-w. Lead tetraacetate is a well known oxidant to those skilled in the art but other oxidants, such as potassium permanganate may also be used to oxidise aromatic methyl groups as in I-r.

Acetate I-w (crude) may then be hydrolysed to primary alcohol I-x using any method known in the art, such as alkaline hydrolysis with sodium or potassium hydroxide. On purification the by-product I-y was isolated. Alcohol I-x may then be derivatised to the primary carbamate I-z using trichloroacetyl isocyanate. The starting alcohol may be conveniently dissolved in a suitable organic solvent such as dichloromethane or chloroform and the reagent trichloroacetyl isocyanate added keeping the reaction temperature below 5 degrees but above −10 degrees. The work up involves use of bases such as sodium or potassium carbonate followed by purification using standard procedures. Other methods known in the art are not effective in this transformation, such as chlorosulfonyl isocyanate or trimethylsilyl isocyanate.

Reaction scheme 10:

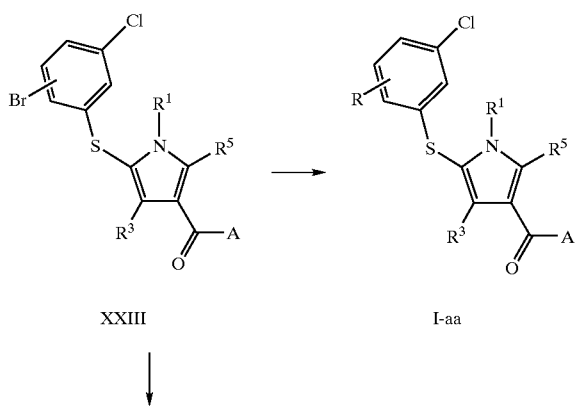

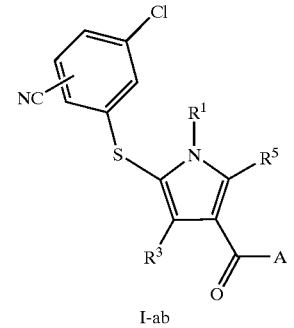

wherein $R^1$, $R^3$ and $R^5$ are as defined for compounds of formula I, A is Cl-4-alkoxy or amino and R is $C_{1-4}$-alkyl.

In reaction scheme 10, intermediate XXIII (synthesized according to reaction scheme 1 using 3-bromo-5-chlorophenyldisulfide) may be transformed to I-aa using sp2-sp2 coupling reactions known to persons skilled in the art (e.g. from J. March (1992), "Advanced Organic Chemistry: Reactions, Mechanisms, and Structure", $4^{th}$ ed. John Wiley & Sons). Such reactions are typically catalysed by a suitable palladium species such as tetrakis(triphenylphosphine) palladium, palladium acetate or dibenylideneacetone palladium. Nitrile groups may be installed using the reactivity of the aryl bromide XXIII using copper (I) cyanide to give I-ab. This reaction may also be performed on the aryl dibromide to give the aryl dinitrile.

Reaction scheme 11:

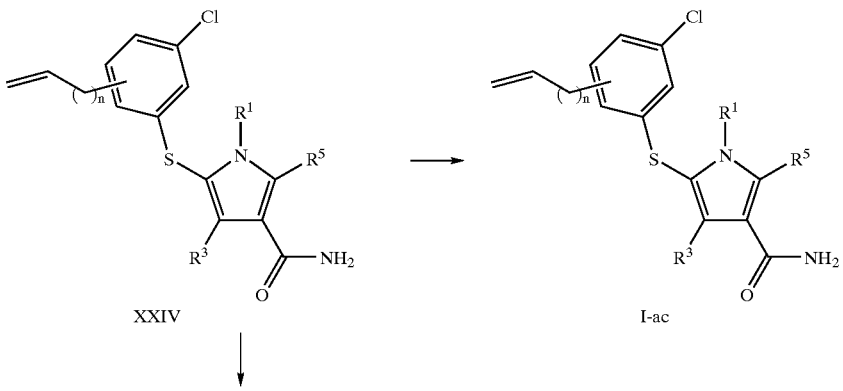

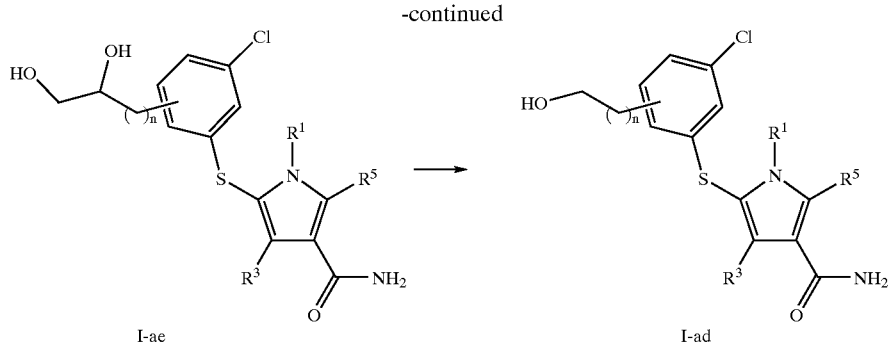

wherein $R^1$, $R^3$ and $R^5$ are as defined for compounds of formula I and n is 0 or 1.

In reaction scheme 11, intermediate XXIV, a subset of XXIII, may be reduced to the saturated alkyl chain I-ac by palladium catalysed hydrogenation. Oxidation of XXIV via osmium catalysed dihydroxylation gives I-ae. Sodium periodate cleavage of I-ae gives alcohol I-ad, according to standard procedures well known in the art.

The following assay protocols were used to measure the enzyme inhibition and antiviral activity of the compounds of the invention.

HIV-1 Reverse Transcriptase Assay: Inhibitor $IC_{50}$ Determination.

HIV-1 RT assay was carried out in 96-well Millipore filtermat NOB50 plates using purified recombinant enzyme and a poly(rA)/oligo(dT)$_{16}$ template-primer in a total volume of 50 μL. The assay constituents were 50 mM Tris/HCl, 50 mM NaCl, 1 mM EDTA, 6 mM MgCl$_2$, 5 μM dTTP, 0.1 μCi [$^3$H] dTTP, 5 μg/ml poly (rA) pre annealed to 2.5 μg/ml oligo (dT)$_{16}$ and a range of inhibitor concentrations in a final concentration of 10% DMSO. Reactions were initiated by adding 5 nM HIV-1 RT and after incubation at 37° C. for 30 min, they were stopped by the addition of 50 μl ice cold 20% TCA and allowed to precipitate at 4° C. for 30 min. The precipitates were collected by applying vacuum to the plate and sequentially washing with 2×200 μl of 10% TCA and 2×200 μl 70% ethanol. Finally the plates were dried and radioactivity counted in a Wallac Microbeta 1450 after the addition of 15 μl scintillation fluid per well. $IC_{50}$'s were calculated by plotting % inhibition versus $\log_{10}$ inhibitor concentrations.

Antiviral Assay Method

Anti-HIV antiviral activity was assessed using an adaptation of the method of Pauwels et al. {Pauwels et al., 1988, J Virol Methods 20:309-321}. The method is based on the ability of compounds to protect HIV-infected T lymphoblastoid cells (MT4 cells) from cell-death mediated by the infection. The endpoint of the assay was calculated as the concentration of compound at which the cell viability of the culture was preserved by 50% ('50% inhibitory concentration', $IC_{50}$). The cell viability of a culture was determined by the uptake of soluble, yellow 3-[4,5-dimethylthiazol-2-yl]-2,5-diphenyltetrazolium bromide (MTT) and its reduction to a purple insoluble formazan salt. After solubilization, spectrophotometric methods were employed to measure the amount of formazan product.

MT4 cells were prepared to be in logarithmic-phase growth and a total of 2×10$^6$ cells infected with the HXB2-strain of HIV at a multiplicity of 0.0001 infectious units of virus per cell in a total volume of between 200–500 microliters. The cells were incubated with virus for one h at 37° C. before removal of virus. The cells are then washed in 0.01 M phosphate buffered saline, pH 7.2 before being resuspensed in culture medium for incubation in culture with serial dilutions of test compound. The culture medium used was RPMI 1640 without phenol red, supplemented with penicillin, streptomycin, L-glutamine and 10% fetal calf serum (GM10).

Test compounds were prepared as 2 mM solutions in dimethyl sulphoxide (DMSO). Four replicate, serial 2-fold dilutions in GM10 were then prepared and 50 microliters amounts placed in 96-well plates over a final nanomolar concentration range of 625–1.22. Fifty microliters GM10 and 3.5×10$^4$ infected cells were then added to each well. Control cultures containing no cells (blank), uninfected cells (100% viability; 4 replicates) and infected cells without compound (total virus-mediated cell death; 4 replicates) were also prepared. The cultures were then incubated at 37° C. in a humidified atmosphere of 5% $CO_2$ in air for 5 d.

A fresh solution of 5 mg/mL MTT was prepared in 0.01 M phosphate buffered saline, pH 7.2 and 20 microliters added to each culture. The cultures were further incubated as before for 2 h. They were then mixed by pipetting up and down and 170 microliters of Triton X-100 in acidified isopropanol (10% v/v Triton X-100 in 1:250 mixture of concentrated HCl in isopropanol). When the formazan deposit was fully solubilized by further mixing, the absorbance (OD) of the cultures was measured at 540 nm and 690 nm wavelength (690 nm readings were used as blanks for artifacts between wells). The percent protection for each treated culture was calculated using the equation:

$$\% \text{ Protection} = \frac{(OD \text{ drug-treated cultures}) - (OD \text{ untreated virus control cultures})}{(OD \text{ uninfected cultures}) - (OD \text{ untreated virus control cultures})} \times 100\%$$

In the assay, compounds of the formulas I range in activity from an $IC_{50}$ of about 0.5 to about 5000 nM, with preferred compounds having a range of activity from about 0.5 to about 750 nM, more preferably about 0.5 to 300 nM, and most preferably about 0.5 to 50 nM.

| Biological Activity Table | | |
|---|---|---|
| Structure | RT IC$_{50}$/nM | HIV IC$_{50}$/nM |
| (3,5-dichlorophenylthio, N-(pyridin-3-ylmethyl), 5-methyl, 3-isopropyl, 4-hydroxymethyl pyrrole) | 79 | 17.5 |
| (3,5-dichlorophenylthio, N-methyl, 5-methyl, 3-isopropyl, 4-hydroxymethyl pyrrole) | 930 | 580 |
| (3-chlorophenylthio, N-(thiazol-4-ylmethyl), 5-methyl, 3-isopropyl, 4-hydroxymethyl pyrrole) | 4120 | ND |
| (phenylthio, N-(pyridin-4-ylmethyl), 5-methyl, 3-isopropyl, 4-hydroxymethyl pyrrole) | 260 | 11.5 |
| (2-chloro-4-fluorophenylthio, N-(pyridin-4-ylmethyl), 5-methyl, 3-isopropyl, 4-hydroxymethyl pyrrole) | 5430 | ND |

-continued
Biological Activity Table
| Structure | RT IC$_{50}$/nM | HIV IC$_{50}$/nM |
|---|---|---|
| 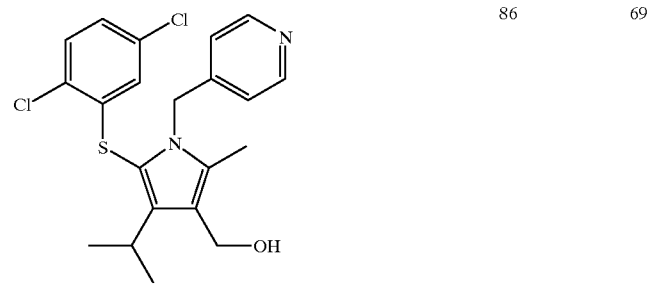 | 86 | 69 |
| 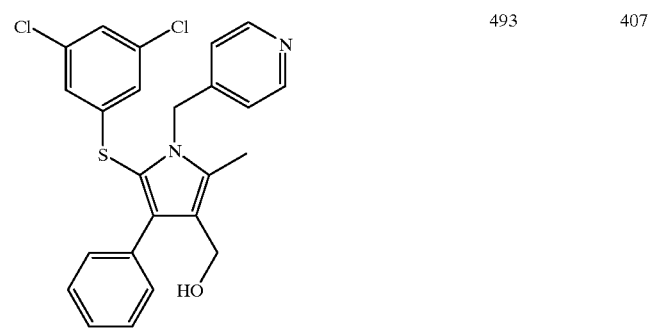 | 493 | 407 |
| 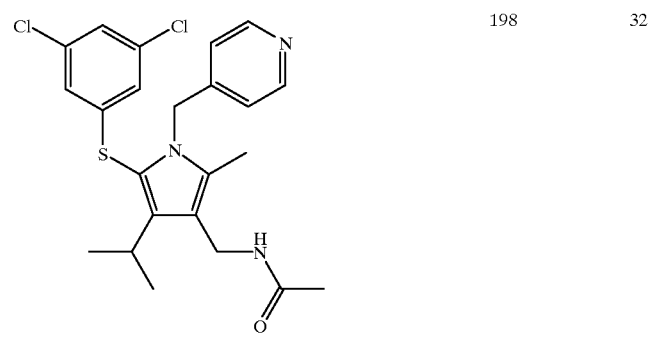 | 198 | 32 |
| 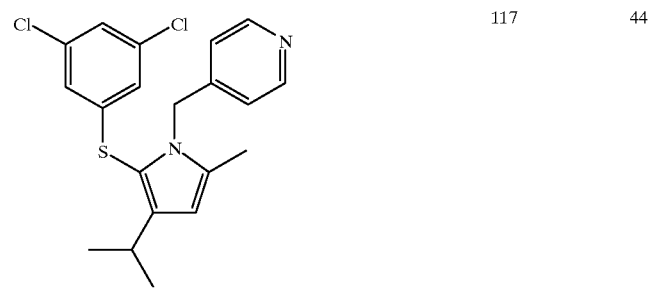 | 117 | 44 |

-continued

Biological Activity Table

| Structure | RT IC$_{50}$/nM | HIV IC$_{50}$/nM |
|---|---|---|
| [structure] | 91 | 16 |
| [structure] | 90 | ND |
| [structure] | 658 | 91 |
| [structure] | 289 | 183 |
| [structure] | 972 | ND |

-continued

Biological Activity Table

| Structure | RT IC$_{50}$/nM | HIV IC$_{50}$/nM |
|---|---|---|
| 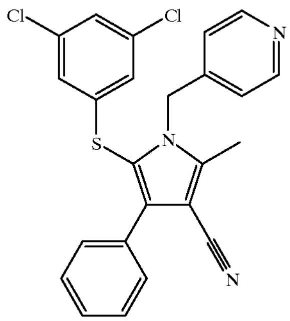 | 2450 | ND |
| 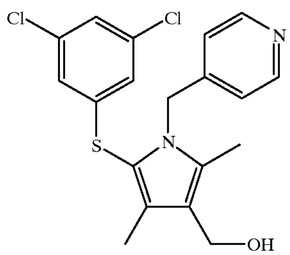 | 287 | 49 |
| 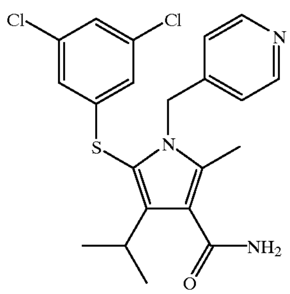 | 150 | 22 |
| 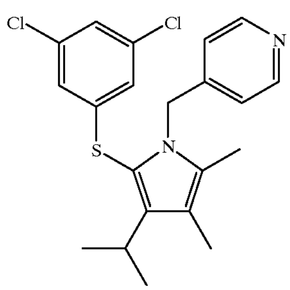 | 125 | 94 |
| 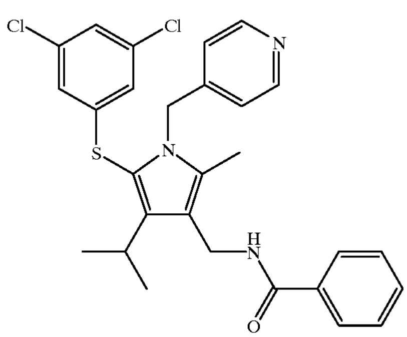 | 283 | 84 |

Biological Activity Table

| Structure | RT IC$_{50}$/nM | HIV IC$_{50}$/nM |
|---|---|---|
| (structure) | 33 | 16 |
| (structure) | 43 | 11 |
| (structure) | 272 | 110 |
| (structure) | 60 | 10 |

ND = not determined

It will be understood that references herein to treatment extend to prophylaxis as well as to treatment of existing conditions. It will also be understood that references to the treatment of animals includes the treatment of humans as well as other mammals.

In the present specification "comprise" means "includes" and "comprising" means "including".

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The pyrrole derivatives provided by the present invention can be used together with a therapeutically inert carrier as medicaments in the form of pharmaceutical preparations. The pharmaceutical preparations can be administered enterally, such as orally, in the form of tablets, coated tablets, dragees, hard and soft gelatine capsules, solutions, emulsions or suspensions, or nasally, e.g. in the form of nasal sprays. They can also be administered rectally, e.g. in the form of suppositories, or parenterally, (e.g. intramuscularly, intravenously, or subcutaneously), for example, in the form of injection solutions.

For the manufacture of pharmaceutical preparations the pyrrole derivatives can be formulated with therapeutically inert, inorganic or organic carriers.

Lactose, corn starch or derivatives thereof, talc, stearic acid or its salts can be used, for example, as such carriers for tablets, coated tablets, dragees and hard gelatine capsules.

Suitable carriers for soft gelatine capsules are, for example, vegetable oils, waxes, fats, semi-solid and liquid polyols and the like.

Suitable carriers for the manufacture of injection solutions are, for example, water, saline, alcohols, polyols, glycerine, vegetable oils and the like. Natural or hardened oils, waxes, fats, semi-liquid or liquid polyols and the like are suitable carriers for the manufacture of suppositories. The pharmaceutical preparations of the present invention may also be provided as sustained release formulations or other appropriate formulations.

The pharmaceutical preparations can also contain preservatives, solubilizers, stabilizers, wetting agents, emulsifiers, sweeteners, colorants, flavourants, salts for adjustment of the osmotic pressure, buffers, masking agents or antioxidants.

The pharmaceutical preparations may also contain other therapeutically active agents such as those mentioned above.

The dosage can vary within wide limits and will, of course, be adjusted to the individual requirements in each particular case.

Dosage levels of between about 0.01 and about 100 mg/kg body weight per day in monotherapy and/or in combination therapy are commonly administered from about I to 5 times per day. A typical preparation will contain from about 5% to 95% active compound (w/w) . The daily dosage can be administered as a single dosage or in divided dosages.

The pyrrole derivatives provided by the present invention or the medicaments thereof may be for use in monotherapy and/or combination therapy, i.e. the treatment may be in conjunction with the administration of one or more additional therapeutically active substance(s). When the treatment is combination therapy, such administration may be concurrent or sequential with respect to that of the pyrrole derivatives of the present invention. Thus, concurrent administration, as used herein, includes administration of the agents in conjunction or combination, together, or before or after each other.

It will be understood that references herein to treatment extend to prophylaxis as well as to treatment of existing conditions. Treatment of a disease or condition, as used herein, also includes preventing, inhibiting, regressing, reversing, alleviating or relieving the disease or condition, or the clinical symptoms thereof. The term "subject" as used herein refers to animals, including humans and other mammals.

EXAMPLES

With regard to the starting materials that are known compounds some of these may be purchased from commercial suppliers. Other starting materials that are known and their analogues can be prepared by methods well known in the art. Examples of compounds available from commercial suppliers, and citations to the synthesis of other compounds and their analogues are provided in the Examples below.

The described NMR spectra were recorded on a Bruker DRX 400 MHz spectrometer with the probe temperature set at 300 K.

The mass spectra indicated by "(M+; EI)", were recorded under electron impact conditions (EI), on a THERMO-QUEST MAT95 S with a source temperature of 200° C. Other mass spectra were recorded under electrospray ionization spectra (ESI) conditions, on one of the following machines:

a) THERMOQUEST SSQ 7000 [Solvent 0.085% TFA in 90% Acetonitrile/water; flow rate 100 microliters/minute; capillary 250° C.; spray voltage 5 KV; sheath gas 80 psi], or b) LC-MS system (liquid chromatograph coupled to mass spectrum) THERMOQUEST TSQ 7000 ELECTROSPRAY or MICROMASS PLATFORM ELECTROSPRAY [Solvent 0.1% TFA in water or 0.085% TFA in 90% acetonitrile/water or 0.085% TFA in acetonitrile].

In the following examples the abbreviations used have the following significations:

min minute(s)
h hour(s)
d day(s)
EDAC 1-Ethyl-3-(3-dimethylaminopropyl)-carbodiimide hydrochloride
HOBt 1-Hydroxybenzotriazole The following examples illustrate the present invention:

Example 1

5-(3,5-Dichlorophenylthio)-4-isopropyl-2-methyl-1-[(4-pyridyl)methyl]-1H-pyrrole-3-methanol A solution containing 0.1 g of ethyl 5-(3,5-dichlorophenylsulphanyl)-4-isopropyl-2-methyl-1-pyridin-4-yl-1H-pyrrole-3-carboxylate in 0.5 ml of anhydrous diethyl ether was added dropwise to 0.54 ml of a 1M solution of lithium aluminum hydride which was stirred and cooled at 0–5° C. The mixture was stirred at 5° C. for 1 h then at room temperature for 1 h. The mixture was cooled again to 5° C. and quenched with saturated ammonium chloride solution, then extracted three times with 10 ml of ethyl acetate. The combined extracts were washed with 10 ml of brine, then dried over anhydrous magnesium sulphate, filtered and evaporated. The residue was purified by flash chromatography on silica gel using methanol/dichloromethane (1:19) for the elution to give 70 mg of 5-(3,5-dichlorophenylthio)-4-isopropyl-2-methyl-1-[(4-pyridyl)methyl]-1H-pyrrole-3-methanol as a pale orange gum. Mass spectrum (ESI) m/z 421 $[M+H]^+$. $^1H$ NMR ($CDCl_3$) 1.31 (d, 6H), 2.21 (s, 3H), 3.24 (m, 1H), 4.66 (s, 2H), 5.10 (s, 2H), 6.68 (d, 2H), 6.74 (m, 2H), 6.98 (t, 1H), 8.44 (m, 2H).

The starting material ethyl 5-(3,5-dichlorophenylsulphanyl)-4-isopropyl-2-methyl-1-pyridin-4-yl-1H-pyrrole-3-carboxylate was prepared as follows:

A) A solution containing 18.8 g of N-tert.-butoxycarbonylglycine in 180 ml of anhydrous dichloromethane was stirred under nitrogen and cooled at 0–5° C. while 11.5 g of N,O-dimethylhydroxylamine hydrochloride, 27.1 g of N-ethylmorpholine and 22.5 g of N-ethyl-N'-(3-dimethylaminopropyl)carbodiimide hydrochloride were added. The mixture was allowed to warm slowly to room temperature and stirred for 16 h. The mixture was washed twice with 150 ml of 1M hydrochloric acid, and 150 ml of saturated sodium hydrogen carbonate then dried over anhydrous sodium sulphate, filtered and evaporated to give 22.5 g of N-tert.-butoxycarbonylglycine N-methyl-N-methoxyamide as a white solid which was used without further purification.

B) A solution of 10.9 g of N-tert.-butoxycarbonylglycine N-methyl-N-methoxyamide in 300 ml of anhydrous tetrahydrofuran and 100 ml of anhydrous diethyl ether was cooled at 0–5° C. while 100 ml of a 2M solution of isopropyl magnesium chloride in tetrahydrofuran was added slowly. The mixture was stirred at 0–5° C. for 4 h then poured into 1.5 liter of 1M hydrochloric acid. The product was extracted with three portions of 500 ml diethyl ether. Combined extracts were washed with 500 ml brine then dried over anhydrous magnesium sulphate, filtered and evaporated to give 8.38 g of 4-tert.-butoxycarbonylamino-2-methyl-3-butanone as a colourless oil which was used without further purification.

C) 7.03 g of 4-tert.-butoxycarbonylamino-2-methyl-3-butanone was added to 80 ml of an ice cold 4M solution of hydrogen chloride in ethyl acetate. The solution was stirred at 0–5° C. for 1 h during which time a precipitate separated. The mixture was evaporated under reduced pressure and the residue triturated with anhydrous ether. The white solid product was filtered off, washed with anhydrous diethyl ether and dried to give 4.14 g of 4-amino-2-methyl-3-butanone hydrochloride.

D) A solution containing 0.32 g of 4-amino-2-methyl-3-butanone hydrochloride, 0.33 g of ethyl acetoacetate and 0.28 g of sodium acetate in 2 ml of 75% acetic acid was heated at 100° C. for 1.5 h. The mixture was poured into 10 ml of water and extracted three times with 10 ml of diethyl ether. Combined extracts were washed three times with 10 ml of saturated sodium hydrogen carbonate and with 10 ml of brine then dried over anhydrous magnesium sulphate, filtered and evaporated. The residue was purified by flash chromatography on silica gel using dichloromethane for the elution to give 0.15 g of ethyl 4-isopropyl-2-methyl-1H-pyrrole-3-carboxylate. Recrystallisation from isohexane gave analytically pure material of melting point 67–68.5° C.; mass spectrum (EI) m/z 195 [M]$^+$.

E) A solution of 1.03 g of ethyl 4-isopropyl-2-methyl-1H-pyrrole-3-carboxylate in 27 ml of anhydrous dichloromethane was treated with 2.06 g of N-iodosuccinimide and stirred at room temperature for 2 h. The mixture was diluted with a further 50 ml of dichloromethane and washed with 50 ml of saturated sodium thiosulphate solution and 50 ml of saturated sodium hydrogen carbonate solution. The dichloromethane extract was dried over anhydrous sodium sulphate then filtered and evaporated. The residue was triturated with 50 ml of petroleum ether (bp 40–60° C.). The orange solid product was filtered off and dried to give 1.32 g of ethyl 5-iodo-4-isopropyl-2-methyl-1H-pyrrole-3-carboxylate; mass spectrum (ESI) m/z 322 [M+H]$^+$.

F) A solution of 1.3 g of ethyl 5-iodo-4-isopropyl-2-methyl-1H-pyrrole-3-carboxylate in 8 ml of anhydrous dimethyl sulphoxide was stirred under nitrogen at room temperature and 39 mg of lithium hydride added followed after 10 min by 0.86 g of bis-(3,5-dichlorophenyl) disulphide. The mixture was stirred under nitrogen and heated at 60° C. for 6 h then stood at room temperature for 16 h. The mixture was diluted with 150 ml of water and extracted three times with 75 ml of diethyl ether. Combined extracts were washed with 50 ml of brine then dried over anhydrous magnesium sulphate, filtered and evaporated to give a brown gum which crystallised. Recrystallisation from methylcyclohexane gave 0.66 g of ethyl 5-(3,5-dichlorophenylsulphanyl)-4-isopropyl-2-methyl-1H-pyrrole-3-carboxylate of melting point 148–151° C.; mass spectrum (EI) m/z 371[M]$^+$.

G) A solution of 0.1 g of ethyl 5-(3,5-dichlorophenylsulphanyl)-4-isopropyl-2-methyl-1H-pyrrole-3-carboxylate in 2 ml of anhydrous tetrahydrofiran was stirred at room temperature under nitrogen and treated with 65 mg of 4-bromomethylpyridine hydrobromide, 5 mg of tetra-n-butylammonium bromide and 24 mg of powdered sodium hydroxide. The mixture was stirred at room temperature for 20 h then diluted with 20 ml of water and extracted three times with 10 ml of ethyl acetate. Combined extracts were washed with 10 ml of brine, then dried over anhydrous magnesium sulphate, filtered and evaporated. The residue was purified by flash chromatography on silica gel using ethyl acetate/isohexane (1:1) for the elution to give 0.104 g of ethyl 5-(3,5-dichlorophenylsulphanyl)-4-isopropyl-2-methyl-1-pyridin-4-yl-1H-pyrrole-3-carboxylate as a colourless gum. Mass spectrum (ESI) m/z 463 [M+H]$^+$. $^1$H NMR (CDCl$_3$) 1.32 (d, 6H), 1.40 (t, 3H), 2.45 (s, 3H), 3.61 (m 1H), 4.34 (q, 2H), 5.16 (s, 2H), 6.69 (d, 2H), 6.76 (m, 2H), 7.01 (t, 1H), 8.47 (m, 2H).

Example 2
5-(3,5-Dichlorophenylthio)-4-isopropyl-2-methyl-1-[(4-pyridyl)methyl]-1H-pyrrole-3 -carboxaldehyde A solution of 0.2 g of 3,5-dichlorophenylsulphanyl-3-hydroxymethyl-4-isopropyl-2-methyl-1-pyridin-4-yl-pyrrole and 7.5 mg of 2,2,6,6-tetramethylpiperidine N-oxide in 0.5 ml of anhydrous dichloromethane was treated with 0.17 g of iodobenzene diacetate. The mixture was stirred at room temperature for 4 h then diluted with 10 ml of dichloromethane and washed with 10 ml of saturated sodium thiosulphate and 10 ml of saturated sodium hydrogen carbonate, then dried over anhydrous sodium sulphate, filtered and evaporated. The residue was purified by flash chromatography on silica gel using methanol/dichloromethane (1:49) for the elution to give 50 mg of 5-(3,5-dichlorophenylthio)-4-isopropyl-2-methyl-1-[(4-pyridyl)methyl]-1H-pyrrole-3-carboxaldehyde as a gum. Mass spectrum (ESI) m/z 419[M+H]$^+$. $^1$H NMR (CDCl$_3$) 1.36 (d, 6H), 2.53 (s, 3H), 3.46 (m, 1H), 5.16 (s, 2H), 6.69 (d, 2H), 6.74 (m, 2H), 7.02 (t, 1H), 8.47 (m, 2H), 10.21 (s, 1H).

Example 3
5-(3,5-Dichlorophenylthio)-4-isopropyl-alpha(RS)-methyl-1-[(4-pyridyl)methyl]-1H-pyrrole-3-ethanol A solution of 90 mg of 5-(3,5-dichlorophenylsulphanyl)-4-isopropyl-2-methyl-1-pyridin-4-yl-1H-pyrrole-3-carboxaldehyde in 1 ml of anhydrous tetrahydrofuran was stirred under nitrogen and cooled at 0–5° C. while 0.21 ml of a 1.4M solution of methyl magnesium bromide in toluene/tetrahydrofuran (75:25) was added dropwise. The mixture was stirred at 0–5° C. for 2 h then diluted with 10 ml of saturated ammonium chloride solution and extracted twice with 10 ml of ethyl acetate. Combined extracts were washed with 10 ml of brine, dried over anhydrous magnesium sulphate, filtered and evaporated. The residue was purified by flash chromatography on silica gel using methanol/dichloromethane (1:19) for the elution to give 19 mg of 5-(3,5-dichlorophenylthio)-4-isopropyl-alpha(RS)-methyl-1-[(4-pyridyl)methyl]-1H-pyrrole-3-ethanol as a gum. Mass spectrum (ESI) m/z 435 [M+H]$^+$. $^1$H NMR (CDCl$_3$) 1.26 (d, 3H), 1.29 (d, 3H), 1.55 (d, 3H), 1.77 (bs, 1H), 2.30 (s, 3H), 3.30 (m, 1H), 5.08 (s, 2H), 5.25 (q, 1H), 6.67 (d, 2H), 6.71 (m, 2H), 6.97 (t, 1H), 8.43 (m, 2H).

Examples 4–9

In a manner analogous to that described in examples 1–3, starting with N-tert.-butoxycarbonylglycine (commercially available from Fluka or Aldrich), the compounds shown in table 2 were also prepared:

TABLE 2

| Example | Structure | Name | Mass Spectrum (m/z ES, +ve ion) |
|---|---|---|---|
| 4 | 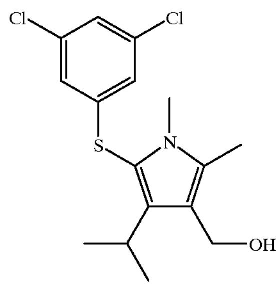 | 5-(3,5-Dichlorophenylthio)-4-isopropyl-1,2-dimethyl-1H-pyrrole-3-methanol | 344 |
| 5 | 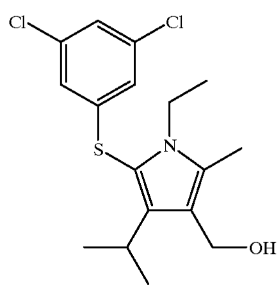 | 5-(3,5-Dichlorophenylthio)-1-ethyl-4-isopropyl-2-methyl-1H-pyrrole-3-methanol | 356 |
| 6 | 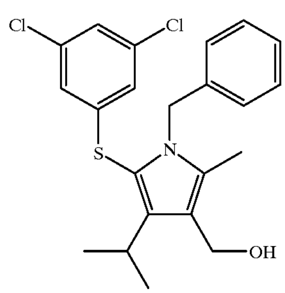 | 1-Benzyl-5-(3,5-dichlorophenylthio)-4-isopropyl-2-methyl-1H-pyrrole-3-methanol | 420 |
| 7 | 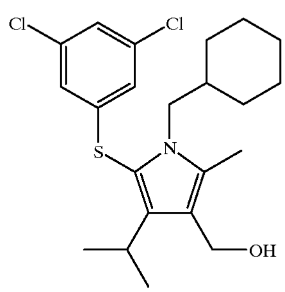 | 1-(Cyclohexylmethyl)-5-(3,5-dichlorophenylthio)-4-isopropyl-2-methyl-1H-pyrrole-3-methanol | |
| 8 | 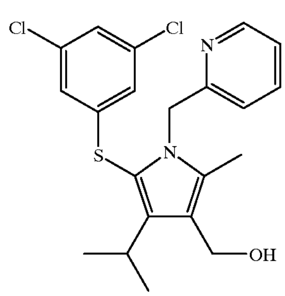 | 5-(3,5-Dichlorophenylthio)-4-isopropyl-2-methyl-1-[(2-pyridyl)methyl]-1H-pyrrole-3-methanol | 421 |

TABLE 2-continued

| Example | Structure | Name | Mass Spectrum (m/z ES, +ve ion) |
|---|---|---|---|
| 9 | 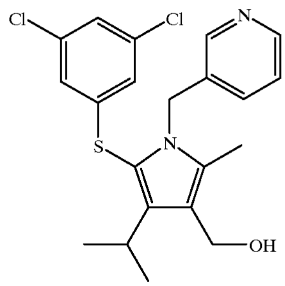 | 5-(3,5-Dichlorophenylthio)-4-isopropyl-2-methyl-1-[(3-pyridyl)methyl]-1H-pyrrole-3-methanol | 421 |

Examples 10–15

In a manner analogous to that described in examples 1–3, starting with N-tert.-butoxycarbonylglycine, the compounds shown in table 3 were also prepared:

TABLE 3

| Example | Structure | Name | Mass Spectrum (m/z ES, +ve ion) |
|---|---|---|---|
| 10 | 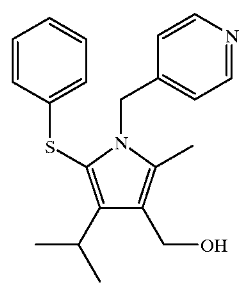 | 4-Isopropyl-2-methyl-5-phenylthio-1-[(4-pyridyl)methyl]-1H-pyrrole-3-methanol | 352 |
| 11 | 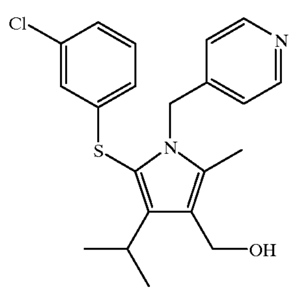 | 5-(3-Chlorophenylthio)-4-isopropyl-2-methyl-1-[(4-pyridyl)methyl]-1H-pyrrole-3-methanol | 387 |
| 12 | 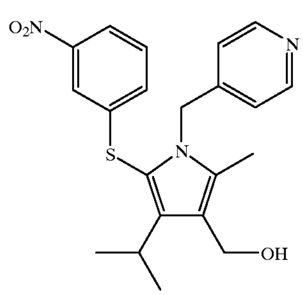 | 4-Isopropyl-2-methyl-5-(3-nitrophenylthio)-1-[(4-pyridyl)methyl]-1H-pyrrole-3-methanol | 399 |

TABLE 3-continued

| Example | Structure | Name | Mass Spectrum (m/z ES, +ve ion) |
|---|---|---|---|
| 13 | 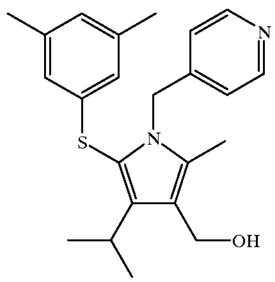 | 5-(3,5-Dimethylphenylthio)-4-isopropyl-2-methyl-1-[(4-pyridyl)methyl]-1H-pyrrole-3-methanol | 380 |
| 14 | 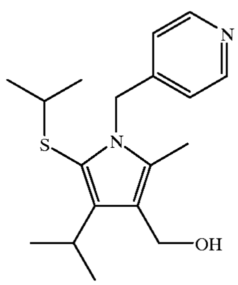 | 4-Isopropyl-5-isopropylthio-2-methyl-1-[(4-pyridyl)methyl]-1H-pyrrole-3-methanol | |
| 15 | 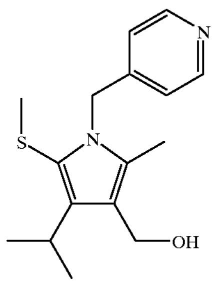 | 4-Isopropyl-2-methyl-5-methylthio-1-[(4-pyridyl)methyl]-1H-pyrrole-3-methanol | |

Examples 16–20

In a manner analogous to that described in examples 1–3, starting with N-tert.-butoxycarbonylglycine, the compounds shown in table 4 were also prepared:

TABLE 4

| Example | Structure | Name | Mass Spectrum (m/z ES, +ve ion) |
|---|---|---|---|
| 16 | 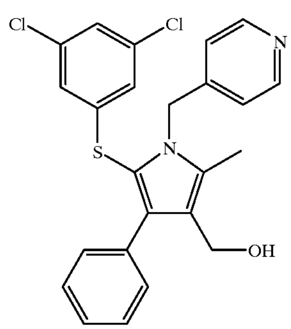 | 5-(3,5-Dichlorophenylthio)-2-methyl-4-phenyl-1-[(4-pyridyl)methyl]-1H-pyrrole-3-methanol | 455 |

TABLE 4-continued

| Example | Structure | Name | Mass Spectrum (m/z ES, +ve ion) |
|---|---|---|---|
| 17 | 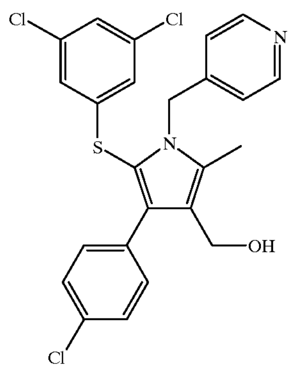 | 4-(4-Chlorophenyl)-5-(3,5-dichlorophenylthio)-2-methyl-1-[(4-pyridyl)methyl]-1H-pyrrole-3-methanol | 490 |
| 18 | 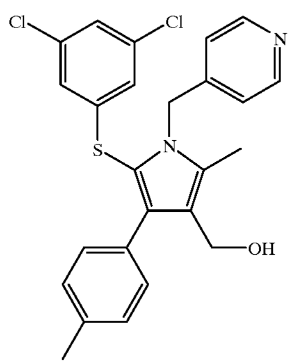 | 5-(3,5-Dichlorophenylthio)-2-methyl-4-(4-methylphenyl)-1-[(4-pyridyl)methyl]-1H-pyrrole-3-methanol | 469 |
| 19 | 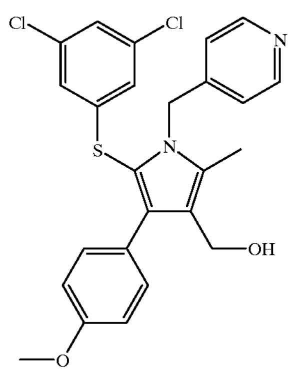 | 5-(3,5-Dichlorophenylthio)-4-(4-methoxyphenyl)-2-methyl-1-[(4-pyridyl)methyl]-1H-pyrrole-3-methanol | 485 |
| 20 | 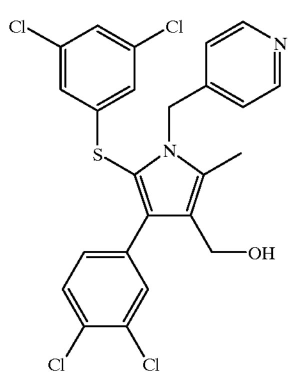 | 4-(3,4-Dichlorophenyl)-5-(3,5-dichlorophenylthio)-2-methyl-1-[(4-pyridyl)methyl]-1H-pyrrole-3-methanol | 524 |

Examples 21–22

In a manner analogous to that described in examples 1–3, starting with N-tert.-butoxycarbonylglycine converted to a compound of the formula XI, the compounds shown in table 5 were also prepared via hydrolysis of a compound of formula XI when R=tert.-butyl (example 21) or via intermediate compound XII (Scheme 3) where $R^{5a}$=amino (example 22):

TABLE 5

| Example | Structure | Name | Mass Spectrum (m/z ES, +ve ion) |
|---|---|---|---|
| 21 | (structure) | 5-(3,5-Dichlorophenylthio)-4-isopropyl-2-methyl-1-[(4-pyridyl)methyl]-1H-pyrrole-3-carboxylic acid | 435 |
| 22 | (structure) | 5-(3,5-Dichlorophenylthio)-4-isopropyl-2-methyl-1-[(4-pyridyl)methyl]-1H-pyrrole-3-carboxamide | 434 |

Example 23

In a manner analogous to that described in examples 1–3, starting with N-tert.-butoxycarbonylglycine converted to a compound of the formula Ic, the compounds shown in table 6 were prepared by mesylation reaction with for example $CH_3SO_2Cl$ and $Et_3N$ followed by a reduction reaction with for example Zn/acetic acid (as described in J. Org. Chem. 1997, 62, 9223):

Examples 24–25

In a manner analogous to that described in examples 1–3, starting with N-tert.-butoxycarbonylglycine, the compounds shown in table 7 were prepared from Ia by conversion of alcohol to chloride then displacement of chloride with azide and finally reduction of azide with hydrogen (example 24) or via nucleophilic substitution reaction with a methoxide anion (example 25) of the chloride of the alcohol of the formula Ia.

TABLE 6

| Example | Structure | Name | Mass Spectrum (m/z ES, +ve ion) |
|---|---|---|---|
| 23 | (structure) | 4-[[2-(3,5-Dichlorophenylthio)-3-isopropyl-4,5-dimethyl-1H-pyrrol-1-yl]methyl]pyridine | 405 |

TABLE 7

| Example | Structure | Name | Mass Spectrum (m/z ES, +ve ion) |
|---|---|---|---|
| 24 | 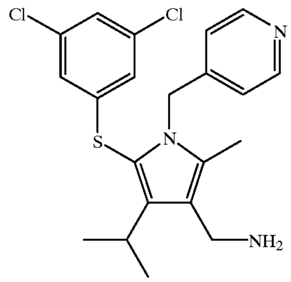 | 5-(3,5-Dichlorophenylthio)-4-isopropyl-2-methyl-1-[(4-pyridyl)methyl]-1H-pyrrole-3-methylamine | 420 |
| 25 | 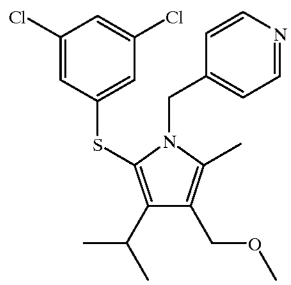 | 4-[[2-(3,5-Dichlorophenylthio)-3-isopropyl-4-(methoxymethyl)-5-methyl-1H-pyrrol-1-yl]methyl]pyridine | 435 |

Examples 26–28

In a manner analogous to that described in examples 1–3, starting with N-tert.-butoxycarbonylglycine, the compounds shown in table 8 were also prepared up to intermediate V, which was then taken forward via Reaction Scheme 6. Example 28 was prepared according to Scheme 1 where R=ethyl in intermediate VI.

TABLE 8

| Example | Structure | Name | Mass Spectrum (m/z ES, +ve ion) |
|---|---|---|---|
| 26 | 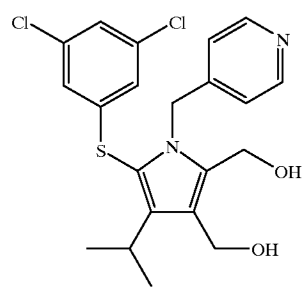 | 5-(3,5-Dichlorophenylthio)-3-(hydroxymethyl)-4-isopropyl-1-[(4-pyridyl)methyl]-1H-pyrrole-2-methanol | 437 |
| 27 | 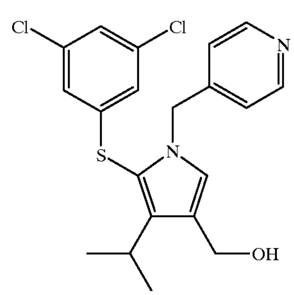 | 5-(3,5-Dichlorophenylthio)-4-isopropyl-1-[(4-pyridyl)methyl]-1H-pyrrole-3-methanol | |

TABLE 8-continued

| Example | Structure | Name | Mass Spectrum (m/z ES, +ve ion) |
|---|---|---|---|
| 28 | 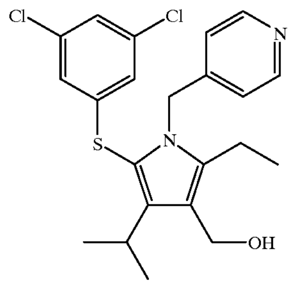 | 5-(3,5-Dichlorophenylthio)-2-ethyl-4-isopropyl-1-[(4-pyridyl)methyl]-1H-pyrrole-3-methanol | 435 |

Examples 29–30

In a manner analogous to that described in examples 1–3, starting with N-tert.-butoxycarbonylglycine, the compounds shown in table 9 were also prepared. The examples were prepared by bromination of the compounds of the formula VII to the corresponding 2-substituted bromopyrrole which was then further reacted with the corresponding neutral oxygen nucleophile in the presence of $Et_3N$ to obtain the corresponding oxy pyrrole derivative (example 29). To obtain the corresponding N-substituted pyrrole derivatives (example 30), the above-mentioned 2-substituted bromopyrrole was reacted with a primary or a secondary amine.

Examples 31–32

In a manner analogous to that described in examples 1–3, starting with N-tert.-butoxycarbonylglycine, the compounds shown in table 10 were also prepared. The examples were prepared by coupling reaction of the corresponding compounds of the formula 5a with the corresponding D-keto ester of the formula VI to obtain examples 31–32.

TABLE 9

| Example | Structure | Name | Mass Spectrum (m/z ES, +ve ion) |
|---|---|---|---|
| 29 | 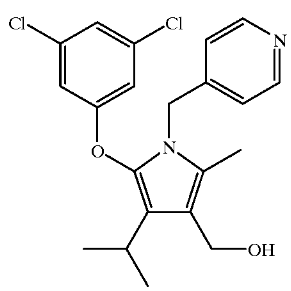 | 5-(3,5-Dichlorophenoxy)-4-isopropyl-2-methyl-1-[(4-pyridyl)methyl]-1H-pyrrole-3-methanol | |
| 30 | 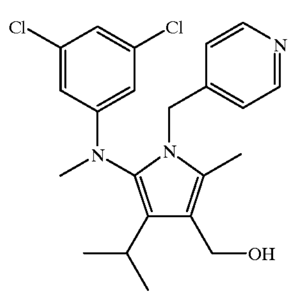 | 5-[(3,5-Dichlorophenyl)methylamino]-4-isopropyl-2-methyl-1-[(4-pyridyl)methyl]-1H-pyrrole-3-methanol | |

TABLE 10

| Example | Structure | Name | Mass Spectrum (m/z ES, +ve ion) |
|---|---|---|---|
| 31 | 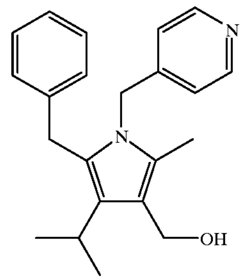 | 5-Benzyl-4-isopropyl-2-methyl-1-[(4-pyridyl)methyl]-1H-pyrrole-3-methanol | 334 |
| 32 | 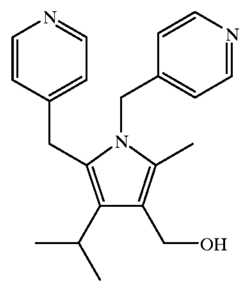 | 4-Isopropyl-2-methyl-1,5-bis[(4-pyridyl)methyl]-1H-pyrrole-3-methanol | |

Examples 33–35

In a manner analogous to that described in examples 1–3, starting with N-tert.-butoxycarbonylglycine, example 34 was made according to reaction scheme 9.

TABLE 11

| Example | Structure | Name | Mass Spectrum (m/z ES, +ve ion) |
|---|---|---|---|
| 33 | 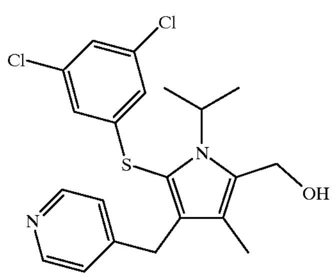 | 5-(3,5-Dichlorophenylthio)-1-isopropyl-3-methyl-4-[(4-pyridyl)methyl]-1H-pyrrole-2-methanol | |
| 34 | 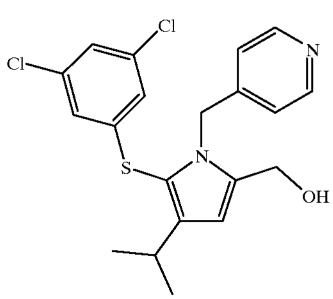 | 5-(3,5-Dichlorophenylthio)-4-isopropyl-1-[(4-pyridyl)methyl]-1H-pyrrole-2-methanol | 407 |

TABLE 11-continued

| Example | Structure | Name | Mass Spectrum (m/z ES, +ve ion) |
|---|---|---|---|
| 35 | 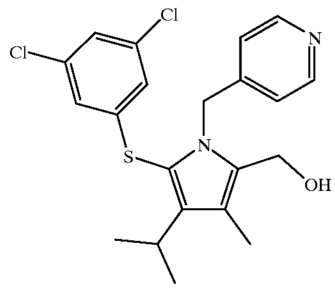 | 5-(3,5-Dichlorophenylthio)-4-isopropyl-3-methyl-1-[(4-pyridyl)methyl]-1H-pyrrole-2-methanol | |

Example 93

| Ex. | STRUCTURE | SYSTEMATIC NAME | MS |
|---|---|---|---|
| 93 | 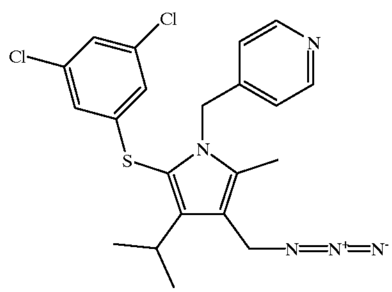 | 4-[[3-(Azidomethyl)-5-(3,5-dichlorophenylthio)-4-isopropyl-2-methyl-1-pyrrolyl]methyl]pyridine | 446 |

To a solution of 200 mg of 4-[[3-(Chloromethyl)-5-(3,5-dichlorophenylthio)-4-isopropyl-2-methyl-1-pyrrolyl]methyl]pyridine in 5mL of DMF was added 137 mg of sodium azide. The mixture was stirred at room temperature for 18 h. The yellow solution was quenched with saturated sodium bicarbonate solution and extracted with diethyl ether. The combined organic extracts were dried over anhydrous magnesium sulphate, filtered and evaporated. The residue was purified by flash chromatography on silica gel using petrol/ethyl acetate (1:2) then ethyl acetate for the elution to give 129 mg as a yellow oil. Mass spectrum (ESI) m/z 446 [M+H]+. Mass spectrum (ESI) m/z 446 [M+H]+.

Example 76

| 76 | | N-[[5-(3,5-Dichlorophenylthio)-4-isopropyl-2-methyl-1-[(4-pyridyl)methyl]-1H-pyrrol-3-yl]methyl]-4-pyridineacetamide | 525 |

To a solution of 70 mg of 5-(3,5-Dichlorophenylthio)-4-isopropyl-2-methyl-1-[(4-pyridyl)methyl]1H-pyrrole-3-methylaminein 3 mL of dichloromethane was added 30 mg of isonicotinyl chloride and 50 mg of triethylamine. The mixture was stirred at room temperature for 18 h then quenched with saturated sodium bicarbonate solution and extracted with dichloromethane. The combined organic extracts were dried over anhydrous magnesium sulphate, filtered and evaporated. The residue was preabsorbed onto silica then purified by flash chromatography on silica gel using petrol/ethyl acetate (1:9 then 1:4) for the elution to give 50 mg as a cream solid. Mass spectrum (ESI) m/z 525 [M+H]$^+$.

The starting material 5-(3,5-Dichlorophenylthio)-4-isopropyl-2-methyl-1-[(4-pyridyl)methyl]-1H-pyrrole-3-methylamine was prepared as follows:

To a solution of 2.33 g of 4-[[3-(Azidomethyl)-5-(3,5-dichlorophenylthio)-4-isopropyl-2-methyl-1-pyrrolyl]methyl]pyridinein 100 mL of ethyl acetate was added 100 mg of 10% Pd on carbon catalyst. The mixture was hydrogenated for 1.5 h. The mixture was filtered and evaporated to give 2.2 g of a yellow oil. Mass spectrum (ESI) m/z 446 [M+H]$^+$.

Example 95

To a degassed solution of 61 mg of 4-[[2-(3,5-Dichlorophenylthio)-3-isopropyl-5-methyl-4-vinyl-1-pyrrolyl]methyl]pyridine in 20 mL of dioxane and 3.5 mL of water was added 26 mg of N-methyl morpholine N-oxide and 4 mg of osmium tetroxide. The reaction was kept dark by covering with aluminum foil and stirred at room temperature for 24 h. The solution was quenched with saturated sodium bicarbonate solution and extracted with ethyl acetate. The combined organic extracts were dried over anhydrous magnesium sulphate, filtered and evaporated to give a brown gum which solidified on addition of ethyl acetate to give 29 mg of a brown solid. This solid was further purified by HPLC to give 0.4 mg of the product. Mass spectrum (ESI) m/z 451 [M+H]$^+$.

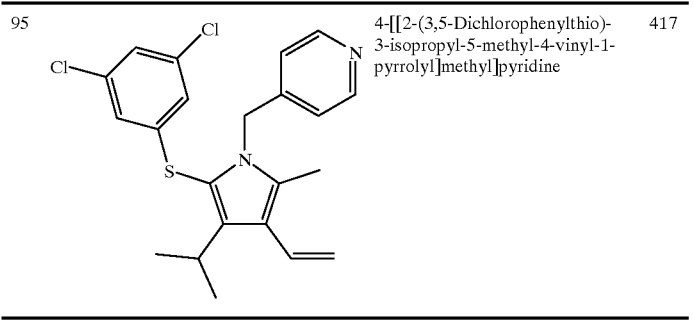

| 95 | | 4-[[2-(3,5-Dichlorophenylthio)-3-isopropyl-5-methyl-4-vinyl-1-pyrrolyl]methyl]pyridine | 417 |

A solution of 90 mg of 5-(3,5-dichlorophenylthio)-4-isopropyl-alpha(RS)-methyl-1-[(4-pyridyl)methyl]-1H-pyrrole-3-ethanol in 3 mL of DMSO was heated at 160° C. for 30 min. The brown solution was cooled to room temperature then quenched with saturated sodium bicarbonate solution and extracted with diethyl ether. The combined organic extracts were dried over anhydrous magnesium sulphate, filtered and evaporated. The residue was purified by flash chromatography on silica gel using petrol/ethyl acetate (1:4 up to 1:1) then ethyl acetate for the elution to give 28 mg as a oil. Mass spectrum (ESI) m/z 417 [M+H]$^+$.

Example 96

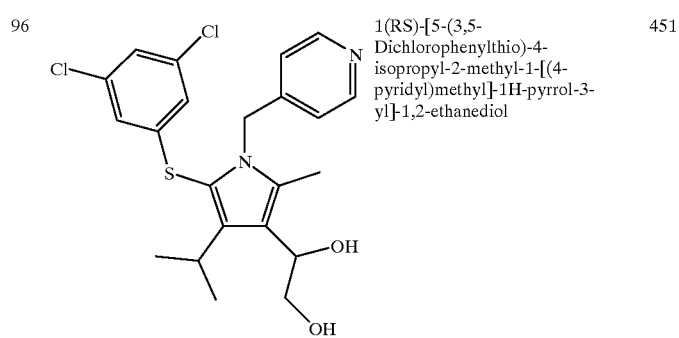

| 96 | | 1(RS)-[5-(3,5-Dichlorophenylthio)-4-isopropyl-2-methyl-1-[(4-pyridyl)methyl]-1H-pyrrol-3-yl]-1,2-ethanediol | 451 |

Example 75

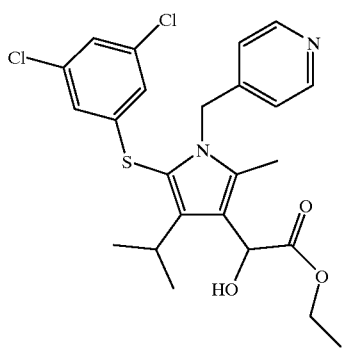

| | | |
|---|---|---|
| 75 | [5-(3,5-Dichloro-phenylsulfanyl)-4-isopropyl-2-methyl-1-pyridin-4-ylmethyl-1H-pyrrol-3-yl]-hydroxy-acetic acid ethyl ester | 493 |

To a solution of 140 mg of [5-(3,5-Dichloro-phenylsulfanyl)-4-isopropyl-2-methyl-1-pyridin-4-ylmethyl-1H-pyrrol-3-yl]-oxo-acetic acid ethyl ester in 5 mL of ethanol was added 54 mg of sodium borohydride. The mixture was stirred at room temperature for 2 h. The reaction was quenched with saturated sodium bicarbonate solution and extracted with ethyl acetate. The combined organic extracts were dried over anhydrous magnesium sulphate, filtered and evaporated. The residue was purified by flash chromatography on silica gel using petrol/ethyl acetate (1:9 up to 1:4) for the elution to give 22 mg as a white foam. Mass spectrum (ESI) m/z 493 [M+H]$^+$.

Example 107

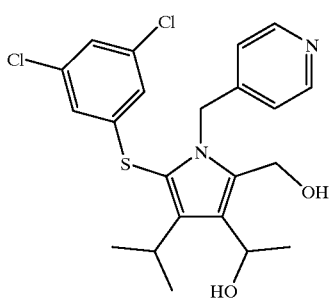

| | | |
|---|---|---|
| 107 | 5-(3,5-Dihlorophenylthio)-2-(hydroxymethyl)-4-isopropyl-alpha(RS)-methyl-1-[(4-pyridyl)methyl]-1H-pyrrole-3-ethanol | 451 |

To a solution of 120 mg of 1-[5-(3,5-Dichlorophenylthio)-4-isopropyl-2-methyl-1-[(4-pyridyl)methyl]-1H-pyrrol-3-yl]ethanone in 3 mL of ether at 0° C. was added 1.25 mL of a 1M solution of lithium aluminum hydride in ether. The reaction was allowed to warm to room temperature over 30 min. The reaction was quenched with saturated ammonium chloride solution and extracted with ethyl acetate. The combined organic extracts were washed with brine, dried over anhydrous magnesium sulphate, filtered and evaporated. The residue was purified by flash chromatography on silica gel using ethyl acetate for the elution to give 35 mg which required further purification by HPLC giving the desired product and the de-chlorinated derivative 5-(3-chlorophenylthio)-4-isopropyl-2-methyl-1-[(4-pyridyl)methyl]-1H-pyrrole-3-(2-ethanol). Mass spectrum (ESI) m/z 451 [M+H]$^+$.

The starting material 1-[5-(3,5-Dichlorophenylthio)-4-isopropyl-2-methyl-1-[(4 -pyridyl)methyl]-1H-pyrrol-3-yl]ethanone was prepared as follows:

(A) A mixture of 2.45 g of pent-2-yn-4-one-oate ethyl ester, 3.19 g of 1-amino-3-methylbutan-2-one hydrobromide and 1.44 g of sodium acetate were dissolved in 88 ml of ethanol and heated at reflux for 30 min. Then 8 ml of concentrated hydrochloric acid were added and reflux continued. After 1 h the solvent was evaporated and the residue partitioned between saturated sodium bicarbonate solution and extracted with ethyl acetate. The combined organic extracts were dried over anhydrous magnesium sulphate, filtered and evaporated. The residue was purified by flash chromatography on silica gel using petrol/ethyl acetate (1:9 up to 1:4) for the elution to give 750 mg of 4-isopropyl-1H-pyrrole-3-ethanone-2-ethyl ester as a white foam. Mass spectrum (ESI) m/z 223 [M+H]$^+$.

(B) Iodination, sulfuration and alkylation to give 5-(3,5-dichlorophenylthio)-4-isopropyl-1-[(4-pyridyl)methyl]-1H-pyrrole-3-ethanone-2-ethyl ester were all carried out according to procedures described for example in Scheme 1.

Example 108

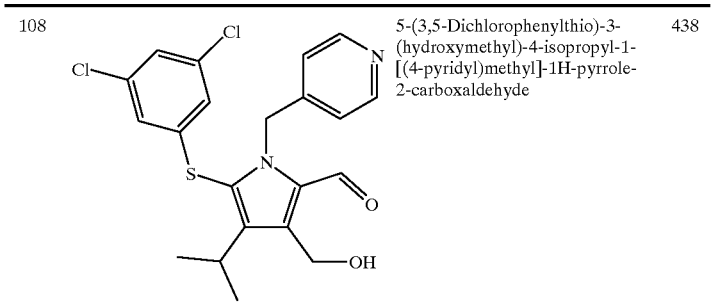

| 108 | | 5-(3,5-Dichlorophenylthio)-3-(hydroxymethyl)-4-isopropyl-1-[(4-pyridyl)methyl]-1H-pyrrole-2-carboxaldehyde | 438 |

To a solution of 88 mg of 5-(3,5-dichlorophenylthio)-4-isopropyl-3-ethyl ester-1-[(4-pyridyl)methyl]-1H-2-[N-methyl-N-methoxyamide]-pyrrole in 5mL of THF at 0° C. was added 0.33 mL of a 1M solution of lithium aluminum hydride in ether. The reaction was allowed to warm to room temperature over 1 h. The reaction was quenched with saturated ammonium chloride solution and extracted with ethyl acetate. The combined organic extracts were washed with brine, dried over anhydrous magnesium sulphate, filtered and evaporated. The residue was purified by flash chromatography on silica gel using petrol/ethyl acetate (1:2) for the elution to give the desired product, 29 mg of an oil, and 6 mg of 5-(3,5-Dichlorophenylthio)-4-isopropyl-1-[(4-pyridyl)methyl]-1H-pyrrole-2,3-dicarboxaldehyde as an oil. Mass spectrum (ESI) m/z 438 [M+H]$^+$.

The starting material 5-(3,5-dichlorophenylthio)-4-isopropyl-3-ethyl ester-1-[(4-pyridyl)methyl]-2-[N-methyl-N-methoxyamide]-1H-pyrrole was prepared as follows:

(A) A mixture of 0.5 g of amino-3-methylbutan-2-one hydrochloride, 0.58 ml of diethylacetylene dicarboxylate and 295 mg of sodium acetate were refluxed in 18 ml of ethanol for 10 min. A few drops of concentrated hydrochloric acid were then added and the mixture boiled further. The reaction was cooled to room temperature then partitioned between dichloromethane and ice water. The combined organic extracts were dried over anhydrous magnesium sulphate, filtered and evaporated. The residue was purified by flash chromatography on silica gel using petrol/ethyl acetate (1:9, 1:6 then 1:4) then ethyl acetate for the elution to give 323 mg of 4-isopropyl-2,3-dicarboxylate ethyl ester as a yellow oil. Mass spectrum (ESI) m/z 253 [M+H]$^+$.

(B) Iodination, sulfuration and alkylation to give 5-(3,5-dichlorophenylthio)-4-isopropyl-1-[(4-pyridyl)methyl]-1H-pyrrole-2,3-bisethyl ester were all carried out according to procedures described for example in Scheme 1.

(C) To a solution of 462 mg of 5-(3,5-dichlorophenylthio)-4-isopropyl-1-[(4-pyridyl)methyl]-1H-pyrrole-2,3-bisethyl ester in 12 mL of ethanol was added 50 mg of potassium hydroxide. The mixture was refluxed for 18 h then a further 20 mg of potassium hydroxide was added and refluxing continued for 3 h. The solvent was evaporated and the residue partitioned between ethyl acetate and dilute hydrochloric acid. The aqueous phase was extracted with ethyl acetate and the combined organic extracts were dried over anhydrous magnesium sulphate, filtered and evaporated. The residue was triturated with ether to give 417 mg of 5-(3,5-dichlorophenylthio)-4-isopropyl-3-ethyl ester-1-[(4-pyridyl)methyl]-1H-pyrrole-2-carboxylic acid as an orange foam. Mass spectrum (ESI) m/z 493 [M+H]$^+$.

(D) To a solution of 417 mg of 5-(3,5-dichlorophenylthio)-4-isopropyl-3-ethyl ester-1-[(4-pyridyl)methyl]-1H-pyrrole-2-carboxylic acid in 10 mL of dichloromethane was added 243 mg of EDAC, 171 mg of HOBt, 124 mg of N,N-dimethyl hydroxylamine then finally 0.33 mL of N-ethyl morpholine. The reaction mixture was stirred at room temperature for 1 h. The orange solution was quenched with saturated sodium bicarbonate solution and extracted with ethyl acetate. The combined organic extracts were dried over anhydrous magnesium sulphate, filtered and evaporated. The residue was purified by flash chromatography on silica gel using petrol/ethyl acetate (1:4 then 1:2) then ethyl acetate for the elution to give 233 mg of 5-(3,5-dichlorophenylthio)-4-isopropyl-3-ethyl ester-1-[(4-pyridyl)methyl]-2-[N-methyl-N-methoxyamide]-1H-pyrrole as a yellow oil. Mass spectrum (ESI) m/z 535 [M+H]$^+$.

Example 110

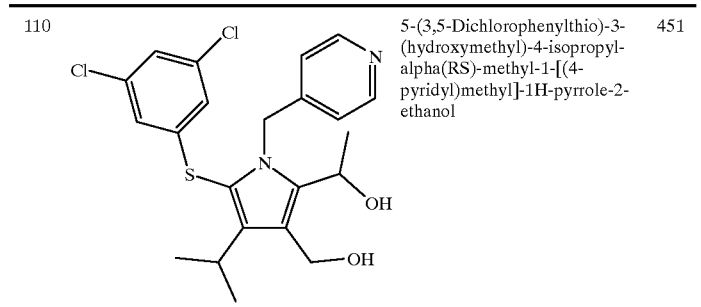

| 110 | | 5-(3,5-Dichlorophenylthio)-3-(hydroxymethyl)-4-isopropyl-alpha(RS)-methyl-1-[(4-pyridyl)methyl]-1H-pyrrole-2-ethanol | 451 |

To a solution of 60 mg of 5-(3,5-Dichlorophenylthio)-3-(hydroxymethyl)-4-isopropyl-1-[(4-pyridyl)methyl]-1H-pyrrole-2-carboxaldehyde in 1 mL of THF was added 0.1 mL of a 3M solution of methyl magnesium iodide in diethyl ether. The mixture was stirred at room temperature under nitrogen for 1 h. The reaction was quenched with saturated ammonium chloride solution and extracted with ethyl acetate. The combined organic extracts were washed with brine, dried over anhydrous magnesium sulphate, filtered and evaporated. The residue was purified by flash chromatography on silica gel using ethyl acetate for the elution to give 22 mg of a gum. Mass spectrum (ESI) m/z 451 [M+H]$^+$.

The starting material 5-(3,5-Dichlorophenylthio)-3-(hydroxymethyl)-4-isopropyl-1-[(4-pyridyl)methyl]-1H-pyrrole-2-carboxaldehyde was prepared as follows:

To a solution of 371 mg of 5-(3,5-dichlorophenylthio)-4-isopropyl-3-ethyl ester-1-[(4-pyridyl)methyl]-2-[N-methyl-N-methoxyamide]-1H-pyrrole in 10 mL of THF at 0° C. was added 1.4mL of a 1M solution of lithium aluminum hydride in ether. The mixture was stirred for 30 min then quenched with saturated ammonium chloride solution and extracted with ethyl acetate. The combined organic extracts were washed with brine, dried over anhydrous magnesium sulphate, filtered and evaporated. The residue was purified by flash chromatography on silica gel using ethyl acetate for the elution to give 223 mg of 5-(3,5-dichlorophenylthio)-4-isopropyl-1-[(4-pyridyl)methyl]-1H-pyrrole-3-methanol-2-carboxaldehyde as a gum. Mass spectrum (ESI) m/z 434 [M+H]$^+$.

Example 111

To a 1M solution of lithium aluminum hydride in ether at 0° C., under nitrogen, was added 70 mg of 5-(3,5-dichlorophenylthio)-4-isopropyl-1-[(4-pyridyl)methyl]-1H-pyrrole-2,3-bisethyl ester as a solution in 3mL of ether. The mixture was stirred for 1 h then quenched with saturated ammonium chloride solution and extracted with ethyl acetate. The combined organic extracts were washed with brine, dried over anhydrous magnesium sulphate, filtered and evaporated. The residue was purified by flash chromatography on silica gel using petrol/ethyl acetate (1:9 then 1:4) for the elution to give 16 mg of a gum. Mass spectrum (ESI) m/z 437 [M+H]$^+$.

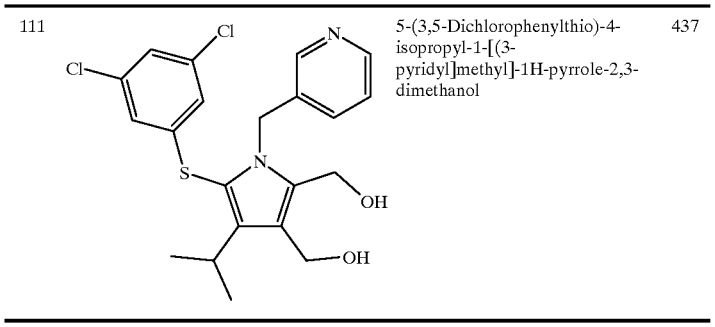

| 111 | | 5-(3,5-Dichlorophenylthio)-4-isopropyl-1-[(3-pyridyl)methyl]-1H-pyrrole-2,3-dimethanol | 437 |

Example 117

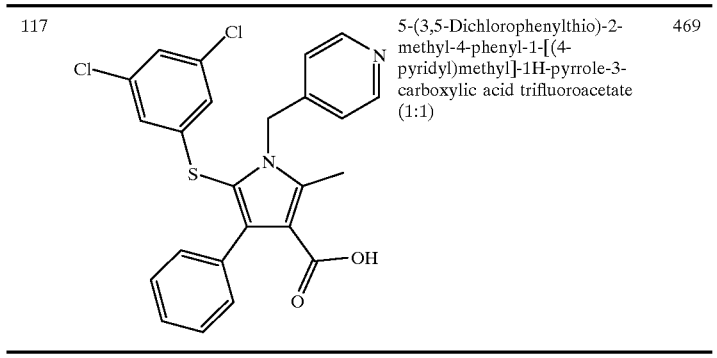

| 117 | | 5-(3,5-Dichlorophenylthio)-2-methyl-4-phenyl-1-[(4-pyridyl)methyl]-1H-pyrrole-3-carboxylic acid trifluoroacetate (1:1) | 469 |

To a solution of 243 mg of 5-(3,5-dichlorophenylthio)-4-phenyl-2-methyl-1-[(4-pyridyl)methyl]-1H-pyrrole-3-tertbutyl ester in 6 ml of dichloromethane was added 6 ml of trifluoroacetic acid at room temperature. The mixture was stirred for 1 h then evaporated and the residue was purified by flash chromatography on silica gel using petrol/ethyl acetate (1:4 then 1:1) for the elution to give 155 mg of a foam. Mass spectrum (ESI) m/z 469 [M+H]$^+$.

Example 115 room temperature for 18 h. The reaction was quenched with saturated sodium bicarbonate solution and extracted with ethyl acetate. The combined organic extracts were dried over anhydrous magnesium sulphate, filtered and evaporated. The residue was purified by flash chromatography on silica gel using petrol/ethyl acetate (1:4 then 1:2) then ethyl acetate for the elution to give 29 mg of 5-(3,5-dichlorophenylthio)-4-isopropyl-2-methyl-1-[(4-pyridyl)methyl]-1H-pyrrole as an oil, mass spectrum (ESI) m/z 391 [M+H]$^+$ and 114 mg of 5-(3,5-dichlorophenylthio)-4-

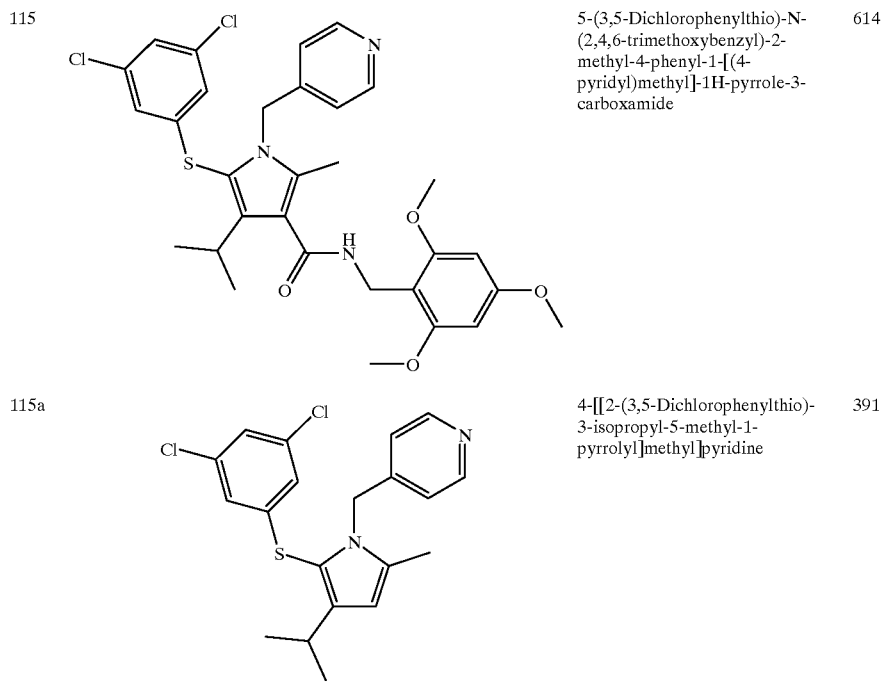

| 115 | | 5-(3,5-Dichlorophenylthio)-N-(2,4,6-trimethoxybenzyl)-2-methyl-4-phenyl-1-[(4-pyridyl)methyl]-1H-pyrrole-3-carboxamide | 614 |
| 115a | | 4-[[2-(3,5-Dichlorophenylthio)-3-isopropyl-5-methyl-1-pyrrolyl]methyl]pyridine | 391 |

To a solution of 160 mg of 5-(3,5-Dichlorophenylthio)-2-methyl-4-isopropyl-1-[(4-pyridyl)methyl]-1H-pyrrole-3-carboxylic acid in 10 ml of dichloromethane were added 60 mg of EDAC, 40 mg of HOBt, 68 mg of 2,4,6-trimethoxybenzylamine hydrochloride and 0.11 ml of N-ethyl morpholine. The reaction mixture was stirred at isopropyl-2-methyl-1-[(4-pyridyl)methyl]-1H-pyrrole-3-N-[(2,4,6-trimethoxy)benzyl]-carboxamide as an oil, mass spectrum (ESI) m/z 614 [M+H]$^+$.

Example 118

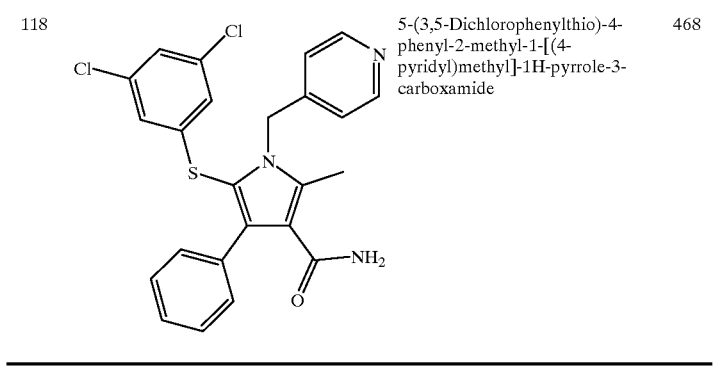

| 118 | | 5-(3,5-Dichlorophenylthio)-4-phenyl-2-methyl-1-[(4-pyridyl)methyl]-1H-pyrrole-3-carboxamide | 468 |

To a solution of 110 mg of 5-(3,5-Dichlorophenylthio)-N-(2,4,6-trimethoxybenzyl)-2-methyl-4-phenyl-1-[(4-pyridyl)methyl]-1H-pyrrole-3-carboxamide in 4 ml of dichloro-methane was added 3 ml of trifluoroacetic acid at room temperature. The mixture was stirred for 1 h then evaporated and the residue was purified by flash chromatography on silica gel using petrol/ethyl acetate (1:9 then 1:4) for the elution to give 26 mg of a white solid. Mass spectrum (ESI) m/z 468 [M+H]+.

Example 119

The mixture was refluxed for 1 h then cooled to room temperature. The reaction was quenched with saturated sodium bicarbonate solution and extracted with ethyl acetate. The combined organic extracts were dried over anhydrous magnesium sulphate, filtered and evaporated. The residue was purified by flash chromatography on silica gel using petrol/ethyl acetate (1:4 then 1:2) then ethyl acetate for the elution to give 13 mg of a gum. Mass spectrum (ESI) m/z 450 [M+H]+.

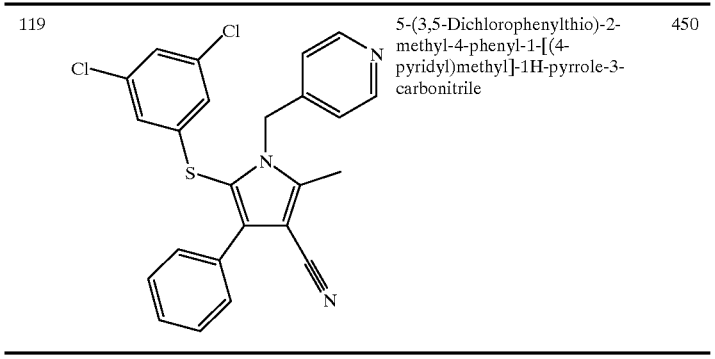

| 119 | | 5-(3,5-Dichlorophenylthio)-2-methyl-4-phenyl-1-[(4-pyridyl)methyl]-1H-pyrrole-3-carbonitrile | 450 |

Example 113

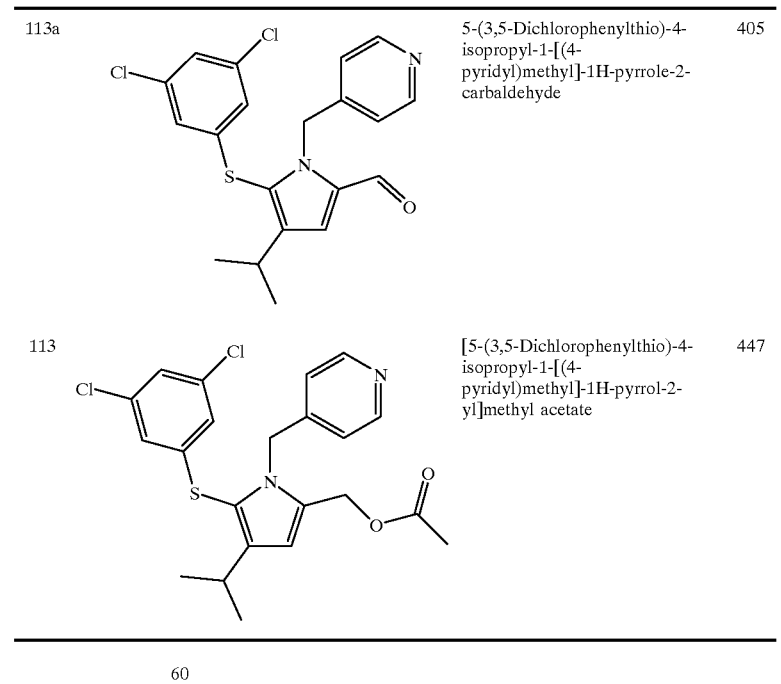

| 113a | | 5-(3,5-Dichlorophenylthio)-4-isopropyl-1-[(4-pyridyl)methyl]-1H-pyrrole-2-carbaldehyde | 405 |
| 113 | | [5-(3,5-Dichlorophenylthio)-4-isopropyl-1-[(4-pyridyl)methyl]-1H-pyrrol-2-yl]methyl acetate | 447 |

To a solution of 17 mg of 5-(3,5-Dichlorophenylthio)-4-phenyl-2-methyl-1-[(4-pyridyl)methyl]-1H-pyrrole-3-carboxamide in toluene was added 22 mg of Lawessons reagent.

To a solution of 160 mg of 5-(3,5-dichlorophenylthio)-4-isopropyl-2-methyl-1-[(4-pyridyl)methyl]-1H-pyrrole in 3 ml of acetic acid was added 200 mg of lead tetraacetate over 30 min. After stirring for 2 h at room temperature a further 100 mg of lead tetraacetate was added and the mixture stirred for 18 h. After this time a further 100 mg of lead tetraacetate was added and the mixture stirred for 18 h. The reaction was quenched with saturated sodium bicarbonate solution and extracted with ethyl acetate. The combined organic extracts were dried over anhydrous magnesium sulphate, filtered and evaporated. The residue was purified by flash chromatography on silica gel using petrol/ethyl acetate (1:4 then 1:2) then ethyl acetate for the elution to give 23 mg of 5-(3,5-dichlorophenylthio)-4-isopropyl-1-[(4-pyridyl)methyl]-1H-pyrrole-2-carbaldehyde, mass spectrum (ESI) m/z 405 [M+H]$^+$, as a brown oil and 51 mg of 5-(3,5-dichlorophenylthio)-4-isopropyl-1-[(4-pyridyl)methyl]-1H-pyrrole-2-acylmethanol as an impure yellow foaming oil, Mass spectrum (ESI) m/z 447 [M+H]$^+$.

To a solution of 51 mg of the impure 5-(3,5-dichlorophenylthio)-4-isopropyl-1-[(4-pyridyl)methyl]-1H-pyrrole-2-acylmethanol in 4 ml of 50% aqueous acetone was added 50 mg of powdered potassium hydroxide. The mixture was stirred at room temperature for 2 h. The reaction was quenched with water and extracted with diethyl ether. The combined organic extracts were dried over anhydrous magnesium sulphate, filtered and evaporated. The residue was purified by flash chromatography on silica gel using petrol/ethyl acetate (1:4 then 1:2) then ethyl acetate for the elution to give 8 mg of 5-(3,5-dichlorophenylthio)-4-isopropyl-1-[(4-pyridyl)methyl]-1H-pyrrole-2-methanol as a yellow gum, mass spectrum (ESI) m/z 407 [M+H]$^+$, and 9 mg of 5-(3,5-dichlorophenylthio)-4-isopropyl-1-[(4-pyridyl)methyl]-1H-pyrrole-2-[4'-but-3-en-2-one] as a yellow gum, mass spectrum (ESI) m/z 445 [M+H]$^+$.

Examples 112, 114

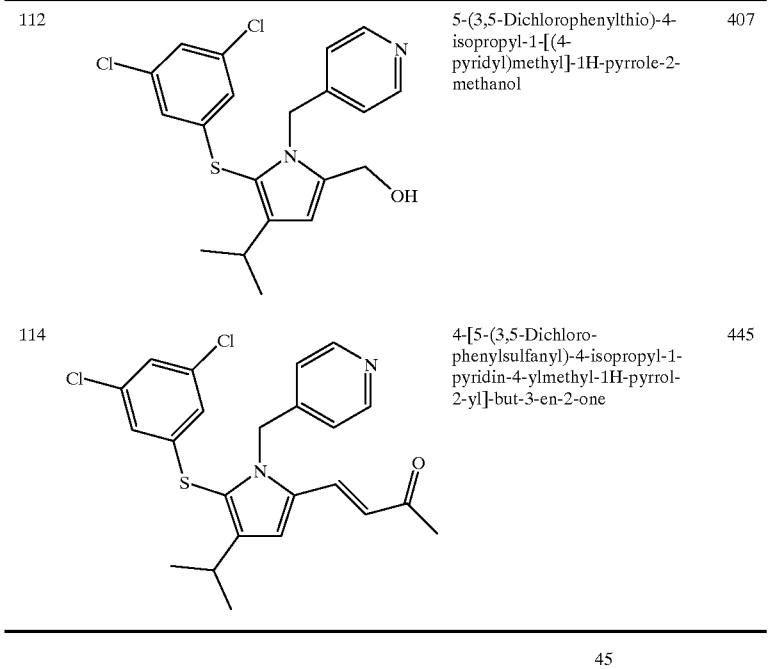

Example 130

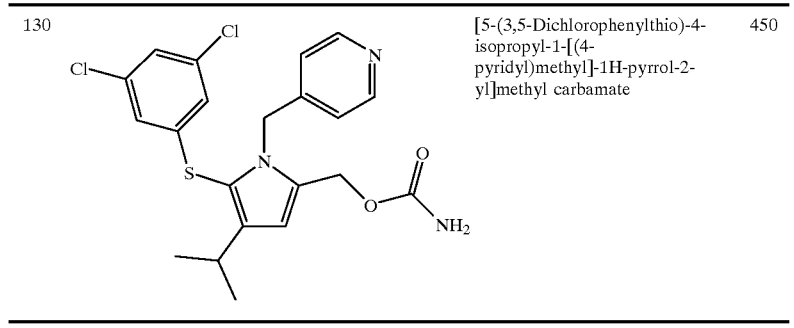

To a solution of 103 mg of 5-(3,5-Dichlorophenylthio)-4-isopropyl-1-[(4-pyridyl)methyl]-1H-pyrrole-2-methanol in 3 ml of dichloromethane was added 57 mg of trichloroacetyl isocyanate dropwise at 0° C. The mixture was stirred at 0° C. for 2 h then evaporated. To the residue was added 2 ml of methanol, 1 ml of water and 103 mg of potassium carbonate at 0° C. The mixture was warmed to room temperature and stirred for 2 h. After this time the solution was homogenous and orange in color. The reaction was quenched with water and extracted with ethyl acetate. The combined organic extracts were dried over anhydrous magnesium sulphate, filtered and evaporated. The residue was purified by flash chromatography on silica gel using petrol/ethyl acetate (1:4) for the elution to give 27 mg of a white solid. Mass spectrum (ESI) m/z 450 [M+H]$^+$.

Example 132

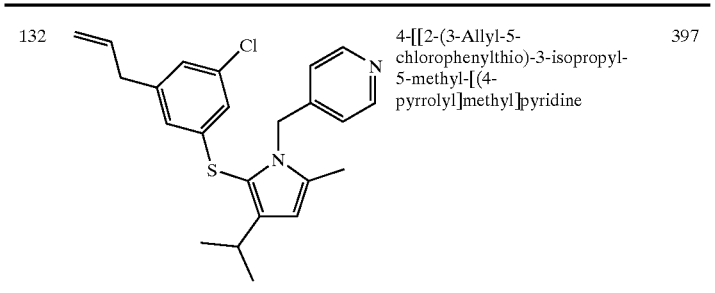

132     4-[[2-(3-Allyl-5-chlorophenylthio)-3-isopropyl-5-methyl-[(4-pyrrolyl]methyl]pyridine     397

To a solution of 80 mg of 4-[[2-(3-Bromo-5-chlorophenylthio)-3-isopropyl-5-methyl-1-pyrrolyl]methyl]pyridine in 5 ml of dimethoxyethane was added 156 µl of allyltributyltin and 60 mg of tetrakis(triphenylphosphine)palladium. The mixture was heated to 70° C. for 18 h. The mixture was directly purified by flash chromatography on silica gel using methanol/dichloromethane (1:19) for the elution to give 40 mg of a white solid. Mass spectrum (ESI) m/z 397 [M+H]$^+$.

Example 133

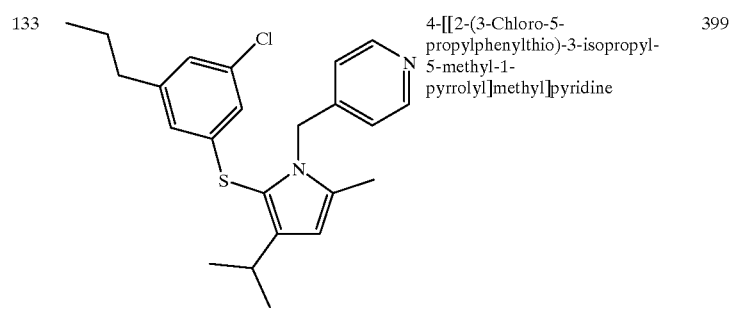

133     4-[[2-(3-Chloro-5-propylphenylthio)-3-isopropyl-5-methyl-1-pyrrolyl]methyl]pyridine     399

To a solution of 10 mg of 4-[[2-(3-Allyl-5-chlorophenylthio)-3-isopropyl-5-methyl-[(4-pyrrolyl]methyl]pyridine in 5 ml of warm ethanol was added 1 mg of 10% palladium on carbon. The mixture was hydrogenated for 10 min then filtered through a pad of celite. The filtrate was evaporated to dryness to give 10 mg of a white solid. Mass spectrum (ESI) m/z 399 [M+H]+.

Example 135

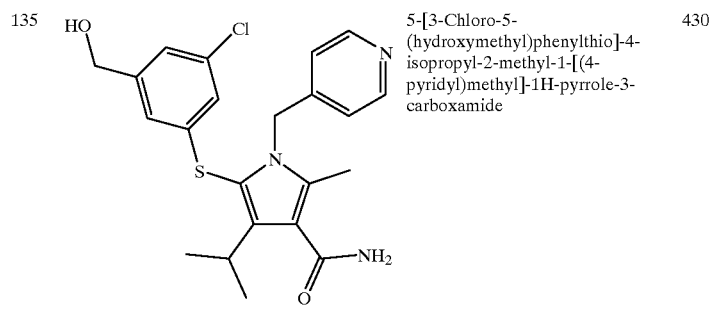

| 135 | 5-[3-Chloro-5-(hydroxymethyl)phenylthio]-4-isopropyl-2-methyl-1-[(4-pyridyl)methyl]-1H-pyrrole-3-carboxamide | 430 |

To a solution of 25 mg of 5-[3-Chloro -5-(carboxaldehyde)phenylthio]-4-isopropyl-2-methyl-1-[(4-pyridyl)methyl]-1H-pyrrole-3-carboxamide in 5 ml of methanol was added 3 mg of sodium borohydride. The mixture was stirred at room temperature for 2 h. A further 3 mg of sodium borohydride was then added and the mixture stirred for 1 h. To the reaction was added 150 mg of silica gel and the solvents evaporated. The product, absorbed onto silica, was purified by flash chromatography on silica gel using methanol/dichloromethane (1:9) for the elution to give 15 mg of a white solid. Mass spectrum (ESI) m/z 430 [M+H]+.

The starting material 5-[3-Chloro-5-(carboxaldehyde)phenylthio]-4-isopropyl-2-methyl-1-[(4-pyridyl)methyl]-1H-pyrrole-3-carboxamide was prepared as follows:

To a solution of 5-[3-Chloro-5-vinyl phenylthio]-4-isopropyl-2-methyl-1-[(4-pyridyl)methyl]-1H-pyrrole-3-carboxamide in 20 ml of THF, 10 ml of water and 6 ml of tertbutanol was added 290 mg of osmium tetroxide. The mixture was stirred at room temperature for 30 min and 330 mg of sodium periodate added. After 2 h 60 mg of the product was precipitated as a white solid by addition of ethyl acetate/water. Mass spectrum (ESI) m/z 425 [M+H]+.

Example 127

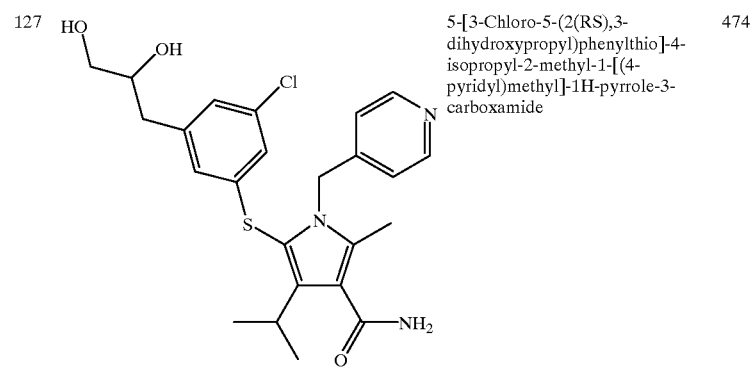

| 127 | 5-[3-Chloro-5-(2(RS),3-dihydroxypropyl)phenylthio]-4-isopropyl-2-methyl-1-[(4-pyridyl)methyl]-1H-pyrrole-3-carboxamide | 474 |

To a solution of 30 mg of 4-[[2-(3-Allyl-5-chlorophenylthio)-3-isopropyl-5-methyl-[(4-pyrrolyl]methyl]pyridinein 7.5 ml of THF, 4 ml of water and 1 ml of tert.-butanol was added 18 mg of osmium tetroxide. The mixture was stirred at room temperature for 30 min and 20 mg of sodium periodate added. After 2 h 15 mg of the product was precipitated as a white solid by addition of diethyl ether. Mass spectrum (ESI) m/z 474 [M+H]+.

Example 141

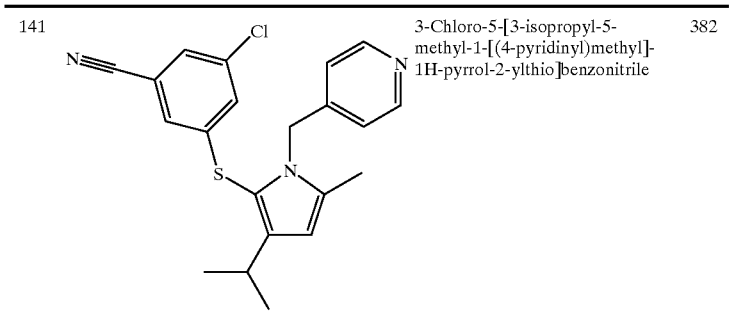

| | | | |
|---|---|---|---|
| 141 | (structure) | 3-Chloro-5-[3-isopropyl-5-methyl-1-[(4-pyridinyl)methyl]-1H-pyrrol-2-ylthio]benzonitrile | 382 |

A mixture of 120 mg of 4-[[2-(3-Bromo-5-chlorophenylthio)-3-isopropyl-5-methyl-1-pyrrolyl]methyl] pyridine, 96 mg of copper (I) cyanide, 30 mg of diphenylphosphino ferrocene, 40 mg of tetraethylammonium cyanide and 15 mg of bispalladium tris(dibenzylidene acetone) were dissolved on 15 ml of dioxane. The mixture was heated to 80° C. for 2 h then another 96 mg of copper (I) cyanide, 30 mg of diphenylphosphino ferrocene, 40 mg of tetraethyl-ammonium cyanide and 15 mg of bispalladium tris(dibenzylidene acetone) were added and the mixture heated for 72 h. The reaction was then cooled and The mixture was stirred at room temperature for 18 h. The orange solution was quenched with saturated sodium bicarbonate solution and extracted with ethyl acetate. The combined organic extracts were dried over anhydrous magnesium sulphate, filtered and evaporated. The residue was purified by flash chromatography on silica gel using petrol/ethyl acetate (1:4 then 1:2) then ethyl acetate for the elution to give 57 mg as an oil which was further purified by HPLC to give 17 mg of an oil. Mass spectrum (ESI) m/z 382 [M+H]$^+$.

Examples 36–74

In a manner analogous to the process described in reaction scheme 1, the following compounds were prepared:

| Ex. | STRUCTURE | SYSTEMATIC NAME | Mass Spectrum (m/z ES, +ve ion) | Reaction Scheme |
|---|---|---|---|---|
| 36 | (structure) | 5-(3,5-Dichlorophenylthio)-2,4-dimethyl-1-[(4-pyridyl)methyl]-1H-pyrrole-3-methanol | 393 | 1 using MeCOCH2NH2 |
| 37 | (structure) | 5-(3,5-Dichlorophenylthio)-4-isopropyl-2-phenyl-1-[(4-pyridyl)methyl]-1H-pyrrole-3-methanol | 483 | 1 using PhCOCH2CO2Et |

-continued

| Ex. | STRUCTURE | SYSTEMATIC NAME | Mass Spectrum (m/z ES, +ve ion) | Reaction Scheme |
|---|---|---|---|---|
| 38 | 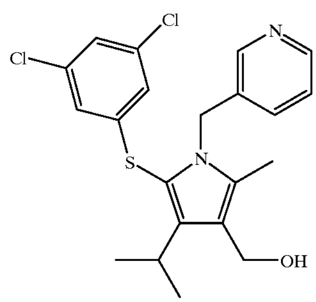 | 5-(3,5-Dichlorophenylthio)-4-isopropyl-2-methyl-1-[(3-pyridyl)methyl]-1H-pyrrole-3-methanol | 421 | 1 different R1 |
| 39 | 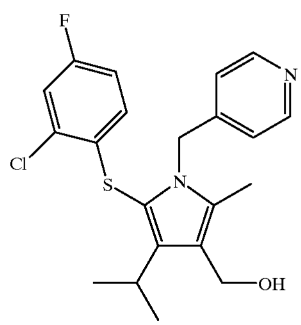 | 5-(2-chloro-4-fluorophenylthio)-4-isopropyl-2-methyl-1-[(4-pyridyl)methyl]-1H-pyrrole-3-methanol | 404 | 1 different disulfide |
| 40 | 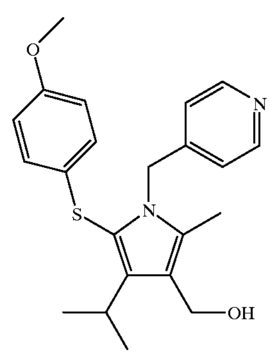 | 4-Isopropyl-5-(4-methoxyphenylthio)-2-methyl-1-[(4-pyridyl)methyl]-1H-pyrrole-3-methanol | 382 | 1 different disulfide |
| 41 | 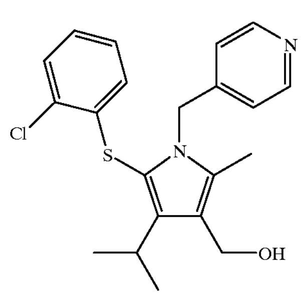 | 5-(2-Chlorophenylthio)-4-isopropyl-2-methyl-1-[(4-pyridyl)methyl]-1H-pyrrole-3-methanol | 387 | 1 different disulfide |

| Ex. | STRUCTURE | SYSTEMATIC NAME | Mass Spectrum (m/z ES, +ve ion) | Reaction Scheme |
|---|---|---|---|---|
| 42 | 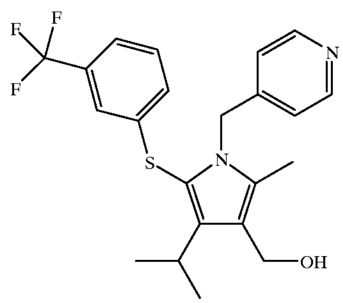 | 5-[3-(Trifluoromethyl) phenylthio]-4-isopropyl-2-methyl-1-[(4-pyridyl)methyl]-1H-pyrrole-3-methanol | 420 | 1 different disulfide |
| 43 | 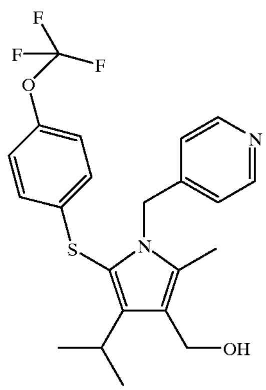 | 5-[4-(Trifluoromethoxy) phenylthio]-4-isopropyl-2-methyl-1-[(4-pyridyl)methyl]-1H-pyrrole-3-methanol | 436 | 1 different disulfide |
| 44 | 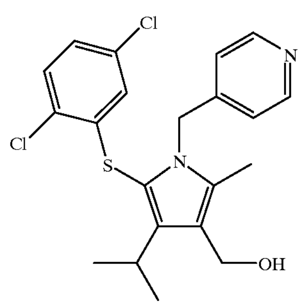 | 5-(2,5-Dichlorophenylthio)-4-isopropyl-2-methyl-1-[(4-pyridyl)methyl]-1H-pyrrole-3-methanol | 421 | 1 different disulfide |
| 45 | 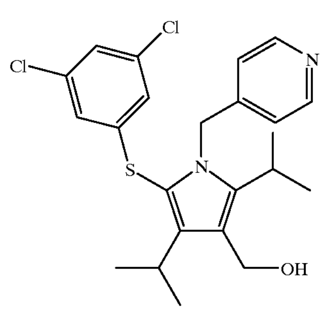 | 5-(3,5-Dichlorophenylthio)-2,4-diisopropyl-1-[(4-pyridyl)methyl]-1H-pyrrole-3-methanol | 449 | 1 using iPrCOCH2CO2Et |

-continued

| Ex. | STRUCTURE | SYSTEMATIC NAME | Mass Spectrum (m/z ES, +ve ion) | Reaction Scheme |
|---|---|---|---|---|
| 46 | 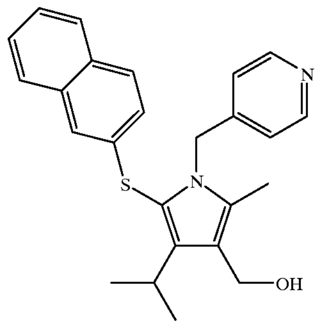 | 4-Isopropyl-2-methyl-5-(2-naphthylthio)-1[(4-pyridinyl)methyl]-1H-pyrrole-3-methanol | 402 | 1 different disulfide |
| 47 | 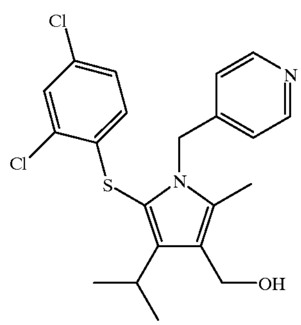 | 5-(2,4-Dichlorophenylthio)-4-isopropyl-2-methyl-1-[(4-pyridyl)methyl]-1H-pyrrole-3-methanol | 421 | 1 different disulfide |
| 48 | 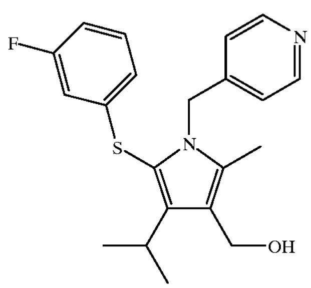 | 5-(3-Fluorophenylthio)-4-isopropyl-2-methyl-1-[(4-pyridyl)methyl]-1H-pyrrole-3-methanol | 370 | 1 different disulfide |
| 49 | 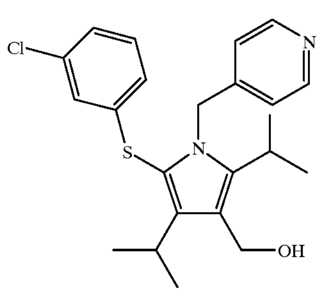 | 5-(3-Chlorophenylthio)-2,4-diisopropyl-1-[(4-pyridyl)methyl]-1H-pyrrole-3-methanol | 415 | 1 using iPr2COCH2CO2Et |

-continued

| Ex. | STRUCTURE | SYSTEMATIC NAME | Mass Spectrum (m/z ES, +ve ion) | Reaction Scheme |
|---|---|---|---|---|
| 50 | 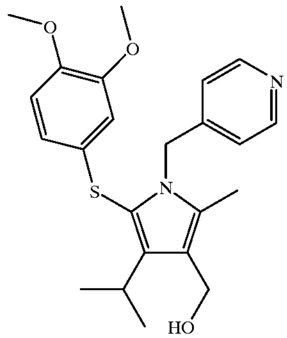 | 4-Isopropyl-5-(3,4-dimethoxyphenylthio)-2-methyl-1-[(4-pyridyl)methyl]-1H-pyrrole-3-methanol | 412 | 1 different disulfide |
| 51 | 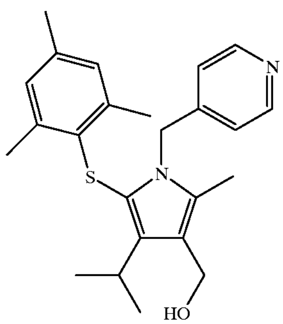 | 4-Isopropyl-2-methyl-5-(2,4,6-trimethylphenylthio)-1-[(4-pyridyl)methyl]-1H-pyrrole-3-methanol | 394 | 1 different disulfide |
| 52 | 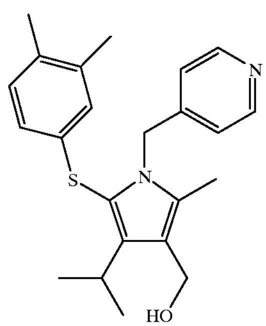 | 4-Isopropyl-2-methyl-5-(3,4-dimethylphenylthio)-1-[(4-pyridyl)methyl]-1H-pyrrole-3-methanol | 380 | 1 different disulfide |
| 53 | 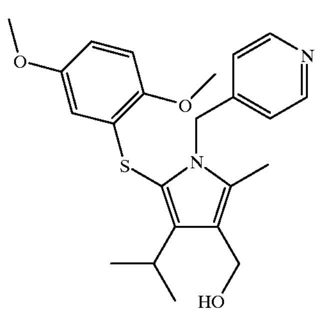 | 4-Isopropyl-5-(2,5-dimethoxyphenylthio)-2-methyl-1-[(4-pyridyl)methyl]-1H-pyrrole-3-methanol | 412 | 1 different disulfide |

| Ex. | STRUCTURE | SYSTEMATIC NAME | Mass Spectrum (m/z ES, +ve ion) | Reaction Scheme |
|---|---|---|---|---|
| 54 | 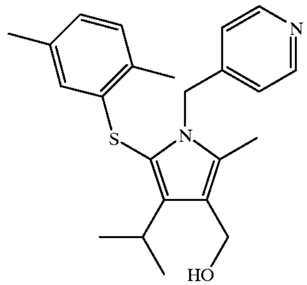 | 4-Isopropyl-2-methyl-5-(2,5-dimethylphenylthio)-1-[(4-pyridyl)methyl]-1H-pyrrole-3-methanol | 380 | 1 different disulfide |
| 55 | 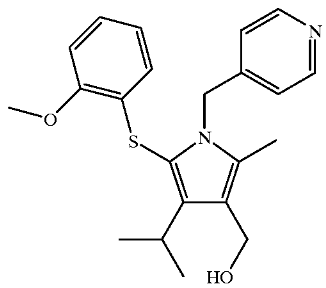 | 4-Isopropyl-5-(2-methoxyphenylthio)-2-methyl-1-[(4-pyridyl)methyl]-1H-pyrrole-3-methanol | 382 | 1 different disulfide |
| 56 | 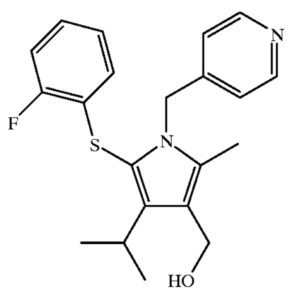 | 5-(2-Fluorophenylthio)-4-isopropyl-2-methyl-1-[(4-pyridyl)methyl]-1H-pyrrole-3-methanol | 370 | 1 different disulfide |
| 57 | 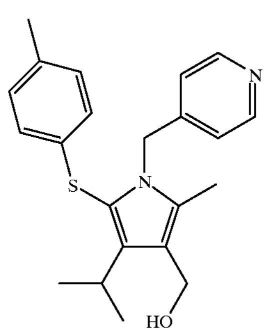 | 4-Isopropyl-2-methyl-5-(4-methylphenylthio)-1-[(4-pyridyl)methyl]-1H-pyrrole-3-methanol | 366 | 1 different disulfide |

-continued

| Ex. | STRUCTURE | SYSTEMATIC NAME | Mass Spectrum (m/z ES, +ve ion) | Reaction Scheme |
|---|---|---|---|---|
| 58 | 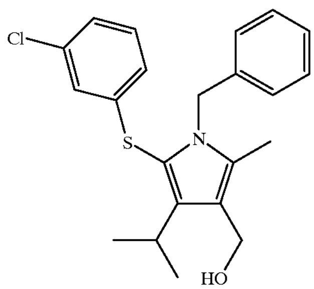 | 1-Benzyl-5-(3-chlorophenylthio)-4-isopropyl-2-methyl-1H-pyrrole-3-methanol | 386 | 1 different disulfide |
| 59 | 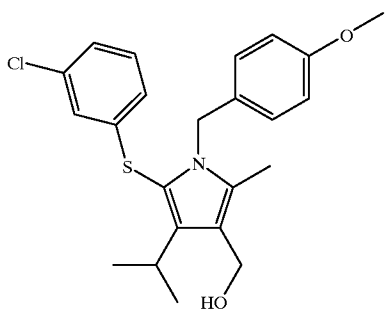 | 5-(3-Chlorophenylthio)-4-isopropyl-1-(4-methoxybenzyl)-2-methyl-1H-pyrrole-3-methanol | 416 | 1 different disulfide and R1 |
| 60 | 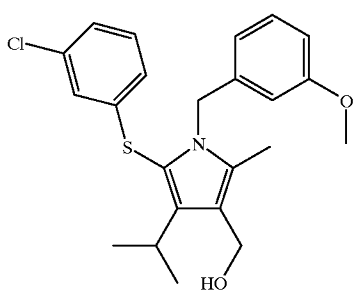 | 5-(3-Chlorophenylthio)-4-isopropyl-1-(3-methoxybenzyl)-2-methyl-1H-pyrrole-3-methanol | 416 | 1 different disulfide and R1 |
| 61 | 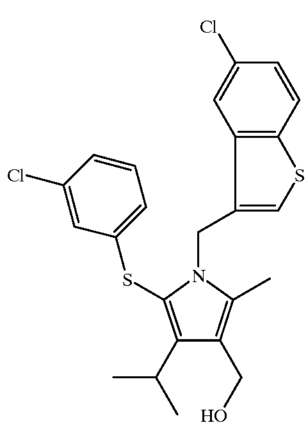 | 1-[(5-Chloro-1-benzothiophen-3-yl)methyl]-5-(3-chlorophenylthio)-4-isopropyl-2-methyl-1H-pyrrole-3-methanol | 476 | 1 different disulfide |

-continued

| Ex. | STRUCTURE | SYSTEMATIC NAME | Mass Spectrum (m/z ES, +ve ion) | Reaction Scheme |
|---|---|---|---|---|
| 62 | 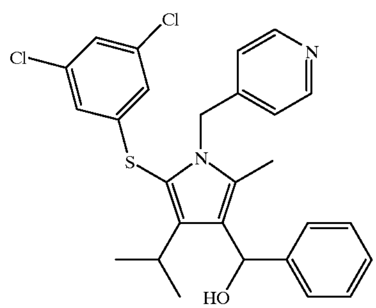 | alpha(RS)-[5-(3,5-Dichlorophenylthio)-4-isopropyl-2-methyl-1-[(4-pyridyl)methyl]-1H-pyrrol-3-yl]benzyl alcohol | 497 | 1 using PhMgBr |
| 63 | 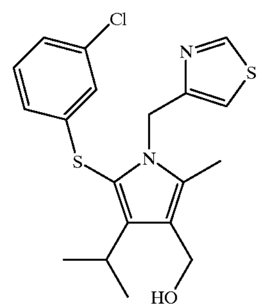 | 5-(3-Chlorophenylthio)-4-isopropyl-2-methyl-1-[(4-thiazolyl)methyl]-1H-pyrrole-3-methanol | 393 | 1 different disulfide and R1 |
| 64 | 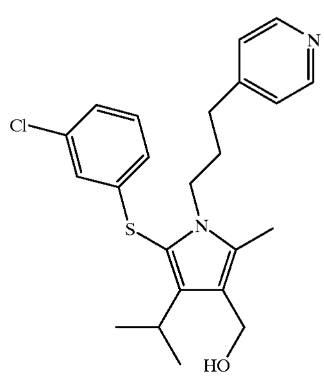 | 5-(3-Chlorophenylthio)-4-isopropyl-2-methyl-1-[3-(4-pyridyl)propyl]-1H-pyrrole-3-methanol | 415 | 1 different disulfide and R1 |
| 65 | 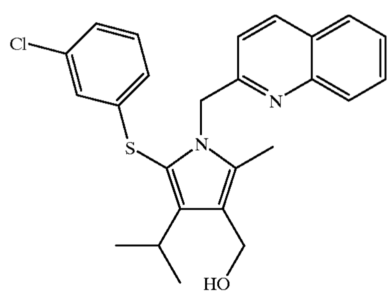 | 5-(3-Chlorophenylthio)-4-isopropyl-2-methyl-1-[(2-quinolyl)methyl]-1H-pyrrole-3-methanol | 437 | 1 different disulfide and R1 |

| Ex. | STRUCTURE | SYSTEMATIC NAME | Mass Spectrum (m/z ES, +ve ion) | Reaction Scheme |
|---|---|---|---|---|
| 66 | 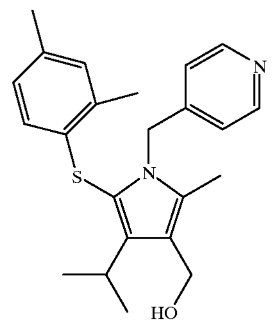 | 4-Isopropyl-2-methyl-5-(2,4-dimethylphenylthio)-1-[(4-pyridyl)methyl]-1H-pyrrole-3-methanol | 380 | 1 different disulfide |
| 67 | 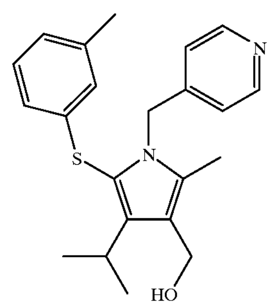 | 4-Isopropyl-2-methyl-5-(3-methylphenylthio)-1-[(4-pyridyl)methyl]-1H-pyrrole-3-methanol | 366 | 1 different disulfide |
| 68 | 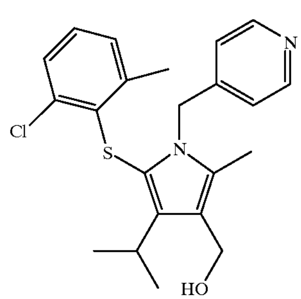 | 5-(2-Chloro-6-methylphenylthio)-4-isopropyl-2-methyl-1-[(4-pyridyl)methyl]-1H-pyrrole-3-methanol | 401 | 1 different disulfide |
| 69 | 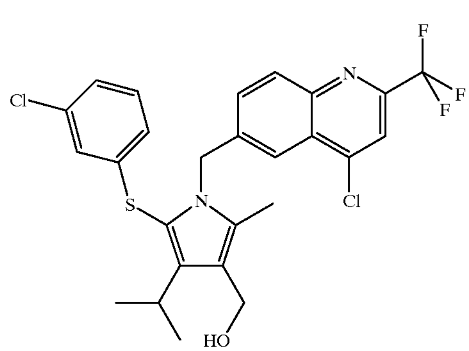 | 5-(3-Chlorophenylthio)-1-[[4-chloro-2-(trifluoromethyl)-6-quinolyl]methyl]-4-isopropyl-2-methyl-1H-pyrrole-3-methanol | 539 | 1 different disulfide and R1 |

-continued

| Ex. | STRUCTURE | SYSTEMATIC NAME | Mass Spectrum (m/z ES, +ve ion) | Reaction Scheme |
|---|---|---|---|---|
| 70 | 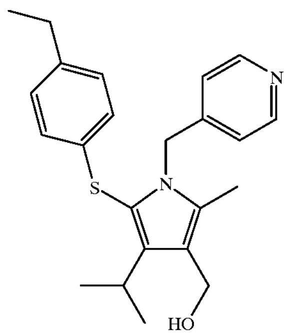 | 5-(4-Ethylphenylthio)-4-isopropyl-2-methyl-1-[(4-pyridyl)methyl]-1H-pyrrole-3-methanol | 380 | 1 different disulfide |
| 71 | 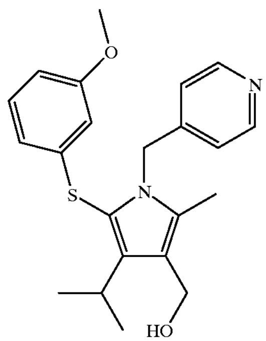 | 4-Isopropyl-5-(3-methoxyphenylthio)-2-methyl-1-[(4-pyridyl)methyl]-1H-pyrrole-3-methanol | 382 | 1 different disulfide |
| 72 | 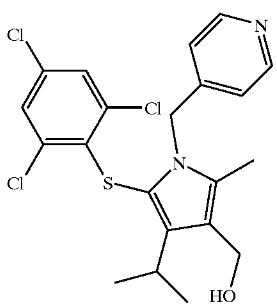 | 5-(2,4,6-Trichlorophenylthio)-4-isopropyl-2-methyl-1-[(4-pyridyl)methyl]-1H-pyrrole-3-methanol | 496 [M + MeCN + H]+ | 1 different sulfide |
| 73 | 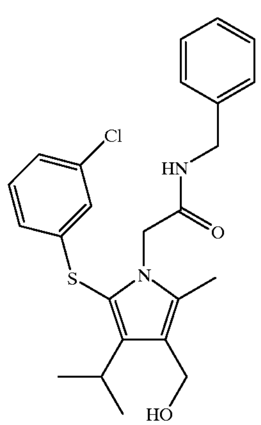 | N-Benzyl-2-(3-chlorophenylthio)-4-(hydroxymethyl)-3-isopropyl-5-methyl-1-pyrroleacetamide | 443 | 1 different disulfide and R1 |

-continued

| Ex. | STRUCTURE | SYSTEMATIC NAME | Mass Spectrum (m/z ES, +ve ion) | Reaction Scheme |
|---|---|---|---|---|
| 74 | 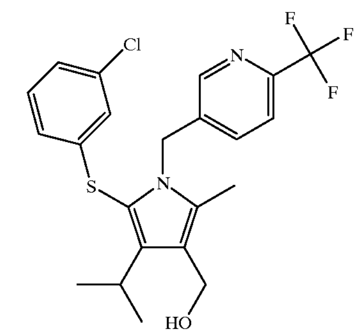 | 5-(3-Chlorophenylthio)-1-[[6-(trifluoromethyl)-3-pyridyl]methyl]-4-isopropyl-2-methyl-1H-pyrrole-3-methanol | 455 | 1 different disulfide and R1 |

Examples 75–79

In a manner analogous to the process described in Reaction Scheme 2, the following compounds were prepared:

| Ex. | STRUCTURE | SYSTEMATIC NAME | Mass Spectrum (m/z ES, +ve ion) | Reaction Scheme |
|---|---|---|---|---|
| 75 | 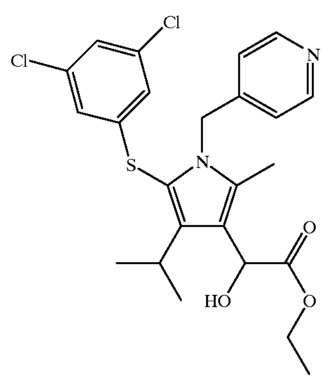 | [5-(3,5-Dichloro-phenylsulfanyl)-4-isopropyl-2-methyl-1-pyridin-4-ylmethyl-1H-pyrrol-3-yl]-hydroxy-acetic acid ethyl ester | 493 | 2 (reduction of ketone) |
| 76 | 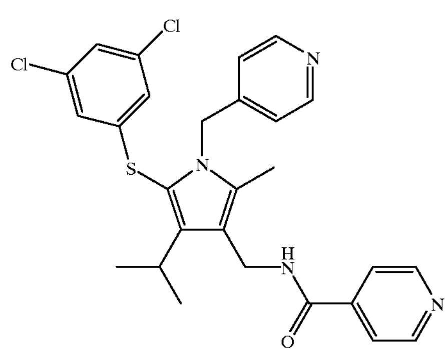 | N-[[5-(3,5-Dichlorophenylthio)-4-isopropyl-2-methyl-1-[(4-pyridyl)methyl]-1H-pyrrol-3-yl]methyl]-4-pyridineacetamide | 525 | 2 |

| Ex. | STRUCTURE | SYSTEMATIC NAME | Mass Spectrum (m/z ES, +ve ion) | Reaction Scheme |
|---|---|---|---|---|
| 77 | 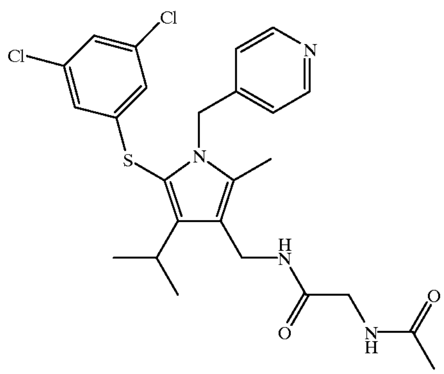 | 2-Acetamido-N-[[5-(3,5-dichlorophenylthio)-4-isopropyl-2-methyl-1-[(4-pyridyl)methyl]-1H-pyrrol-3-yl]methyl]acetamide | 519 | 2 |
| 78 | 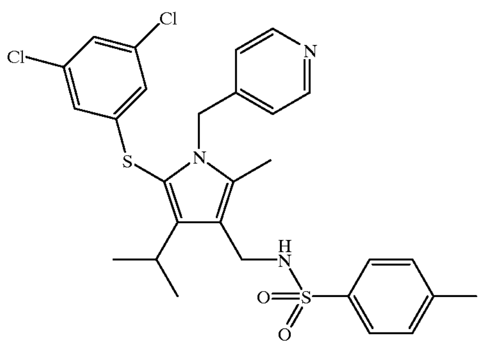 | N-[[5-(3,5-Dichlorophenylthio)-4-isopropyl-2-methyl-1-[(4-pyridyl)methyl]-1H-pyrrol-3-yl]methyl]-p-toluenesulfonamide | 574 | 2 |
| 79 | 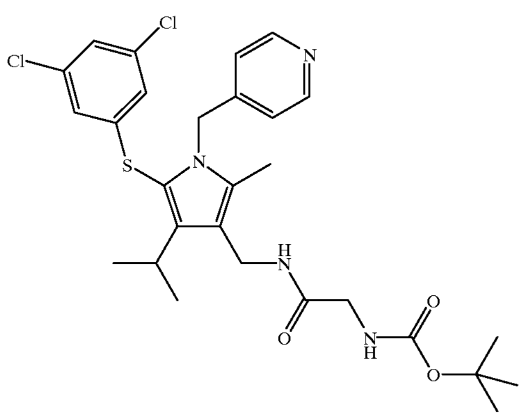 | tert.-butyl [[[[5-(3,5-dichlorophenylthio)-4-isopropyl-2-methyl-1-[(4-pyridyl)methyl]-1H-pyrrol-3-yl]methyl]carbamoyl]methyl]carbamate | 577 | 2 |
| 80 | 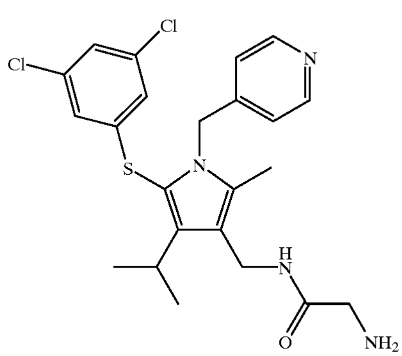 | N2-[[5-(3,5-Dichlorophenylthio)-4-isopropyl-2-methyl-1-[(4-pyridyl)methyl]-1H-pyrrol-3-yl]methyl]glycinamide | 477 | 2 |

-continued

| Ex. | STRUCTURE | SYSTEMATIC NAME | Mass Spectrum (m/z ES, +ve ion) | Reaction Scheme |
|---|---|---|---|---|
| 81 | 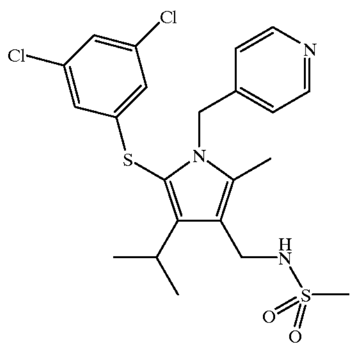 | N-[[5-(3,5-Dichlorophenylthio)-4-isopropyl-2-methyl-1-[(4-pyridyl)methyl-1H-pyrrol-3-yl]methyl]methanesulfonamide | 498 | 2 |
| 82 | 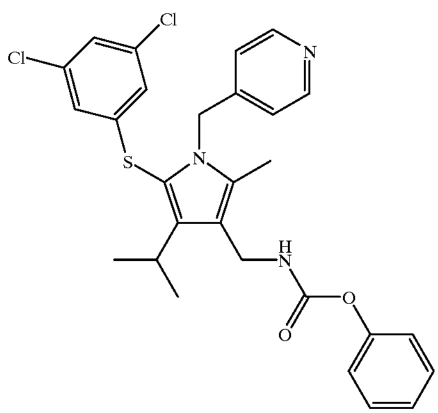 | Phenyl [[5-(3,5-dichlorophenylthio)-4-isopropyl-2-methyl-1-[(4-pyridyl)methyl]-1H-pyrrol-3-yl]methyl]carbamate | 540 | 2 |
| 83 | 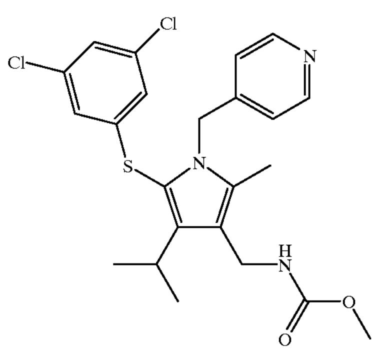 | Methyl [[5-(3,5-dichlorophenylthio)-4-isopropyl-2-methyl-1-[(4-pyridyl)methyl]-1H-pyrrol-3-yl]methyl]carbamate | 478 | 2 |
| 84 | 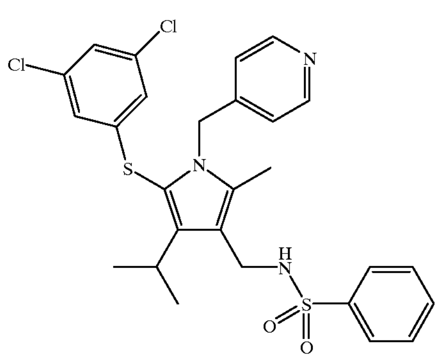 | N-[[5-(3,5-Dichlorophenylthio)-4-isopropyl-2-methyl-1-[(4-pyridyl)methyl]-1H-pyrrol-3-yl]methyl]benzenesulfonamide | 560 | 2 |

-continued

| Ex. | STRUCTURE | SYSTEMATIC NAME | Mass Spectrum (m/z ES, +ve ion) | Reaction Scheme |
|---|---|---|---|---|
| 85 | 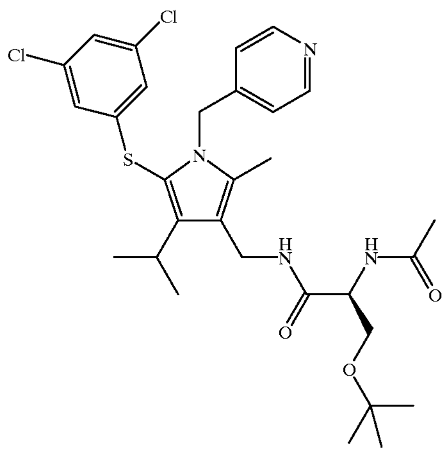 | N1-Acetyl-O-tert.-butyl-N2-[[5-(3,5-dichlorophenylthio)-4-isopropyl-2-methyl-1-[(4-pyridyl)methyl]-1H-pyrrol-3-ylmethyl]-L-serinamide | 605 | 2 |
| 86 | 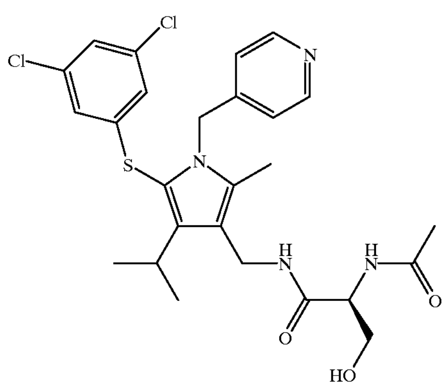 | N1-Acetyl-N2-[[5-(3,5-dichlorophenylthio)-4-isopropyl-2-methyl-1-[(4-pyridyl)methyl]-1H-pyrrol-3-yl]methyl]-L-serinamide | 549 | 2 |
| 87 | 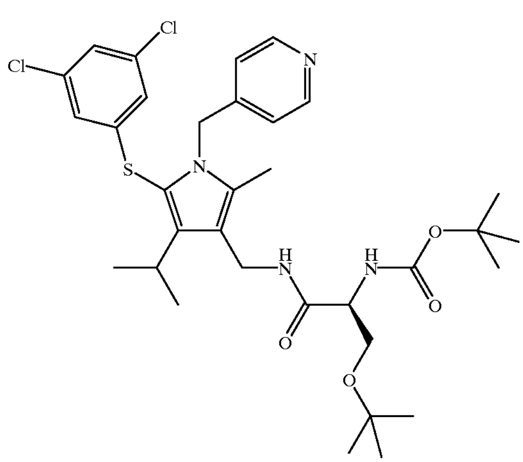 | N1-(tert.-butoxycarbonyl)-O-tert.-butyl-N2-[[5-(3,5-dichlorophenylthio)-4-isopropyl-2-methyl-1-[(4-pyridyl)methyl]-1H-pyrrol-3-yl]methyl]-L-serinamide | 663 | 2 |

-continued

| Ex. | STRUCTURE | SYSTEMATIC NAME | Mass Spectrum (m/z ES, +ve ion) | Reaction Scheme |
|---|---|---|---|---|
| 88 | 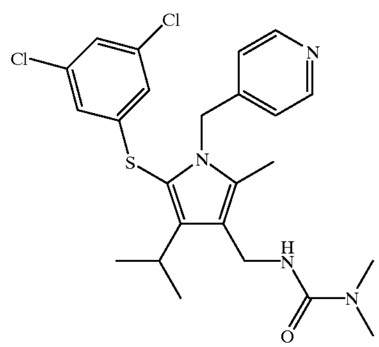 | 1-[[5-(3,5-Dichlorophenylthio)-4-isopropyl-2-methyl-1-[(4-pyridyl)methyl]-1H-pyrrol-3-yl]methyl]-3,3-dimethylurea | 491 | 2 |
| 89 | 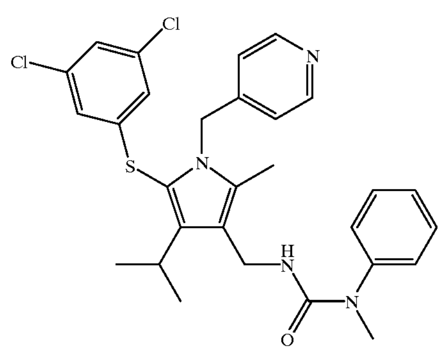 | 1-[[5-(3,5-Dichlorophenylthio)-4-isopropyl-2-methyl-1-[(4-pyriyl)methyl]-1H-pyrrol-3-yl]methyl]-3-methyl-3-phenylurea | 553 | 2 |
| 90 | 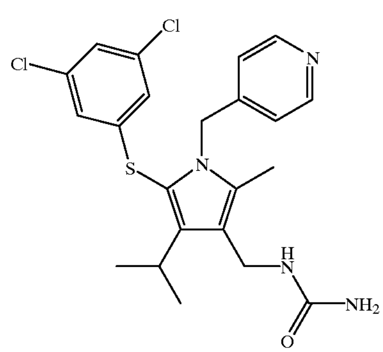 | 1-[[5-(3,5-Dichlorophenylthio)-4-isopropyl-2-methyl-1-[(4-pyridyl)methyl]-1H-pyrrol-3-yl]methyl]urea | 463 | 2 |
| 91 | 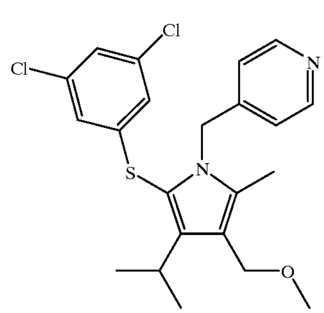 | 4-[[2-(3,5-Dichlorophenylthio)-3-isopropyl-4-(methoxymethyl)-5-methyl-1-pyrrolyl]methyl]pyridine | 435 | 2 |

-continued

| Ex. | STRUCTURE | SYSTEMATIC NAME | Mass Spectrum (m/z ES, +ve ion) | Reaction Scheme |
|---|---|---|---|---|
| 92 | 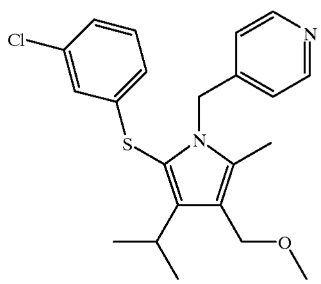 | 4-[[2-(3-Chlorophenylthio)-3-isopropyl-4-(methoxymethyl)-5-methyl-1-pyrrolyl]methyl]pyridine | 401 | 2 |
| 93 | 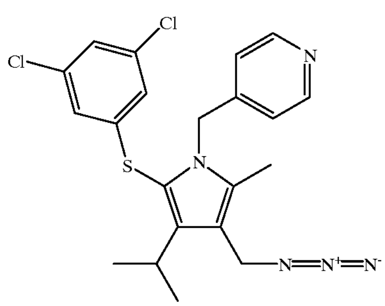 | 4-[[3-(Azidomethyl)-5-(3,5-dichlorophenylthio)-4-isopropyl-2-methyl-1-pyrrolyl]methyl]pyridine | 446 | 2 |
| 94 | 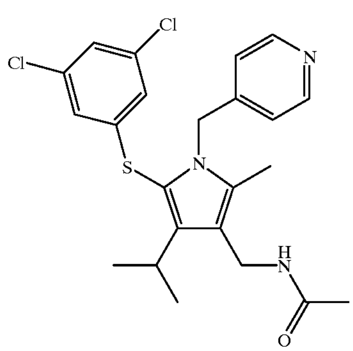 | N-[[5-(3,5-Dichlorophenylthio)-4-isopropyl-2-methyl-1-[(4-pyridyl)methyl]-1H-pyrrol-3-yl]methyl]acetamide | 462 | 2 |
| 95 | 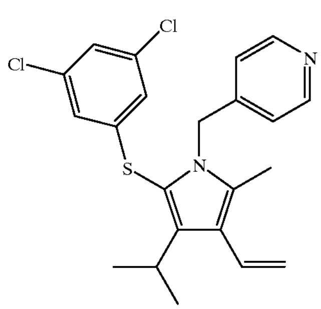 | 4-[[2-(3,5-Dichlorophenylthio)-3-isopropyl-5-methyl-4-vinyl-1-pyrrolyl]methyl]pyridine | 417 | 2 |

-continued

| Ex. | STRUCTURE | SYSTEMATIC NAME | Mass Spectrum (m/z ES, +ve ion) | Reaction Scheme |
|---|---|---|---|---|
| 96 | 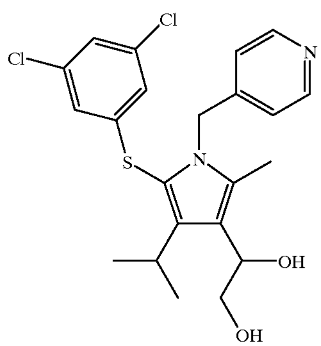 | 1(RS)-[5-(3,5-Dichlorophenylthio)-4-isopropyl-2-methyl-1-[(4-pyridyl)methyl]-1H-pyrrol-3-yl]-1,2-ethanediol | 451 | 2 from vinyl |
| 97 | 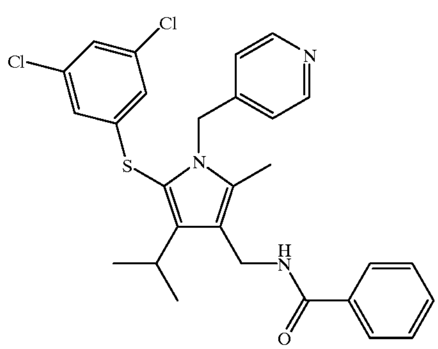 | N-[[5-(3,5-Dichlorophenylthio)-4-isopropyl-2-methyl-1-[(4-pyridyl)methyl]-1H-pyrrol-3-yl]methyl]benzamide | 524 | 2 |
| 98 | 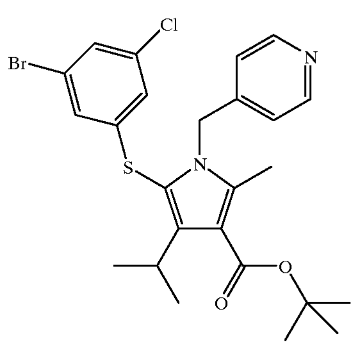 | tert.-butyl 5-(3-bromo-5-chlorophenylthio)-4-isopropyl-2-methyl-1-[(4-pyridyl)methyl]-1H-pyrrole-3-carboxylate | 536 | 2 tBu only difference |
| 99 | 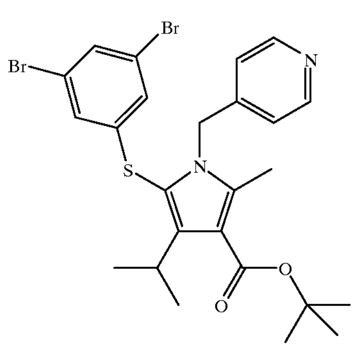 | tert.-butyl 5-(3,5-dibromophenylthio)-4-isopropyl-2-methyl-1-[(4-pyridyl)methyl]-1H-pyrrole-3-carboxylate | 580 | 2 tBu only difference |

Examples 100–106

In a manner analogous to the process described in Reaction Scheme 3, the following compounds were prepared:

| Ex. | STRUCTURE | SYSTEMATIC NAME | Mass Spectrum (m/z ES, +ve ion) | Reaction Scheme |
|---|---|---|---|---|
| 100 | 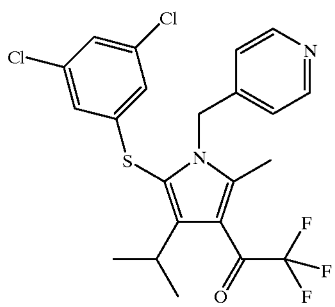 | 1-[5-(3,5-Dichlorophenylthio)-4-isopropyl-2-methyl-1-[(4-pyridyl)methyl]-1H-pyrrol-3-yl]-2,2,2-trifluoroethanone | 487 | 3 using CF3COCH2CO2Et |
| 101 | 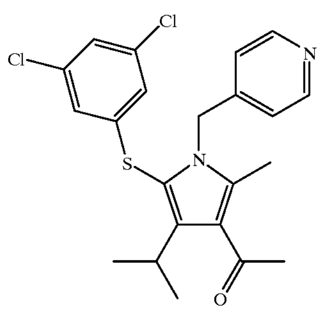 | 1-[5-(3,5-Dichlorophenylthio)-4-isopropyl-2-methyl-1-[(4-pyridyl)methyl]-1H-pyrrol-3-yl]ethanone | 433 | 3 using CH2COCH2COCH3 |
| 102 | 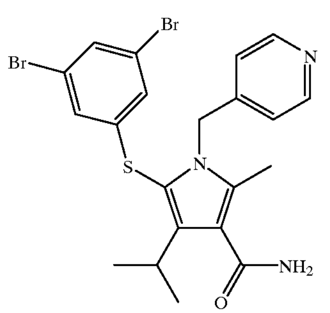 | 5-(3,5-Dibromophenylthio)-4-isopropyl-2-methyl-1-[(4-pyridyl)methyl]-1H-pyrrole-3-carboxamide | 523 | 3 using different disulfide and NH2COCH2CO2Et |
| 103 | 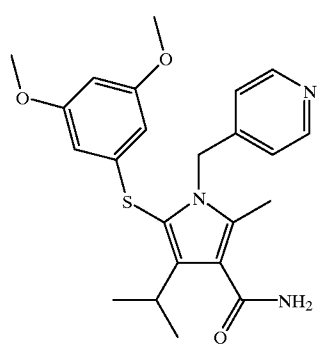 | 4-Isopropyl-5-(3,5-dimethoxyphenylthio)-2-methyl-1-[(4-pyridyl)methyl]-1H-pyrrole-3-carboxamide | 425 | 3 using different disulfide and NH2COCH2CO2Et |

-continued

| Ex. | STRUCTURE | SYSTEMATIC NAME | Mass Spectrum (m/z ES, +ve ion) | Reaction Scheme |
|---|---|---|---|---|
| 104 | 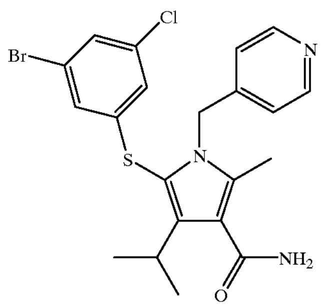 | 5-(3-Bromo-5-chlorophenylthio)-4-isopropyl-2-methyl-1-[(4-pyridyl)methyl]-1H-pyrrole-3-carboxamide | 480 | 3 using different disulfide and NH2COCH2CO2Et |
| 105 | 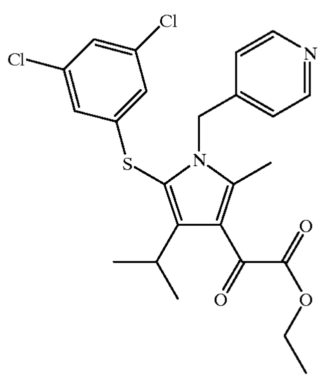 | Ethyl 5-(3,5-dichlorophenylthio)-4-isopropyl-2-methyl-1-[(4-pyridyl)methyl]-1H-pyrrole-3-glyoxalate | 491 | 3 using EtO2CCOCH2CO2Et |
| 106 | 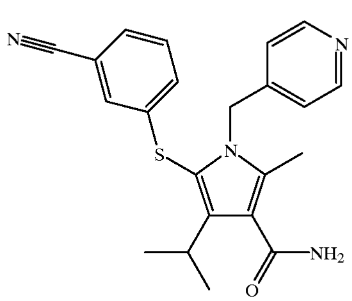 | 5-(3-Cyanophenylthio)-4-isopropyl-2-methyl-1-[(4-pyridyl)methyl]-1H-pyrrole-3-carboxamide | 390 | 3 using different disulfide and NH2COCH2CO2Et |

Examples 107–111

In a manner analogous to the process described in Reaction Scheme 6 or 7, the following compounds were prepared:

| Ex. | STRUCTURE | SYSTEMATIC NAME | Mass Spectrum (m/z ES, +ve ion) | Reaction Scheme |
|---|---|---|---|---|
| 107 | 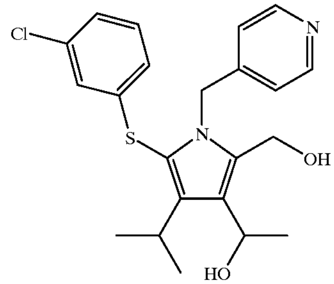 | 5-(3-Chlorophenylthio)-2-(hydroxymethyl)-4-isopropyl-alpha(RS)-methyl-1-[(4-pyridyl)methyl]-1H-pyrrole-3-ethanol | 417 | 6 |
| 108 | 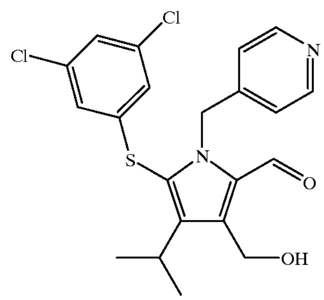 | 5-(3,5-Dichlorophenylthio)-3-(hydroxymethyl)-4-isopropyl-1-[(4-pyridyl)methyl]-1H-pyrrole-2-carboxaldehyde | 438 | 6 |
| 109 | 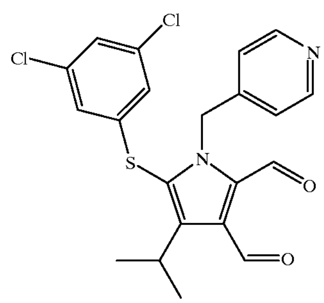 | 5-(3,5-Dichlorophenylthio)-4-isopropyl-1-[(4-pyridyl)methyl]-1H-pyrrole-2,3-dicarboxaldehyde | 433 | 6 |
| 110 | 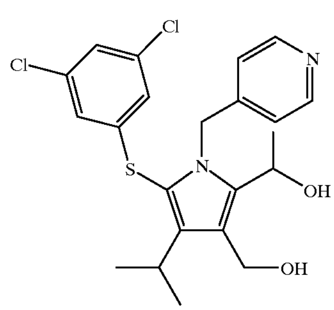 | 5-(3,5-Dichlorophenylthio)-3-(hydroxymethyl)-4-isopropyl-alpha(RS)-methyl-1-[(4-pyridyl)methyl]-1H-pyrrole-2-ethanol | 451 | 6 |

| Ex. | STRUCTURE | SYSTEMATIC NAME | Mass Spectrum (m/z ES, +ve ion) | Reaction Scheme |
|---|---|---|---|---|
| 111 | 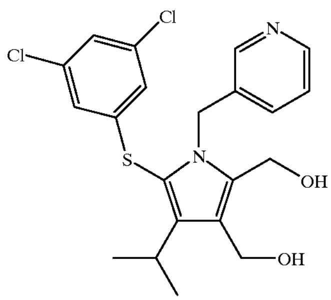 | 5-(3,5-Dichlorophenylthio)-4-isopropyl-1-[(3-pyridyl)methyl]-1H-pyrrole-2,3-dimethanol | 437 | 6 |

Examples 112–131

In a manner analogous to the process described in Reaction Scheme 8 or 9, the following compounds were prepared:

| Ex. | STRUCTURE | SYSTEMATIC NAME | Mass Spectrum (m/z ES, +ve ion) | Reaction Scheme |
|---|---|---|---|---|
| 112 | 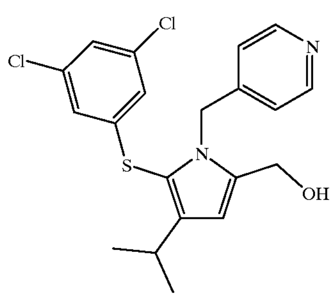 | 5-(3,5-Dichlorophenylthio)-4-isopropyl-1-[(4-pyridyl)methyl]-1H-pyrrole-2-methanol | 407 | 8 |
| 113 | 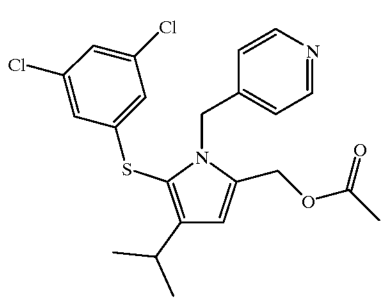 | [5-(3,5-Dichlorophenylthio)-4-isopropyl-1-[(4-pyridyl)methyl]-1H-pyrrol-2-yl]methyl acetate | 447 | 8 |

-continued

| Ex. | STRUCTURE | SYSTEMATIC NAME | Mass Spectrum (m/z ES, +ve ion) | Reaction Scheme |
|---|---|---|---|---|
| 113a | 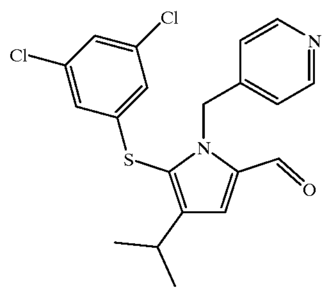 | 5(3,5-Dichlorophenylthio)-4-isopropyl-1-[(4-pyridyl)methyl]-1H-pyrrole-2-carbaldehyde | 405 | 8 |
| 114 | 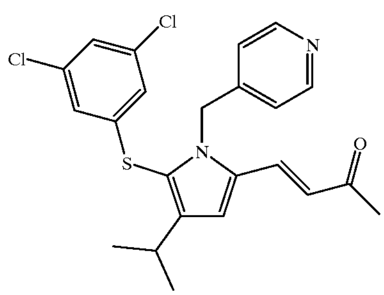 | 4-[5-(3,5-Dichloro-phenylsulfanyl)-4-isopropyl-1-pyridin 4-ylmethyl-1H-pyrrol-2-yl]-but-3-en-2-one | 445 | 8 |
| 115 | 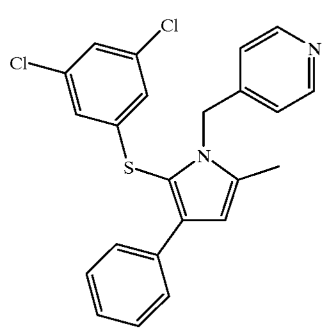 | 4-[[2-(3,5-Dichlorophenylthio)-5-methyl-3-phenyl-1-pyrrolyl]methyl]pyridine | 425 | 8 |
| 115a | 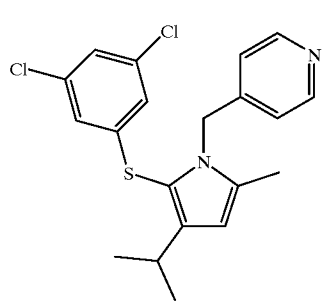 | 4-[[2-(3,5-Dichlorophenylthio)-3-isopropyl-5-methyl-1-pyrrolyl]methyl]pyridine | 391 | 8 |

-continued

| Ex. | STRUCTURE | SYSTEMATIC NAME | Mass Spectrum (m/z ES, +ve ion) | Reaction Scheme |
|---|---|---|---|---|
| 116 | 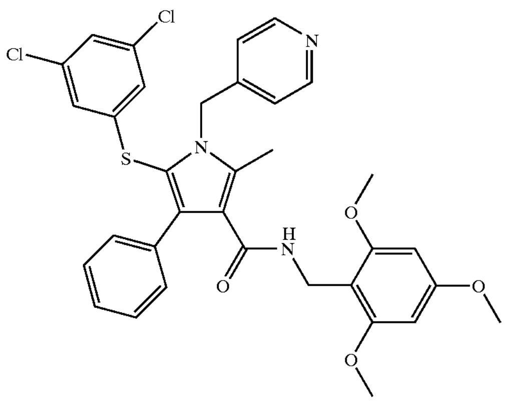 | 5-(3,5-Dichlorophenylthio)-N-(2,4,6-trimethoxybenzyl)-2-methyl-4-phenyl-1-[(4-pyridyl)methyl]-1H-pyrrole-3-carboxamide | 648 | 8 |
| 117 | 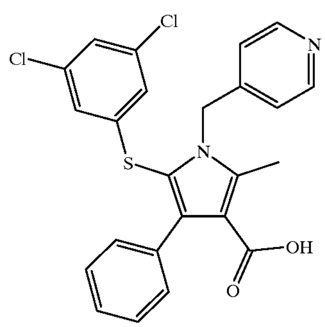 | 5-(3,5-Dichlorophenylthio)-2-methyl-4-phenyl-1-[(4-pyridyl)methyl]-1H-pyrrole-3-carboxylic acid trifluoroacetate (1:1) | 469 | 8 |
| 118 | 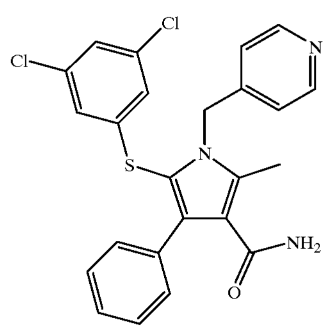 | 5-(3,5-Dichlorophenylthio)-4-phenyl-2-methyl-1-[(4-pyridyl)methyl]-1H-pyrrole-3-carboxamide | 468 | 8 |
| 119 | 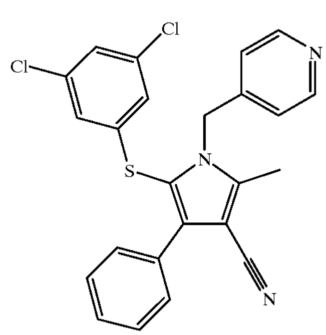 | 5-(3,5-Dichlorophenylthio)-2-methyl-4-phenyl-1-[(4-pyridyl)methyl]-1H-pyrrole-3-carbonitrile | 450 | 8 |

-continued

| Ex. | STRUCTURE | SYSTEMATIC NAME | Mass Spectrum (m/z ES, +ve ion) | Reaction Scheme |
|---|---|---|---|---|
| 120 | 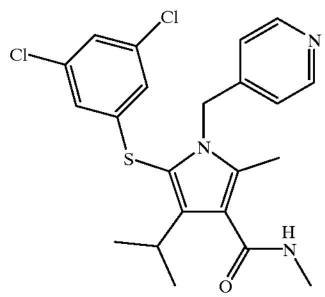 | 5-(3,5-Dichlorophenylthio)-4-isopropyl-N,2-dimethyl-1-[(4-pyridyl)methyl]-1H-pyrrole-3-carboxamide | 448 | 8 |
| 121 | 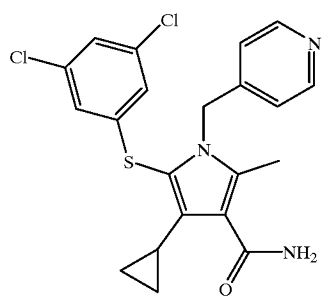 | 5-(3,5-Dichlorophenylthio)-4-cyclopropyl-2-methyl-1-[(4-pyridyl)methyl]-1H-pyrrole-3-carboxamide | 432 | 8 |
| 122 | 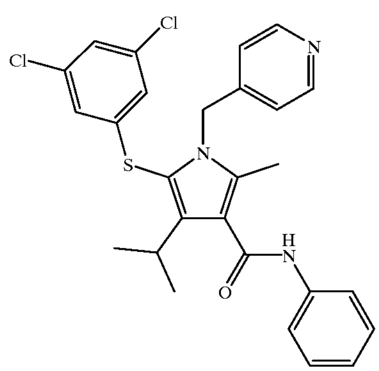 | 5-(3,5-Dichlorophenylthio)-4-isopropyl-2-methyl-1-[(4-pyridyl)methyl]-1H-pyrrole-3-carboxanilide | 510 | 8 |
| 123 | 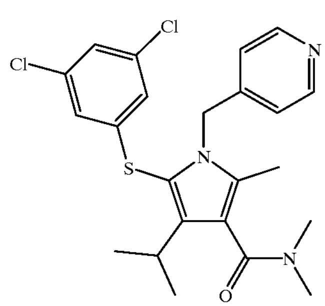 | 5-(3,5-Dichlorophenylthio)-4-isopropyl-N,N,2-trimethyl-1-[(4-pyridyl)methyl]-1H-pyrrole-3-carboxamide | 462 | 8 |

-continued

| Ex. | STRUCTURE | SYSTEMATIC NAME | Mass Spectrum (m/z ES, +ve ion) | Reaction Scheme |
|---|---|---|---|---|
| 124 | 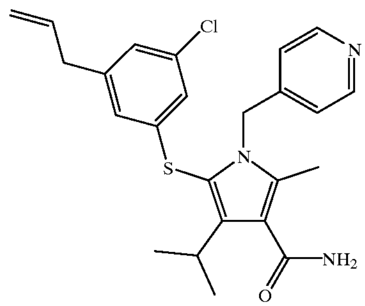 | 5-(3-Allyl-5-chlorophenylthio)-4-isopropyl-2-methyl-1-[(4-pyridyl)methyl]-1H-pyrrole-3-carboxamide | 440 | 8 |
| 125 | 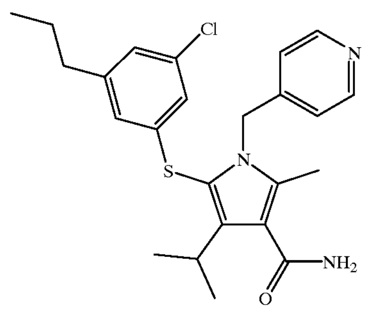 | 5-(3-Chloro-5-propylphenylthio)-4-isopropyl-2-methyl-1-[(4-pyridyl)methyl]-1H-pyrrole-3-carboxamide | 442 | 8 |
| 126 | 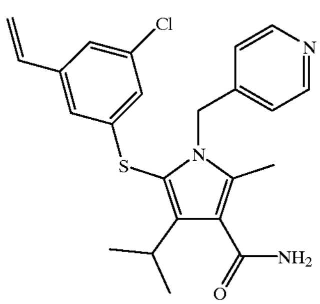 | 5-(3-Chloro-5-vinylphenylthio)-4-isopropyl-2-methyl-1-[(4-pyridyl)methyl]-1H-pyrrole-3-carboxamide | 426 | 8 |
| 127 | 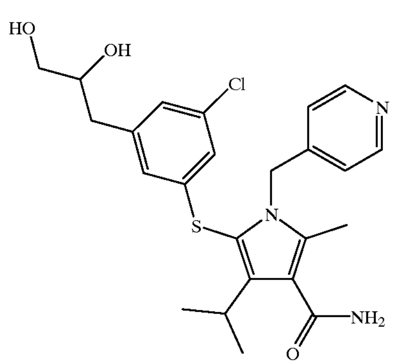 | 5-[3-Chloro-5-(2(RS),3-dihydroxypropyl)phenylthio]-4-isopropyl-2-methyl-1-[(4-pyridyl)methyl]-1H-pyrrole-3-carboxamide | 474 | 8 |

-continued

| Ex. | STRUCTURE | SYSTEMATIC NAME | Mass Spectrum (m/z ES, +ve ion) | Reaction Scheme |
|---|---|---|---|---|
| 128 | 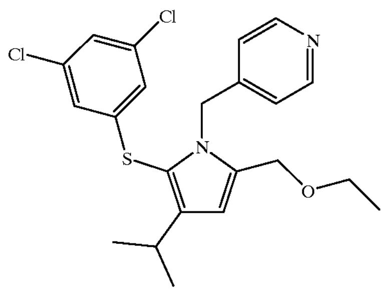 | 4-[[2-(3,5-Dichlorophenylthio)-5-(ethoxymethyl)-3-isopropyl-1-pyrrolyl]methyl]pyridine | 435 | 8 |
| 129 | 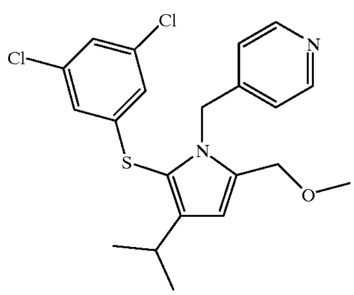 | 4-[[2-(3,5-Dichlorophenylthio)-3-isopropyl-5-(methoxymethyl)-1-pyrrolyl]methyl]pyridine | 421 | 8 |
| 130 | 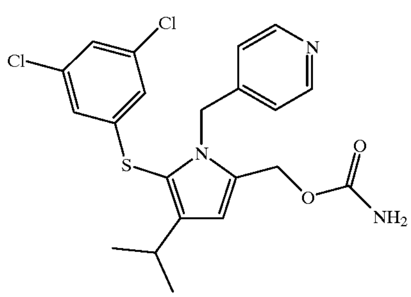 | [5-(3,5-Dichlorophenylthio)-4-isopropyl-1-[(4-pyridyl)methyl]-1H-pyrrol-2-yl]methyl carbamate | 450 | 8 |
| 131 | 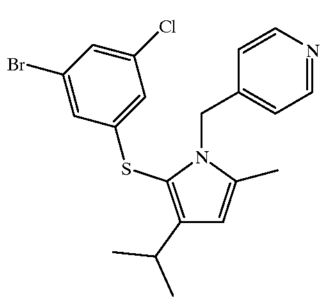 | 4-[[2-(3-Bromo-5-chlorophenylthio)-3-isopropyl-5-methyl-1-pyrrolyl]methyl]pyridine | 435 | 8 |

Examples 132–142

In a manner analogous to the process described in Reaction Scheme 10, the following compounds were prepared:

| Ex. | STRUCTURE | SYSTEMATIC NAME | Mass Spectrum (m/z ES, +ve ion) | Reaction Scheme |
|---|---|---|---|---|
| 132 | 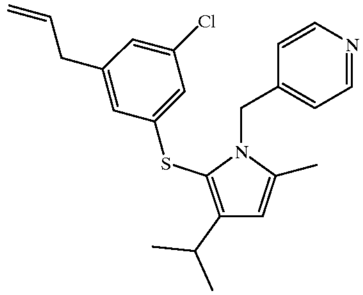 | 4-[[2-(3-Allyl-5-chlorophenylthio)-3-isopropyl-5-methyl-[(4-pyrrolyl]methyl]pyridine | 397 | 10 |
| 133 | 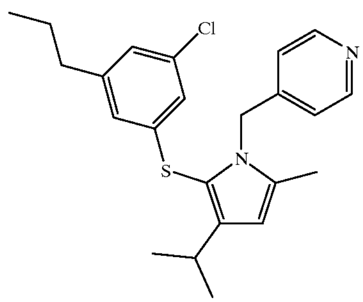 | 4-[[2-(3-Chloro-5-propylphenylthio)-3-isopropyl-5-methyl-1-pyrrolyl]methyl]pyridine | 399 | 10 |
| 134 | 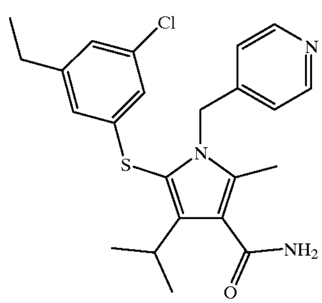 | 5-(3-Chloro-5-ethylphenylthio)-4-isopropyl-2-methyl-1-[(4-pyridyl)methyl]-1H-pyrrole-3-carboxamide | 428 | 10 |
| 135 | 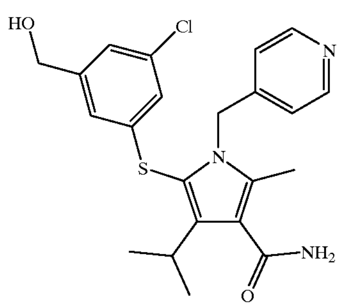 | 5-[3-Chloro-5-(hydroxymethyl)phenylthio]-4-isopropyl-2-methyl-1-[(4-pyridyl)methyl]-1H-pyrrole-3-carboxamide | 430 | 10 |

-continued

| Ex. | STRUCTURE | SYSTEMATIC NAME | Mass Spectrum (m/z ES, +ve ion) | Reaction Scheme |
|---|---|---|---|---|
| 136 | 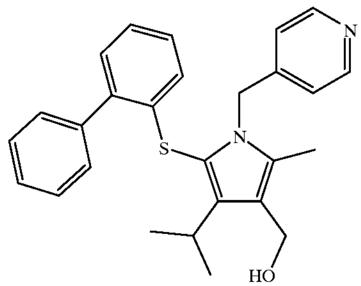 | 5-(2-Biphenylylthio)-4-isopropyl-2-methyl-1-[(4-pyridyl)methyl]-1H-pyrrol-3-methanol | 428 | 10 |
| 137 | 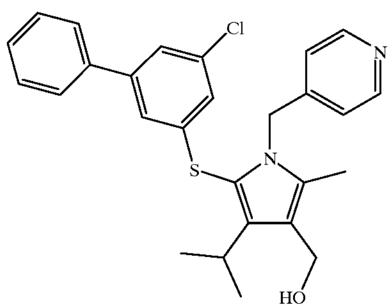 | 5-(3-Biphenylylthio)-4-isopropyl-2-methyl-1-[(4-pyridyl)methyl]-1H-pyrrole-3-methanol | 428 | 10 |
| 138 | 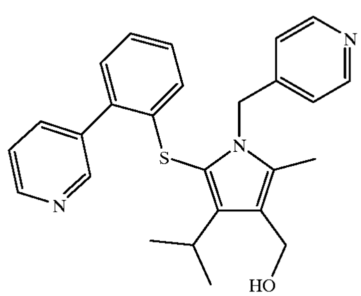 | 4-Isopropyl-2-methyl-1-[(4-pyridyl)methyl]-5-[2-(3-pyridyl)phenylthio]-1H-pyrrole-3-methanol | 429 | 10 |
| 139 | 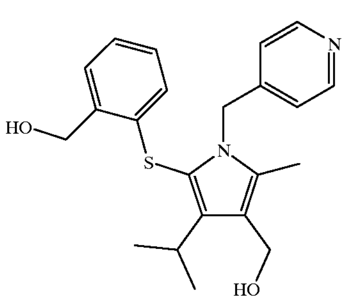 | 5-[2-(Hydroxymethyl)phenylthio]-4-isopropyl-2-methyl-1-[(4-pyridyl)methyl]-1H-pyrrole-3-methanol | 382 | 10 |

| Ex. | STRUCTURE | SYSTEMATIC NAME | Mass Spectrum (m/z ES, +ve ion) | Reaction Scheme |
|---|---|---|---|---|
| 140 | 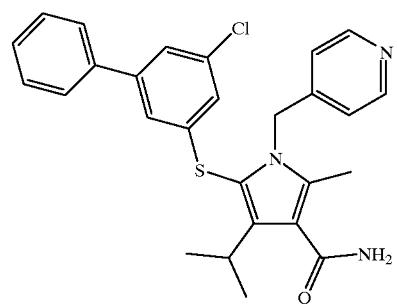 | 5-(5-Chloro-3-biphenylylthio)-4-isopropyl-2-methyl-1-[(4-pyridyl)methyl]-1H-pyrrole-3-carboxamide | 476 | 10 |
| 141 | 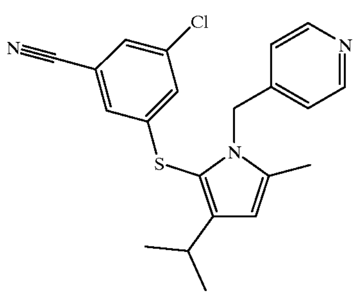 | 3-Chloro-5-[3-isopropyl-5-methyl-1-[(4-pyridinyl)methyl]-1H-pyrrol-2-ylthio]benzonitrile | 382 | 10 |
| 142 | 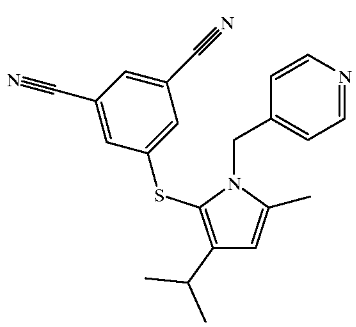 | 5-[3-Isopropyl-5-methyl-1-[(4-pyridyl)methyl]-1H-pyrrol-2-ylthio]-1,3-dibenzonitrile | 372 | 10 |

The foregoing examples merely illustrate the invention and are not intended to limit the scope of the invention. Moreover, it will be apparent to those of ordinary skill in the art that certain modifications and variations of the present invention are possible without departing from the spirit and scope of the invention, and that, such limitations are within the scope of the following claims.

What is claimed is:

1. A compound of formula I

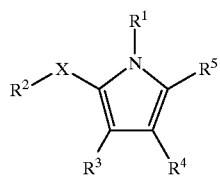

I or the hydrolyzable esters or ethers of such compound, or a pharmaceutically acceptable salt thereof, wherein $R^1$ is methyl or ethyl substitute with pyridinyl;

$R^2$ is alkyl, cycloalkyl, aryl;

$R^3$ is hydrogen, alkyl, cycloalkyl, or aryl;

$R^4$ is hydrogen, alkyl, carboxyl, C(=O)R, CONR'R", cyano or alkenyl;

R is hydrogen, alkyl, alkoxy, trifluoromethyl, methyl-oxy-carbonyl or ethyl-oxy-carbonyl;

R' and R", are each independently selected from hydrogen, alkyl or aryl;

$R^5$ is alkyl, aryl or a group —Z—C(=O)R'";

Z is a single bond or —CH=CH—;

R'" is hydrogen or alkyl; and

X represents S, S(O), S(O)$_2$, or O; and provided that only one of $R^3$ and $R^4$ is hydrogen.

2. The compound of claim 1 wherein $R^1$ is methyl or ethyl substituted with pyridinyl;

$R^2$ is alkyl or aryl;

$R^3$ is alkyl, cycloalkyl or aryl;

207

$R^4$ is hydrogen, alkyl, carboxyl, C(=O)R, CONR'R", cyano or alkenyl;

R is hydrogen, alkyl, alkoxy, trifluoromethyl, methyl-oxy-carbonyl or ethyl-oxy-carbonyl;

R' and R", are each independently selected from hydrogen, alkyl or aryl;

$R^5$ is alkyl, aryl or a group —Z—C(=O)R'";

Z is a single bond or —CH=CH—;

R'" is hydrogen or alkyl; and

X represents S, S(O), S(O)$_2$, or O.

3. The compound of claim 1 wherein $R^1$ is methyl or ethyl substituted with pyridinyl;

$R^2$ is $C_{1-7}$ alkyl, phenyl or phenyl substituted with 1–5 substituents selected from $C_{1-7}$ alkyl, halogen and nitro;

$R^3$ is $C_{1-7}$ alkyl, phenyl, $C_{1-7}$ alkyl substituted with 1–3 heterocyclyl or phenyl substituted with 1–5 substituents selected from $C_{1-4}$-alkyl, $C_{1-4}$-alkoxy and halogen;

$R^4$ is hydrogen, $C_{1-7}$ alkyl or $C_{1-7}$ alkyl substituted with 1–3 substituents selected from hydroxy, amino, $C_{1-4}$-alkoxy, phenyl, methyl-oxy-carbonyl, ethyl-oxy-carbonyl, azido, 2-pyridyl-carbonyl-amino, 3-pyridyl-carbonyl-amino, 4-pyridyl-carbonyl-amino, (phenoxy)-carbonyl-amino, (methoxy)-carbonyl-amino, (di-methyl-amino)-carbonyl-amino, (phenyl-amino)-carbonyl-amino, (amino)-carbonyl-amino, (phenyl)-carbonyl-amino, (methyl)-carbonyl-amino, methyl-carbonyl-amino-methyl-carbonyl-amino, (tert.-butyl)-carbonyl-amino-methyl-carbonyl-amino, methyl-sulfonyl-amino, phenyl-sulfonyl-amino, p-toluyl-sulfonyl-amino, (N1-acetyl-O-tert.-butyl-N2-yl)-L-serinamide, (N1-acetyl-N2-yl)-L-serinamide and [N1-(tert.-butoxycarbonyl)-O-tert.-butyl-N2-yl]-L-serinamide;

$R^5$ is $C_{1-7}$ alkyl, phenyl or $C_{1-7}$ alkyl substituted with 1–3 substituents selected from hydroxy, $C_{1-4}$-alkoxy, methyl-carbonyl-oxy and amino-carbonyl-oxy; and X represents S or O.

4. The compound of claim 1 wherein $R^1$ is methyl substituted by pyridinyl;

$R^2$ is methyl, n-propyl or phenyl substituted with 1–5 chlorine atoms;

$R^3$ is isopropyl or n-propyl;

$R^4$ is hydrogen or $C_{1-2}$ alkyl substituted with 1–3 substituents selected from hydroxy, amino, $C_{1-2}$-alkoxy, 2-pyridyl-carbonyl-amino, 3-pyridyl-carbonyl-amino, 4-pyridyl-carbonyl-amino, (phenoxy)-carbonyl-amino, (methoxy)-carbonyl-amino, (di-methyl-amino)-carbonyl-amino, (phenyl-amino)-carbonyl-amino, (amino)-carbonyl-amino, (phenyl)-carbonyl-amino, (methyl)-carbonyl-amino, methyl-carbonyl-amino-methyl-carbonyl-amino, (tert.-butyl)-carbonyl-amino-methyl-carbonyl-amino, (N1-acetyl-O-tert.-butyl-N2-yl)-L-serinamide, (N1-acetyl-N2-yl)-L-serinamide and [N1-(tert.-butoxycarbonyl)-O-tert.-butyl-N2-yl]-L-serinamide;

$R^5$ is methyl, ethyl, n-propyl, isopropyl, n-butyl, sec-butyl, isobutyl, tert.-butyl or $C_{1-2}$-alkyl substituted with 1–3 substituents selected from hydroxy, $C_{1-2}$-alkoxy, methyl-carbonyl-oxy and amino-carbonyl-oxy; and X represents S or O.

5. The compound of claim 1 wherein $R^1$ is 4-pyridylmethyl;

$R^2$ is methyl or 3,5-dichlorophenyl;

208

$R^3$ is isopropyl;

$R^4$ is $C_{1-2}$ alkyl substituted with 1–2 substituents selected from hydoxy, 2-pyridyl-carbonyl-amino, 3-pyridyl-carbonyl-amino, 4-pyridyl-carbonyl-amino, (phenoxy)-carbonyl-amino, (methoxy)-carbonyl-amino, (di-methyl-amino)-carbonyl-amino, (phenyl-amino)-carbonyl-amino, (amino)-carbonyl-amino, (phenyl)-carbonyl-amino, (methyl)-carbonyl-amino, methyl-carbonyl-amino-methyl-carbonyl-amino, (tert.-butyl)-carbonyl-amino-methyl-carbonyl-amino, (N1-acetyl-O-tert.-butyl-N2-yl)-L-serinamide, (N1-acetyl-N2-yl)-L-serinamide and [N1-(tert.-butoxycarbonyl)-O-tert.-butyl-N2-yl]-L-serinamide;

$R^5$ is methyl, ethyl, n-propyl, isopropyl or $C_{1-2}$-alkyl substituted with 1–3 substituents selected from hydroxy, methyl-carbonyl-oxy and amino-carbonyl-oxy; and X represents S or O.

6. The compound of claim 1 wherein X represents S.

7. The compound of formula I or the hydrolyzable esters or ethers of such compound, or a pharmaceutically acceptable salt thereof, wherein $R^1$ is methyl or ethyl substituted with pyridinyl;

$R^2$ is alkyl, cycloalkyl, or aryl;

$R^3$ is hydrogen, alkyl, cycloalkyl, or aryl;

$R^4$ is hydrogen, alkyl, carboxyl, C(=O)R or CONR'R";

$R^5$ is hydrogen or alkyl; and

X represents S, S(O), S(O)$_2$, or O;

provided that only one of $R^3$, $R^4$ and $R^5$ is hydrogen.

8. The compound claim 7 wherein

X represents S, S(O), S(O)$_2$, or O.

9. The compound of claim 7 wherein X represents S.

10. The compound of claim 9 wherein $R^2$ is alkyl or aryl;

$R^3$ is alkyl or aryl; and $R^4$ is hydrogen, alkyl, carboxyl, C(=O)R or CONR'R".

11. The compound of claim 10 wherein $R^2$ is unsubstituted alkyl, unsubstituted phenyl or substituted phenyl with 1 to 5 halogen or nitro or unsubstituted $C_{1-7}$ alkyl as substituents;

$R^4$ is hydrogen, unsubstituted alkyl or substituted alkyl with hydroxy or amino or methoxy as substituents, carboxyl, C(=O)R, CONR'R";

$R^5$ is hydrogen, unsubstituted alkyl or substituted alkyl with hydroxy as substituent; and X represents S.

12. The compound of claim 11 wherein $R^2$ is methyl, n-propyl or chlorinated phenyl;

$R^3$ is isopropyl, n-propyl or pyridylmethyl;

$R^4$ is carboxyl, C(=O)R, CONR$_2$, methyl or ethyl each of methyl and ethyl being independently substituted with hydroxy or methoxy;

$R^5$ is methyl or ethyl each of which is optionally substituted with a hydroxy group; and X represents S.

13. The compound of claim 12 wherein $R^1$ is 4-pyridyl methyl;

$R^2$ is methyl or 3,5-dichlorophenyl;

$R^3$ is isopropyl;

$R^4$ is methyl substituted with a hydroxy group or C(=O)R;

$R^5$ is methyl; and

X represents S.

14. A compound selected from:

5-(3,5-Dichlorophenylthio)-4-isopropyl-2-methyl-1-[(4-pyridyl)methyl]-1H-pyrrole-3-methanol, 5-(3,5-Dichlorophenylthio)-4-isopropyl-2-methyl-1-[(4-pyridyl)methyl]-1H-pyrrole-3-carboxaldehyde, 5-(3,5-Dichlorophenylthio)-4-isopropyl-alpha(RS)-methyl-1-[(4-pyridyl)methyl]-1H-pyrrole-3-ethanol, 5-(3,5-Dichlorophenylthio)-4-isopropyl-2-methyl-1-[(2-pyridyl)methyl]-1H-pyrrole-3-methanol, 5-(3,5-Dichlorophenylthio)-4-isopropyl-2-methyl-1-[(3-pyridyl)methyl]-1H-pyrrole-3-methanol, 4-Isopropyl-2-methyl-5-phenylthio-1-[(4-pyridyl)methyl]-1H-pyrrole-3-methanol, 5-(3-Chlorophenylthio)-4-isopropyl-2-methyl-1-[(4-pyridyl)methyl]-1H-pyrrole-3-methanol, 4-Isopropyl-2-methyl-5-(3-nitrophenylthio)-1-[(4-pyridyl)methyl]-1H -pyrrole-3-methanol, 5-(3,5-Dimethylphenylthio)-4-isopropyl-2-methyl-1-[(4-pyridyl)methyl]1H -pyrrole-3-methanol, 4-Isopropyl-5-isopropylthio-2-methyl-1-[(4-pyridyl)methyl]-1H -pyrrole-3-methanol, 4-Isopropyl-2-methyl-5-methylthio-1-[(4-pyridyl)methyl]-1H -pyrrole-3-methanol, 5-(3,5-Dichlorophenylthio)-2-methyl-4-phenyl-1-[(4-pyridyl)methyl]-1H -pyrrole-3-methanol, 4-(4-Chlorophenyl)-5(3,5-dichlorophenylthio)-2-methyl-1-[(4-pyridyl)methyl]-1H-pyrrole-3-methanol, 5-(3,5-Dichlorophenylthio)-2-methyl-4-(4-methylphenyl)-1-[(4-pyridyl)methyl]-1H-pyrrole-3-methanol, 5-(3,5-Dichlorophenylthio)-4-(4-methoxyphenyl)-2-methyl-1-[(4-pyridyl)methyl]-1H-pyrrole-3-methanol, 4-(3,4-Dichlorophenyl)-5-(3,5-dichlorophenylthio)-2-methyl-1-[(4-pyridyl)methyl]-1H-pyrrole-3-methanol, 5-(3,5-Dichlorophenylthio)-4-isopropyl-2-methyl-1-[(4-pyridyl)methyl]-1H-pyrrole-3-carboxylic acid, 5-(3,5-Dichlorophenylthio)-4-isopropyl-2-methyl-1-[(4-pyridyl)methyl]-1H-pyrrole-3-carboxamide, 4-[[2-(3,5-Dichlorophenylthio)-3-isopropyl-4-(methyl-1H-pyrrol-1-yl]methyl]pyridine, 5-(3,5-Dichlorophenylthio)-3-(hydroxymethyl)-4-isopropyl-1-[(4-pyridyl)methyl]-1H-pyrrole-2-methanol, 5-(3,5-Dichlorophenylthio)-4-isopropyl-1-[(4-pyridyl)methyl]-1H-pyrrole-3-methanol, 5-(3,5-Dichlorophenylthio)-2-ethyl-4-isopropyl-1-[(4-pyridyl)methyl]-1H-pyrrole-3-methanol, 5-(3,5-Dichlorophenoxy)-4-isopropyl-2-methyl-1-[(4-pyridyl)methyl]-1H-pyrrole-3-methanol, 5-(3,5-Dichlorophenylthio)-1-isopropyl-3-methyl-4-[(4-pyridyl)methyl]-1H-pyrrole-2-methanol, 5-(3,5-Dichlorophenylthio)-4-isopropyl-1-[(4-pyridyl)methyl]-1H-pyrrole-2-methanol, and 5-(3,5-Dichlorophenylthio)-4-isopropyl-3-methyl-14-[(4-pyridyl)methyl]-1H-pyrrole-2-methanol.

15. A compound selected from:

5-(3,5-Dichlorophenylthio)-4-isopropyl-2-methyl-1-[(4-pyridyl)methyl]-1H-pyrrole-3-methanol, 5-(3,5-Dichlorophenylthio)-4-isopropyl-2-methyl-1-[(4-pyridyl)methyl]-1H-pyrrole-3-carboxaldehyde, 5-(3,5-Dichlorophenylthio)-4-isopropyl-alpha(RS)-methyl-1-[(4-pyridyl)methyl]-1H-pyrrole-3-ethanol, 5-(3,5-Dichlorophenylthio)-4-isopropyl-2-methyl-1-[(2-pyridyl)methyl]-1H-pyrrole-1H-pyrrole-3-methanol, 5-(3,5-Dichlorophenylthio)-4-isopropyl-2-methyl-1-[(3-pyridyl)methyl]-1H-pyrrole-3-methanol, 4-Isopropyl-2-methyl-5-phenylthio-1-[(4-pyridyl)methyl]-1H-pyrrole-3-methanol, 5-(3-Chlorophenylthio)-4-isopropyl-2-methyl-1-[(4-pyridyl)methyl]-1H-pyrrole-3-methanol, 4-Isopropyl-2-methyl-5-(3-nitrophenylthio)-1-[(4-pyridyl)methyl]-1H-pyrrole-3-methanol, and 5-(3,5-Dimethylphenylthio)-4-isopropyl-2-methyl-1-[(4-pyridyl)methyl]-1H-pyrrole-3-methanol.

16. A compound selected from:

4-Isopropyl-5-isopropylthio-2-methyl-1-[(4-pyridyl)methyl]-1H-pyrrole-3-methanol, 4-Isopropyl-2-methyl-5-methylthio-1-[(4-pyridyl)methyl]-1H-pyrrole-3-methanol, 5-(3,5-Dichlorophenylthio)-2-methyl-4-phenyl-1-[(4-pyridyl)methyl]-1H-pyrrole-3-methanol, 4-(4-Chlorophenyl)-5-(3,5-dichlorophenylthio)-2-methyl-1-[(4-pyridyl)methyl]-1H-pyrrole-3-methanol, 5-(3,5-Dichlorophenylthio)-2-methyl-4-(4-methylphenyl)-1-[(4-pyridyl)methyl]-1H-pyrrole-3-methanol, 5-(3,5-Dichlorophenylthio)-4-(4-methoxyphenyl)-2-methyl-1-[(4-pyridyl)methyl]-1H-pyrrole-3-methanol, 4-(3,4-Dichlorophenyl)-5-(3,5-dichlorophenylthio)-2-methyl-1-[(4-pyridyl)methyl]-1H-pyrrole-3-methanol, 5-(3,5-Dichlorophenylthio)-4-isopropyl-2-methyl-1-[(4-pyridyl)methyl]-1H-pyrrole-3-carboxylic acid, 5-(3,5-Dichlorophenylthio)-4-isopropyl-2-methyl-1-[(4-pyridyl)methyl]-1H-pyrrole-3-carboxamide, 4-[[2-(3,5-Dichlorophenylthio)-3-isopropyl-4,5-dimethyl-1H-pyrrol-1-yl]methyl]pyridine, 5-(3,5-Dichlorophenylthio)-4-isopropyl-2-methyl-1-[(4-pyridyl)methyl]-1H-pyrrole-3-methylamine, 4-[[2-(3,5-Dichlorophenylthio)-3-isopropyl-4-(methoxymethyl)-5-methyl-1H-pyrrol-1-yl]methyl]pyridine, 5-(3,5-Dichlorophenylthio)-3-(hydroxymethyl)-4-isopropyl-1-[(4-pyridyl)methyl]-1H-pyrrole-2-methanol, 5-(3,5-Dichlorophenylthio)-4-isopropyl-1-[(4-pyridyl)methyl]-1H-pyrrole-3-methanol, 5-(3,5-Dichlorophenylthio)-2-ethyl-4-isopropyl-1-[(4-pyridyl)methyl]-1H-pyrrole-3-methanol, and 5-(3,5-Dichlorophenoxy)-4-isopropyl-2-methyl-1-[(4-pyridyl)methyl]-1H-pyrrole-3-methanol.

17. A compound selected from:

5-Benzyl-4-isopropyl-2-methyl-1-[(4-pyridyl)methyl]-1H-pyrrole-3-methanol,

4-Isopropyl-2-methyl-1,5-bis[(4-pyridyl)methyl]-1H-pyrrole-3-methanol,]

5-(3,5-Dichlorophenylthio)-1-isopropyl-3-methyl-4-[(4-pyridyl)methyl]-1H-pyrrole-2-methanol, 5-(3,5-Dichlorophenylthio)-4-isopropyl-1-[(4-pyridyl)methyl]-1H-pyrrole-2-methanol, 5-(3,5-Dichlorophenylthio)-4-isopropyl-3-methyl-1-[(4-pyridyl)methyl]-1H-pyrrole-2-methanol, 5-(3,5-Dichlorophenylthio)-2,4-dimethyl-1-[(4-pyridyl)methyl]-1H-pyrrole-3-methanol, 5-(3,5-Dichlorophenylthio)-4-isopropyl-2-phenyl-1-[(4-pyridyl)methyl]-1H-pyrrole-3-methanol, 5-(3,5-Dichlorophenylthio)-4-isopropyl-2-methyl-1-[(3-pyridyl)methyl]-1H-pyrrole-3-methanol, 5-(2-chloro-4-fluorophenylthio)-4-isopropyl-2-methyl-1-[(4-pyridyl)methyl]-1H-pyrrole-3-methanol, 4-Isopropyl-5-(4-methoxyphenylthio)-2-methyl-1-[(4-pyridyl)methyl]-1H-pyrrole-3-methanol, 5-(2-Chlorophenylthio)-4-isopropyl-2-methyl-1-[(4-pyridyl)methyl]-1H-pyrrole-3-methanol, 5-[3-(Trifluoromethyl)phenylthio]-4-isopropyl-2-methyl-1-[(4-pyridyl)methyl]-1H-pyrrole-3-methanol, 5-[4-(Trifluoromethoxy)phenylthio]-4-isopropyl-2-methyl-1-[(4-pyridyl)methyl]-1H-pyrrole-3-methanol, 5-(2,5-Dichlorophenylthio)-4-isopropyl-2-methyl-1-[(4-pyridyl)methyl]-1H-pyrrole-3-methanol, and 5-(3,5-Dichlorophenylthio)-2,4-diisopropyl-1-[(4-pyridyl)methyl]-1H-pyrrole-3-methanol.

18. A compound selected from:

4-Isopropyl-2-methyl-5-(2-naphthylthio)-1[(4-pyridinyl)methyl]-1H-pyrrole-3-methanol, 5-(2,4-Dichlorophenylthio)-4-isopropyl-2-methyl-1-[(4-pyridyl)methyl]-1H-pyrrole-3-methanol, 5-(3-Fluorophenylthio)-4-isopropyl-2-methyl-1-[(4-pyridyl)methyl]-1H-pyrrole-3-methanol, 5-(3-Chlorophenylthio)-2,4-diisopropyl-1-[(4-pyridyl)methyl]-1H-pyrrole-3-methanol, 4-Isopropyl-5-(3,4-dimethoxyphenylthio)-2-methyl-1-[(4-pyridyl)methyl]-1H-pyrrole-3-methanol, 4-Isopropyl-2-methyl-5-(2,4,6-trimethylphenylthio)-1-[(4-pyridyl)methyl]-1H-pyrrole-3-methanol, 4-Isopropyl-2-methyl-5-(3,4-dimethylphenylthio)-1-[(4-pyridyl)methyl]-1H-pyrrole-3-methanol, 4-Isopropyl-5-(2,5-dimethoxyphenylthio)-2-methyl-1-[(4-pyridyl)methyl]-1H-pyrrole-3-methanol, 4-Isopropyl-2-methyl-5-(2,5-dimethylphenylthio)-1-[(4-pyridyl)methyl]-1H-pyrrole-3-methanol, 4-Isopropyl-5-(2-methoxyphenylthio)-2-methyl-1-[(4-pyridyl)methyl]-1H-pyrrole-3-methanol, 5-(2-Fluorophenylthio)-4-isopropyl-2-methyl-1-[(4-pyridyl)methyl]-1H-pyrrole-3-methanol, and 4-Isopropyl-2-methyl-5-(4-methylphenylthio)-1-[(4-pyridyl)methyl]-1H-pyrrole-3-methanol.

19. A compound selected from:

alpha(RS)-[5-(3,5-Dichlorophenylthio)-4-isopropyl-2-methyl-1-[(4-pyridyl)methyl]-1H-pyrrol-3-yl]benzyl alcohol, 5-(3-Chlorophenylthio)-4-isopropyl-2-methyl-1-[(3-(4-pyridyl)propyl]-1H-pyrrole-3-methanol, 4-Isopropyl-2-methyl-5-(2,4-dimethylphenylthio)-1-[(4-pyridyl)methyl]-1H-pyrrole-3-methanol, 4-Isopropyl-2-methyl-5-(3-methylphenylthio)-1-[(4-pyridyl)methyl]-1H-pyrrole-3-methanol, 5-(2-Chloro-6-methylphenylthio)-4-isopropyl-2-methyl-1-[(4-pyridyl)methyl]-1H-pyrrole-3-methanol, 5-(4-Ethylphenylthio)-4-isopropyl-2-methyl-1-[(4-pyridyl)methyl]-1H-pyrrole-3-methanol, 4-Isopropyl-5-(3-methoxyphenylthio)-2-methyl-1-[(4-pyridyl)methyl]-1H-pyrrole-3-methanol, 5-(2,4,6-Trichlorophenylthio)-4-isopropyl-2-methyl-1-[(4-pyridyl)methyl]-1H-pyrrole-3-methanol, 5-(3-Chlorophenylthio)-1-[[6-(trifluoromethyl)-3-pyridyl]methyl]-4-isopropyl-2-methyl-1H-pyrrole-3-methanol, 5-(3,5-Dichloro-phenylsulfanyl)-4-isopropyl-2-methyl-1-pyridin-4-ylmethyl-1H-pyrrol-3-yl-hydroxy-acetic acid ethyl ester, and N-[[5-(3,5-Dichlorophenylthio)-4-isopropyl-2-methyl-1-[(4-pyridyl)methyl]-1H-pyrrol-3-yl]methyl]-4-pyridineacetamide.

20. A compound selected from:

2-Acetamido-N-[[5-(3,5-dichlorophenylthio)-4-isopropyl-2-methyl-i -[(4-pyridyl)methyl]-1H-pyrrol-3-yl]methyl]acetamide, N-[[5-(3,5-Dichlorophenylthio)-4-isopropyl-2-methyl-1-[(4-pyridyl)methyl]-1H-pyrrol-3-yl]methyl]-p-toluenesulfonamide, tert.-butyl [[[[5-(3,5-dichlorophenylthio)-4-isopropyl-2-methyl-1-[(4-pyridyl)methyl]-1H-pyrrol-3-yl]methyl]carbamoyl]methyl]carbamate, N2-[[5-(3,5-Dichlorophenylthio)-4-isopropyl-2-methyl-1-[(4-pyridyl)methyl]-1H-pyrrol-3-yl]methyl]glycinamide, N-[[5-(3,5-Dichlorophenylthio)-4-isopropyl-2-methyl-1-[(4-pyridyl)methyl-1H-pyrrol-3-yl]methyl]methanesulfonamide, Phenyl [[5-(3,5-dichlorophenylthio)-4-isopropyl-2-methyl-1-[(4-pyridyl)methyl]-1H-pyrrol-3-yl]methyl]carbamate, Methyl [[5-(3,5-dichlorophenylthio)-4-isopropyl-2-methyl-1-[(4-pyridyl)methyl]-1H-pyrrol-3-yl]methyl]carbamate, N-[[5-(3,5-Dichlorophenylthio)-4-isopropyl-2-methyl-1-[(4-pyridyl)methyl]-1H-pyrrol-3-yl]methyl]benzenesulfonamide, N1-acetyl-O-tert.-butyl-N2-[[5-(3,5-dichlorophenylthio)-4-isopropyl-2-methyl-1-[(4-pyridyl)methyl]-1H-pyrrol-3-ylmethyl]-L-serinamide, N1-acetyl-N2-[[5-(3,5-dichlorophenylthio)-4-isopropyl-2-methyl-1-[(4-pyridyl)methyl]-1H-pyrrol-3-yl]methyl]-L-serinamide, N1-(tert.-butoxycarbonyl)-O-tert.-butyl-N2-[[5-(3,5-dichlorophenylthio)-4-isopropyl-2-methyl-1-[(4-pyridyl)methyl]-1H-pyrrol-3-yl]methyl]-L-serinamide, 1-[[5-(3,5-Dichlorophenylthio)-4-isopropyl-2-methyl-1-[(4-pyridyl)methyl]-1H-pyrrol-3-yl]methyl]-3,3-dimethylurea, 1-[[5-(3,5-Dichlorophenylthio)-4-isopropyl-2-methyl -1-[(4-pyridyl)methyl]-1H-pyrrol-3-yl]methyl]-3-methyl-3-phenylurea, and 1-[[5-(3,5-Dichlorophenylthio)-4-isopropyl-2-methyl 1-[(4-pyridyl)methyl]-1H-pyrrol-3-yl]methyl]urea.

21. A compound selected from:

4-[[2-(3,5-Dichlorophenylthio)-3-isopropyl-4-(methoxymethyl)-5-methyl-1-pyrrolyl]methyl]pyridine, 4-[[2-(3-Chlorophenylthio)-3-isopropyl-4-(methoxymethyl)-5-methyl-1-pyrrolyl]methyl]pyridine, 4-[[3-(Azidomethyl)-5-(3,5-dichlorophenylthio)-4-isopropyl-2-methyl-1-pyrrolyl]methyl]pyridine, N-[[5-(3,5-Dichlorophenylthio)-4-isopropyl-2-methyl-1-[(4-pyridyl)methyl]-1H-pyrrol-3-yl]methyl]acetamide, 4-[[2-(3,5-Dichlorophenylthio)-3-isopropyl-5-methyl-4-vinyl-1-pyrrolyl]methyl]pyridine, 1(RS)-[5-(3,5-Dichlorophenylthio)-4-isopropyl-2-methyl-1-[(4-pyridyl)methyl]-1H-pyrrol-3-yl]-1,2-ethanediol, N-[[5-(3,5-Dichlorophenylthio)-4-isopropyl-2-methyl-1-[(4-pyridyl)methyl]-1H-pyrrol-3-yl]methyl]benzamide, tert.-butyl 5-(3-bromo-5-chlorophenylthio)-4-isopropyl-2-methyl-1-[(4-pyridyl)methyl]-1H-pyrrole-3-carboxylate, tert.-butyl 5-(3,5-dibromophenylthio)-4-isopropyl-2-methyl-1-[(4-pyridyl)methyl]-1H-pyrrole-3-carboxylate, 1-[5-(3,5-Dichlorophenylthio)-4-isopropyl-2-methyl-1-[(4-pyridyl)methyl]-1H-pyrrol-3-yl]-2,2,2-trifluoroethanone, 1-[5-(3,5-Dichlorophenylthio)-4-isopropyl-2-methyl-1-[(4-pyridyl)methyl]-1H-pyrrol-3-yl]ethanone, 5-(3,5-Dibromophenylthio)-4-isopropyl-2-methyl-1-[(4-pyridyl)methyl]-1H-pyrrole-3-carboxamide, 4-Isopropyl-5-(3,5-dimethoxyphenylthio)-2-methyl-1-[(4-pyridyl)methyl]-1H-pyrrole-3-carboxamide, 5-(3-Bromo-5-chlorophenylthio)-4-isopropyl-2-methyl-1-[(4-pyridyl)methyl]-1H-pyrrole-3-carboxamide, and Ethyl 5-(3,5-dichlorophenylthio)-4-isopropyl-2-methyl-1-[(4-pyridyl)methyl]-1H-pyrrole-3-glyoxalate.

22. A compound selected from:

5-(3-Cyanophenylthio)-4-isopropyl-2-methyl-1-[(4-pyridyl)methyl]-1H-pyrrole-3-carboxamide, 5-(3-Chlorophenylthio)-2-(hydroxymethyl)-4-isopropyl-alpha(RS)-methyl-1-[(4-pyridyl)methyl]-1-[(4-pyridyl)methyl]-1H-pyrrole-3-ethanol, 5-(3,5-Dichlorophenylthio)-3-(hydroxymethyl)-4-isopropyl-1-[(4-pyridyl)methyl]-1H-pyrrole-2-carboxaldehyde, 5-(3,5-Dichlorophenylthio)-4-isopropyl-1-[(4-pyridyl)methyl]-1H-pyrrole-2,3-dicarboxaldehyde, 5-(3,5-Dichlorophenylthio)-3-(hydroxymethyl)-4-isopropyl-alpha(RS)-methyl-1-[(4-pyridyl)methyl]-1H-pyrrole-2-ethanol, 5-(3,5-Dichlorophenylthio)-4-isopropyl-1-[(3-pyridyl]methyl]-1H-pyrrole-2,3-dimethanol, 5-(3,5-Dichlorophenylthio)-4-isopropyl-1-[(4-pyridyl)methyl]-1H-pyrrole-2-methanol,

[5-(3,5-Dichlorophenylthio)-4-isopropyl-1-[(4-pyridyl)methyl]-1H-pyrrol-2-yl]methyl acetate, 5-(3,5-Dichlorophenylthio)-4-isopropyl-1-[(4-pyridyl)methyl]-1H-pyrrole-2-carbaldehyde, 4-[5-(3,5-Dichloro-phenylsulfanyl)-4-isopropyl-1-pyridin-4-ylmethyl-1H-pyrrol-2-yl]-but-3-en-2-one, 4-[[2-(3,5-Dichlorophenylthio)-5-methyl-3-phenyl-1-pyrrolyl]methyl]pyridine, 4-[[2-(3,5-Dichlorophenylthio)-3-isopropyl-5-methyl-1-pyrrolyl]methyl]pyridine, 5-(3,5-Dichlorophenylthio)-N-(2,4,6-trimethoxybenzyl)-2-methyl-4-phenyl-1-[(4-pyridyl)methyl]-1H-pyrrole-3-carboxamide, 5-(3,5-Dichlorophenylthio)-2-methyl-4-phenyl-1-[(4-pyridyl)methyl]-1H-pyrrole-3-carboxylic acid trifluoroacetate (1:1), 5-(3,5-Dichlorophenylthio)-4-phenyl-2-methyl-1-[(4-pyridyl)methyl]-1H-pyrrole-3-carboxamide, and 5-(3,5-Dichlorophenylthio)-2-methyl-4-phenyl-1-[(4-pyridyl)methyl]-1H-pyrrole-3-carbontrile.

23. A compound selected from:

5-(3,5-Dichlorophenylthio)-4-isopropyl-N,2-dimethyl-1-[(4-pyridyl)methyl]-1H-pyrrole-3-carboxamide, 5-(3,5-Dichlorophenylthio)-4-cyclopropyl-2-methyl-1-[(4-pyridyl)methyl]-1H-pyrrole-3-carboxamide, 5-(3,5-Dichlorophenylthio)-4-isopropyl-2-methyl-1-[(4-pyridyl)methyl]-1H-pyrrole-3-carboxanilide, 5-(3,5-Dichlorophenylthio)-4-isopropyl-N,N,2-trimethyl-1-[(4-pyridyl)methyl]-1H-pyrrole-3-carboxamide, 5-(3-Allyl-5-chlorophenylthio)-4-isopropyl-2-methyl-1-[(4-pyridyl)methyl]-1H-pyrrole-3-carboxamide, 5-(3-Chloro-5-propylphenylthio)-4-isopropyl-2-methyl-1-[(4-pyridyl)methyl]-1H-pyrrole-3-carboxamide, 5-(3-Chloro-5-vinylphenylthio)-4-isopropyl-2-methyl-1-[(4-pyridyl)methyl]-1H-pyrrole-3-carboxamide, 5-[3-Chloro-5-(2(RS),3-dihydroxypropyl)phenylthio]-4-isopropyl-2-methyl-1-[(4-pyridyl)methyl]-1H-pyrrole-3-carboxamide, 4-[[2-(3,5-Dichlorophenylthio)-5-(ethoxymethyl)-3-isopropyl-1-pyrrolyl]methyl]pyridine, 4-[[2-(3,5-Dichlorophenylthio)-3-isopropyl-5-(methoxymethyl)-1-pyrrolyl]methyl]pyridine,

[5-(3,5-Dichlorophenylthio)-4-isopropyl-1-[(4-pyridyl)methyl]-1H-pyrrol-2-yl]methyl carbamate, 4-[[2-(3-Bromo-5-chlorophenylthio)-3-isopropyl-5-methyl-1-pyrrolyl]methyl]pyridine, 4-[[2-(3-Allyl-5-chlorophenylthio)-3-isopropyl-5-methyl-[(4-pyrrolyl]methyl]pyridine, and 4-[[2-(3-Chloro-5-propylphenylthio)-3-isopropyl-5-methyl-1-pyrrolyl]methyl]pyridine.

24. A compound selected from:

5(3-Chloro-5-ethylphenylthio)-4-isopropyl-2-methyl-1-[(4-pyridyl)methyl]-1H-pyrrole-3-carboxamide, 5-[3-Chloro-5-(hydroxymethyl)phenylthio]-4-isopropyl-2-methyl-1-[(4-pyridyl)methyl]-1H-pyrrole-3-carboxamide, 5-(2-Biphenylylthio)-4-isopropyl-2-methyl-1-[(4-pyridyl)methyl]-1H-pyrrol-3-methanol, 5-(3-Biphenylylthio)-4-isopropyl-2-methyl-1-[(4-pyridyl)methyl]-1H-pyrrole-3-methanol, 4-Isopropyl-2-methyl-1-[(4-pyridyl)methyl]-5-[2-(3-pyridyl)phenylthio]-1H-pyrrole-3-methanol, 5-[2-(Hydroxymethyl)phenylthio]-4-isopropyl-2-methyl-1-[(4-pyridyl)methyl]-1H-pyrrole-3-methanol, 5-(5-Chloro-3-biphenylylthio)-4-isopropyl-2-methyl-1-[(4-pyridyl)methyl]-1H-pyrrole-3-carboxamide, 3-Chloro-5-[3-isopropyl-5-methyl-1-[(4-pyridinyl)methyl]-1H-pyrrol-2-ylthio]benzonitrile, and 5-[3-Isopropyl-5-methyl-1-[(4-pyridyl)methyl]-1H-pyrrol-2-ylthio]-1,3-dibenzonitrile.

25. A method of treating a disease mediated by the human immunodeficiency virus (HIV) comprising administrating to a patient, in need of such treatment an effective amount of a compound of formula I, claim 1, or a hydrolyzable ester or ether or pharmaceutically acceptable salt thereof.

26. A pharmaceutical composition comprising a pharmaceutically effective amount of a compound of formula I, claim 1, or a hydrolyzable ester, ether or pharmaceutically acceptable salt thereof, as and a pharmaceutical inert carrier.

* * * * *

UNITED STATES PATENT AND TRADEMARK OFFICE
CERTIFICATE OF CORRECTION

PATENT NO. : 6,737,429 B2
APPLICATION NO. : 09/880534
DATED : May 18, 2004
INVENTOR(S) : Brian William Dymock It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (153) days Delete the phrase "by 153 days" and insert --by 98 days--

Col. 208, Line 39 (currently missing) should be
--R' and R" are each independently selected from hydrogen or alkyl;--

Col. 208, Line 43
"The compound claim 7 wherein" should be --The compound of claim 7 wherein--

Col. 209, Line 40
"…-5(3,5-dichlorophenylthio)…" should be --…-5-(3,5-dichlorophenylthio)…--

Col. 209, Line 54
"...4-(methyl-1H-pyrrol…" should be --...4-(methoxymethyl)-5-methyl-1Hpyrrol…--

Col. 210, Line 3
"...3-methyl-14-[(4-…" should be --...3-methyl-1-[(4-…--

Col. 212, Line 18
"...isopropyl-2-methyl-i —[(4…" should be --...isopropyl-2-methyl-1-[(4…--

UNITED STATES PATENT AND TRADEMARK OFFICE
CERTIFICATE OF CORRECTION

PATENT NO. : 6,737,429 B2
APPLICATION NO. : 09/880534
DATED : May 18, 2004
INVENTOR(S) : Brian William Dymock It is certified that error appears in the above-identified patent and that said Letters Patent is hereby corrected as shown below:

Col. 213, Line 35
"...alpha(RS)-methyl-1-[(4-pyridyl_methyl]-1-[4..." should be --...alpha(RS)-methyl-1-[(4-...--

Signed and Sealed this

Twelfth Day of September, 2006

JON W. DUDAS
*Director of the United States Patent and Trademark Office*